United States Patent [19]

Holt et al.

[11] 4,046,737

[45] Sept. 6, 1977

[54] PIPERIDINE DERIVATIVES

[75] Inventors: Brian Holt, Royton; Donald Richard Randell, Stockport, both of England

[73] Assignee: Ciba-Geigy Corporation, Ardsley, N.Y.

[21] Appl. No.: 577,501

[22] Filed: May 14, 1975

Related U.S. Application Data

[62] Division of Ser. No. 310,031, Nov. 28, 1972, abandoned.

[30] Foreign Application Priority Data

| | | |
|---|---|---|
| June 17, 1972 | United Kingdom | 28458/72 |
| Nov. 30, 1971 | United Kingdom | 55487/71 |
| July 28, 1972 | United Kingdom | 35473/72 |

[51] Int. Cl.² ............................................. C08K 5/00
[52] U.S. Cl. ........................ 260/45.8 N; 260/45.85 A

[58] Field of Search ................................ 260/45.8 N

[56] References Cited

U.S. PATENT DOCUMENTS

| | | | |
|---|---|---|---|
| 3,640,928 | 2/1972 | Murayama et al. | 260/45.8 N X |
| 3,663,558 | 5/1972 | Murayama et al. | 260/45.8 N X |
| 3,920,661 | 11/1975 | Ramey et al. | 260/45.8 N X |
| 3,937,711 | 2/1976 | Cook | 260/45.8 N X |
| B 408,123 | 4/1976 | Randell et al. | 260/45.8 N X |

*Primary Examiner*—Lewis T. Jacobs
*Attorney, Agent, or Firm*—Nestor W. Shust

[57] ABSTRACT

New 1- and 4-substituted piperidines are stabilizers for organic material. They are produced by reacting corresponding 1-substituted piperidinols with acid chlorides or corresponding 4-substituted piperidines with a compound introducing into the 1-position a residue.

16 Claims, No Drawings

PIPERIDINE DERIVATIVES

This is a divisional of application Ser. No. 310,031 filed on Nov. 28, 1972 now abandoned.

The present invention relates to new piperidine derivatives, and in particular to new piperidine derivatives substituted at the 1- and 4- positions and having value as stabilisers for polymeric materials.

In German Patent Specification No. 1,929,928 there are described compounds having the general formula:

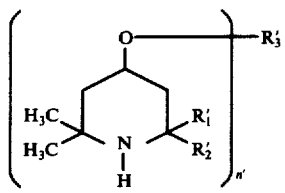

wherein $R_1'$ and $R_2'$ are the same or different and each is an alkyl group, or, together with the carbon atom to which they are bound, they form a saturated alicyclic group or a group having the formula:

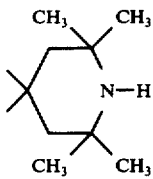

$n'$ is a whole number from 1 to 3 inclusive; and when $n'$ is 1, $R_3$ is an acyl group derived from an aliphatic, alicyclic or heterocyclic mono-carboxylic acid, an N-substituted carbamoyl group derived from an N-substituted carbamic acid, an N-substituted thiocarbamoyl group derived from an N-substituted thiocarbamic acid, a monovalent group obtained by removing an hydroxyl group from an oxo-acid, an alkyl group, a cycloalkyl group, an aralkyl group, an aryl group or a group having the formula:

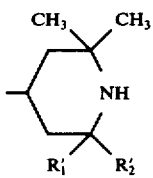

wherein $R_1'$ and $R_2'$ have their previous significance; when $n'$ is 2, $R_2$ is a diacyl group derived from an aliphatic, alicyclic, aromatic or heterocyclic dicarboxylic acid, a dicarbamoyl group derived from a dicarbamic acid, a bis-thiocarbamoyl group derived from a bis-thiocarbamic acid, a carbonyl group, a divalent group obtained by removing two hydroxyl groups from an oxo-acid, an alkylene group, an arylene group, or an arylenedialkylene group; and when $n'$ is 3, $R_3$ is a triacyl group, derived from an aliphatic, alicyclic, aromatic or heterocyclic tricarboxylic acid, a tricarbamoyl group derived from tricarbamic acid, a tris-thiocarbamoyl group derived from a tris-thiocarbamic acid, a trivalent group obtained by removing three hydroxyl groups from an oxo-acid, an alkanetriyl group, arenetriyl group or an arenetriyl trialkylene group.

We have now found that certain piperidine derivatives substituted in the 1- and 4- positions are effective stabilisers for polymers, especially against photo- and thermal degradation.

According to the present invention, there is provided a compound having the formula:

I

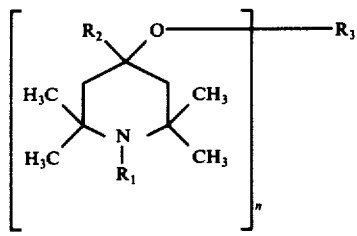

and their salts wherein $n$ is 1, 2, 3 or 4;
$R_1$ is a monovalent residue and is an alkyl residue having from 1 to 20, preferably 1 to 12 carbon atoms, an alkenyl or alkynyl residue having from 3 to 20, preferably 3 to 12 carbon atoms, an aralkyl residue having from 7 to 12 carbon atoms, or a residue having the formula:

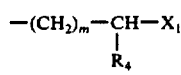

or

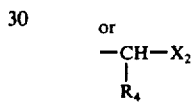

wherein $m$ is 1, 2 or 3,
$R_4$ is hydrogen, methyl or phenyl residue,
$X_2$ is halogen, cyano,

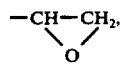

$-COR_5$, $-CO.OR_5$, $-CO.SR_5$, or $-CONR_5R_6$ and $X_1$ is hydroxyl, halogen, cyano,

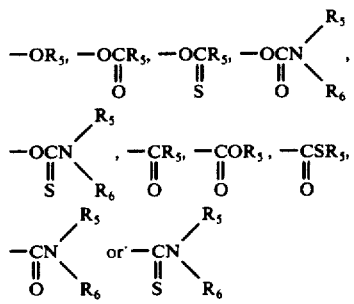

wherein $R_5$ is an alkyl residue having from 1 to 20 carbon atoms, an alkenyl residue having from 2 to 20 carbon atoms, a cycloalkyl residue having from 5 to 12 carbon atoms, an aryl residue having from 6 to 11 carbon atoms, an aryl residue having from 6 to 11 carbon atoms or an aralkyl residue having 7 to 11, preferably 7 to 8 carbon atoms when $R_5$ is joined to a nitrogen atom, also hydrogen and
$R_6$ is preferably hydrogen or an alkyl residue having from 1 to 4 carbon atoms, or $R_5$ and $R_6$ together with the nitrogen atom to which they are bound form a 5- or 6-membered ring which contains no other heteroatoms or contains one or more other heteroatoms, or $R_1$ is an acyl group

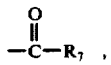

wherein $R_7$ is hydrogen, an unsubstituted aliphatic or substituted aliphatic residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 14 carbon atoms, an aromatic residue having from 6 to 20, preferably 6 to 12, carbon atoms or an heterocyclic residue, or $R_1$ is a carbamoyl or thiocarbamoyl residue having the formula:

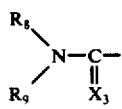

wherein $X_3$ is —O— or —S—, $R_8$ is hydrogen or an alkyl residue having from 1 to 4 carbon atoms, and $R_9$ is hydrogen, an alkyl residue having from 1 to 20 carbon atoms, an alkenyl residue having from 3 to 20 carbon atoms, a cycloalkyl residue having from 5 to 12 carbon atoms or an unsubstituted aryl or substituted aryl residue having from 6 to 12 carbon atoms;

$R_2$ is an alkyl residue having from 1 to 4 carbon atoms, an alkenyl or alkynyl residue having 3 to 20 carbon atoms, preferably 3 or 4 carbon atoms, a cycloalkyl residue having from 5 to 12 carbon atoms, an aryl residue having from 6 to 11 carbon atoms or an aralkyl residue having from 7 to 9 carbon atoms or preferably hydrogen; and when $n$ is 1, $R_3$ is a monovalent radical having the same significance as $R_1$, or $R_3$ represents a monovalent group obtained by removing a hydroxyl group from a sulphinic acid, a sulphonic acid, a phosphorus containing acid or a boric acid, or $R_3$ is an aryl residue, a cycloalkyl group having from 5 to 12 carbon atoms, or a residue having the formula:

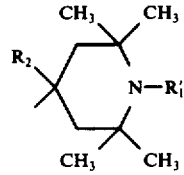

wherein $R_1'$ is hydrogen or $R_1'$ has the same significance as $R_1$.

When $n$ is 2, $R_3$ is a divalent residue and is an alkylene residue having from 1 to 20 carbon atoms, an alkenylene residue having from 2 to 20, preferably 3 to 20, carbon atoms, an alkynylene residue having from 2 to 20, preferably 3 to 20, carbon atoms, cycloalkylidene residue having from 5 to 12 carbon atoms, an arylene residue having 6 to 14 carbon atoms, an aralkylene residue having from 8 to 14 carbon atoms or an aliphatic, aromatic or heterocyclic diacyl residue,

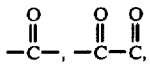

an aliphatic or aromatic dicarbamoyl or dithiocarbamoyl residue, sulphinyl or sulphonyl residue or a divalent residue obtained by removing two hydroxyl groups from a disulphonic acid, a phosphorus containing acid or a boric acid.

When $n$ is 3, $R_3$ is a trivalent residue and is an arenetriyl or an arenetriyl-trialkylene residue, an aliphatic or aromatic triacyl residue or a triacyl residue derived from o-phosphoric, o-phosphorous or o-boric acid; and when $n$ is 4, $R_3$ is a tetravalent residue and is an alkane tetrayl residue, or a tetraacyl residue derived from an aliphatic or aromatic tetracarboxylic acid or from o-silicic acid;

as well as, when $n$ is 2, 3 or 4, partial ethers, esters and carbamoyloxy and thiocarbamoyloxy compounds related to the fully-reacted compounds of formula I.

When $n$ is 1, $R_1$ and/or $R_3$ may be an alkyl residue having from 1 to 20 carbon atoms, preferred 1 to 18, examples of this substituent are methyl, ethyl, n-propyl, n-butyl, sec-butyl, t-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl residue and eicosyl. In terms of accessibility and activity however for optimal compatibility with polyolefines substrates, alkyl substituents $R_1$ and/or $R_3$ having from 5 to 20, especially 5 to 12 carbon atoms are preferred. A sub-group of alkyl residues $R_1$ is that containing from 1 to 4 carbon atoms, preferably methyl.

In those cases in which $R_1$ and/or $R_3$ is an alkenyl residue having from 3 to 20 carbon atoms, examples of these substituents are allyl, methallyl, 3-hexenyl, 4-octenyl, 6-decenyl, 10-undecenyl, and 8-octadecenyl residues, however the preferred substituents in this group are allyl and methallyl residues.

When the residues $R_1$ and/or $R_3$ are alkynyl they may be for example propargyl, but-1- and -2-ynyl, pent-1-ynyl, hex-1-ynyl, oct-1-ynyl, dec-1-ynyl, dodec-1-ynyl, tetradec-1-ynyl and octadec-1-ynyl. The preferred alkynyl substituents however are propargyl and methylpropargyl.

When $R_1$ and/or $R_3$ is an aralkyl residue, suitable examples are benzyl, β-phenethyl, α-methylbenzyl, α,α-dimethylbenzyl, α-naphthylmethyl and p-methyl-α-methylbenzyl residues. Benzyl is preferred.

A further sub-group of $R_1$ and/or $R_3$ substituents is substituted alkyl derivatives having the formula:

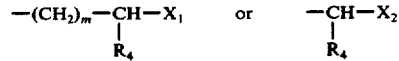

wherein $m$, $R_4$, $X_1$ and $X_2$ have their previous significance, but wherein, however, $R_4$ is preferably hydrogen and $m$ is preferably 1.

When $X_1$ is an hydroxyl residue, examples of this substituents $R_1$ and/or $R_3$ are 2-hydroxyethyl, 2- and 3-hydroxypropyl, 3- and 4-hydroxybutyl, 4-hydroxypentyl and 2-hydroxy-2-phenyl ethyl, preferably 2-hydroxyethyl, 2-hydroxypropyl and 2-hydroxy-2-phenylethyl.

When $X_1$ and/or $X_2$ are halogen atoms, examples of $R_1$ and/or $R_3$ include 2-chloro- and 2-bromo ethyl, 2- and 3-chloro- and 2- and 3-bromopropyl, 3- and 4- chlorobutyl and 2-chloro-2-phenyl ethyl, preferably 2-chloroethyl, 2-chloropropyl and 2-chloro-2-phenylethyl.

When $X_1$ and/or $X_2$ are cyano groups, $R_1$ and/or $R_3$ include cyanomethyl, 1- and 2- cyanobutyl, 4-cyanopentyl, 2-cyano-2-phenylethyl groups, preferably a 2-cyanoethyl group.

When $X_2$ is a 1,2-epoxy group, $R_1$ and/or $R_3$ may be 2,3-epoxy-n-propyl, 2,3-epoxy-methylpropyl, but the preferred epoxyalkyl substituent is 2,3-epoxy-n-propyl.

When $X_1$ is $-OR_5$, $-OCOR_5$, $-OCSR_5$, $-OCONR_6R_5$, $-CSNR_6R_5$, or when $X_1$ and/or $X_2$ are $-COR_5$, $-COOR_5$, $-COSR_5$, $-CONR_6R_5$ and the group $R_5$ is alkyl, then the alkyl group preferably has from 1 to 12, most preferred 1 to 2, carbon atoms; when $R_5$ is an alkenyl residue, then it preferably contains 2 to 4 carbons; when $R_5$ is a cycloalkyl group it preferably contains 6 carbon atoms; when $R_5$ is an aryl residue it preferably contains 6 or 7 carbons; and when $R_5$ is an aralkyl residue, it preferably has 7 or 8 carbon atoms.

$R_5$ and $R_6$ together with the nitrogen atom to which they are bound can form a 5- or 6-membered ring such as the pyrrolidinyl-, imidazolidinyl-, pyrazolidinyl-, piperidinyl-, piperazinyl- or morpholinyl ring.

Examples of $R_1$ and/or $R_3$ within this sub-group are 2-methoxyethyl, 2-ethoxyethyl, 2-propoxyethyl, 2-butoxyethyl, 2-methoxypropyl, 2- and 3-ethoxypropyl, 2- and 3-n-butoxypropyl, 3- and 4-methoxybutyl, 3- and 4-ethoxybutyl, 3- and 4-butoxybutyl, 4-methoxypentyl, 4-ethoxypentyl, 4-n-butoxypentyl, 2-methoxy-2-phenyl ethyl, 2-ethoxy-2-phenyl ethyl; 2-acetoxyethyl, 2-n-propionoxyethyl, 2-benzoyloxy ethyl, 2-acetoxypropyl, 2-n-propionoxypropyl, 4-acetoxybutyl, 4-n-propionoxybutyl, 4-acetoxypentyl, 4-n-propionoxypentyl, 2-phenyl-2-acetoxyethyl, 2-(methylcarbamoyloxy)ethyl, 2-(ethylcarbamoyloxy)ethyl, 2-(phenylcarbamoyloxy)ethyl, 2-(methylcarbamoyloxy)propyl, 2-(ethylcarbamoyloxy)propyl, 2-phenyl-2-(carbamoyloxy)ethyl, 2-(allylthiocarbamoyloxy)ethyl, 2-phenyl-2-(methylcarbamoyloxy)ethyl, 2-phenyl-2-(phenylcarbamoyloxy)ethyl, methylcarbonylmethyl, 2-(methylcarbonyl)ethyl, 2-(ethyl-carbonyl) ethyl, 2-(methylcarbonyl)propyl, and 2-(methylcarbonyl)-2-phenyl ethyl; methoxycarbonyl methyl, 2-(ethoxycarbonyl) ethyl, 2-(methoxycarbonyl)-propyl, and 2-(methoxycarbonyl)-2-phenylethyl, 2-(ethylthiocarbonyl)ethyl, 2-(methylthiocarbonyl)propyl and 2-(methylthiocarbonyl)-2-phenylethyl; carbamoylmethyl, 2-carbamoylethyl, 2-methylcarbamoylethyl, 2-ethylcarbamoylethyl, dimethylcarbamoylmethyl, 2-diethylcarbamoylethyl, thiocarbamoylmethyl, 2-(thiocarbamoyl)ethyl, 2-methylthiocarbamoylethyl, dimethylthiocarbamoylmethyl, 2-(phenylcarbamoyl)ethyl.

When $n$ is 1 and $R_1$ and/or $R_3$ is an acyl group $-COR_7$ wherein $R_7$ is an unsubstituted aliphatic or substituted aliphatic residue having from 1 to 20, preferably 1 to 19, carbon atoms, $R_7$ may be a methyl, ethyl, propyl, butyl, hexyl, n-octyl, 2-ethylhexyl, n-decyl, n-undecyl, n-tridecyl, n-tetradecyl, n-hexadecyl, n-heptadecyl and eicosyl, chloroethyl, chlorohexyl, methylthioethyl, ethylthioethyl, octylthioethyl, or dodecylthioethyl residue; alkenyl residues $R_7$ have from 2 to 20, preferably 2 to 17, most preferred 2 to 6, carbon atoms such as vinyl, allyl, methallyl, isobutenyl or hexenyl group; alkynyl residues $R_7$ have from 2 to 20, preferably 2 to 6, carbon atoms such as a propargyl group; cycloaliphatic residues $R_7$ have from 5 to 12, preferably 6 to 10, most preferred 6, carbon atoms such as a cyclopentyl or cyclohexyl residue; araliphatic residues $R_7$ have from 7 to 14, preferably 7 to 13, most preferred 7 to 9, carbon atoms such as a benzyl, β-phenylethyl, diphenylmethyl or styryl residue; unsubstituted aromatic residues $R_7$ have from 6 to 14, preferably 6 to 10, carbon atoms such as a phenyl or naphthyl residue, a substituted aromatic residue, substituted by for example alkyl having 1 to 4 carbon atoms such as tolyl, p-tert-butylphenyl; and heterocyclic residues $R_7$ may be a furan or thiophene residue. Examples of compounds wherein $R_1$ and/or $R_3$ are unsaturated acyl groups are preferred those wherein only one of $R_1$ and $R_3$ denotes an unsaturated acyl group.

Examples of acyl groups $R_1$ and/or $R_3$ are formyl, acetyl, propionyl, n-butyryl, hexanoyl, heptanoyl, octanoyl, 2-ethylhexanoyl, 2,2,4-trimethylpentanoyl, n-decanoyl, n-dodecanoyl, n-tetradecanoyl, n-hexadecanoyl, n-octadecanoyl, n-eicosoyl, acryloxyl, α-methacrylol, crotonoyl, undec-10-enoyl, octadec-9-enoyl, β-methylthiopropionyl, methylthioacetyl, β-octylthiopropionyl, β-dodecylthiopropionyl, cyclopentanoyl, cyclohexanoyl, benzoyl, α- and β-naphthoyl, cyclopentylacetyl, cyclohexylacetyl, phenylacetyl, β-phenylpropionyl, diphenyloctyl, β-phenylacryloyl, o-, m- and p-toluoyl, o-, m- or p-methoxybenzoyl and o-, m- and p-chlorobenzoyl, 2-furoyl and 2-picolinoyl.

When $n$ is 1, $R_1$ and/or $R_3$ may also be a carbamoyl or thiocarbamoyl residue having the formula:

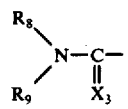

wherein $X_3$ is $-O-$ or $-S-$, $R_8$ is hydrogen or an alkyl residue having from 1 to 4 carbon atoms and $R_9$ is hydrogen, an alkyl residue having from 1 to 20, preferably 1 to 8, carbon atoms, an alkenyl residue having from 3 to 20 carbon atoms, a cycloalkyl residue having from 5 to 12 carbon atoms or an unsubstituted alkyl, or substituted aryl, for instance, alkyl or halogen-substituted aryl residue having from 6 to 12, preferably 6 to 10, carbon atoms. Examples of suitable residues within this group are carbamoyl, N-methylcarbamoyl, N-ethyl-carbamoyl, N-n-propylcarbamoyl, N-isopropylcarbamoyl, N-n-butylcarbamoyl, N-n-pentylcarbamoyl, N-n-octylcarbamoyl, N-n-decylcarbamoyl, N-n-dodecylcarbamoyl, N-n-octadecyl, N-n-eicosylcarbamoyl, N-allylcarbamoyl, N-methallylcarbamoyl, N-undecenylcarbamoyl, N-cyclopentylcarbamoyl, N-cyclohexylcarbamoyl, N-methylcyclohexylcarbamoyl, N-cyclododecylcarbamoyl, N-(1- and 2-perhydronaphthyl)carbamoyl, N-adamantylcarbamoyl, N-cyclopentylmethylcarbamoyl, N-benzylcarbamoyl, N-(β-phenethyl)carbamoyl, N-(1- and 2-naphthylmethyl)carbamoyl, N-phenylcarbamoyl, N-(o-, m- and p-tolyl)carbamoyl, N-(2,4- and 2,6-xylyl)carbamoyl, N-(α-and β-naphthyl)carbamoyl, N,N-dimethylcarbamoyl, N-methyl, N-ethylcarbamoyl, N,N-diethylcarbamoyl, N,N-diisopropylcarbamoyl, N,N-di-n-propylcarbamoyl, N,N-di-n-butyl-carbamoyl and N,N-di-isobutyl-carbamoyl residues as well as the corresponding thiocarbamoyl residues.

When $R_2$ is an alkyl residue it is for example methyl, ethyl, n-propyl, isopropyl, n-butyl, isobutyl, t-butyl, preferably methyl, as alkenyl residue $R_2$ is for example allyl, methallyl, 3-hexenyl, 4-octenyl, 6-decenyl, 10- undecenyl or 8-octadecenyl, preferably allyl or methallyl and as alkynyl residue for example propargyl, but-1- and -2-ynyl, penta-1-ynyl, hex-1-ynyl, oct-1-ynyl, dec-1-ynyl, dodec-1-ynyl, tetradec-1-ynyl and octadec-1-ynyl, preferably propargyl, $R_2$ as cycloalkyl is for example cyclopentyl, cyclohexyl, cyclooctyl, cyclododecyl, preferably cyclohexyl as aryl residue $R_2$ is for example phenyl, p-tolyl, t-butylphenyl, naphthyl, preferably phenyl or p-tolyl and as aralkyl residue it is for example benzyl, alpha-methylbenzyl, p,alpha-dimethylbenzyl, preferably benzyl.

When $n$ is 1

$R_3$ may be the same as $R_1$. If $R_3$ is alkyl it is preferably an alkyl group having from 3 to 18 carbon atoms.

When $R_3$ represents an aryl residue it is for example an aromatic residue having 6 to 20 carbon atoms, preferably an aryl residue having 6 to 12 carbon atoms, most preferred phenyl.

When $n$ is 2

$R_3$ is, for example an alkylene residue having from 1 to 20, preferably 2 to 6, carbon atoms such as methylene, ethylene, trimethylene, tetramethylene or hexamethylene residue. Alkenylene residues $R_3$ preferably contain 3 to 20, most preferred 3 or 4 carbons, and may be, for instance a 1,3-propen-ene or 1,4-buten-2-ene residue. Alkynylene residues $R_3$ preferably contain 3 to 20, most preferred 4 carbon atoms and may be, for instance a 1:4 but-2-ynylene residue. When $R_3$ is a cycloalkylidene residue, it preferably contains 7 or 8 carbon atoms, for instance a cyclohexyldimethylene residue.

When $R_3$ is arylene it has preferably 6 to 12 carbon atoms and it may be for example 1,3-phenylene, or 4,4'-diphenylene.

When $R_3$ is aralkylene it may be for example α,α-p-xylylene.

Diacyl residues $R_3$ include those derived from an aliphatic, aromatic or heterocyclic dicarboxylic acid. Examples of aliphatic dicarboxylic acids are those having from 2 to 20, preferably alkan dicarboxylic acids having 6 to 10 carbon atoms such as malonic, succinic, glutaric, adipic, pimelic, suberic, azelaic, sebacic, 1,12-dodecanedioic, 1,18-octadecanedioic, 1,20-docosanedioic acid and N-methyliminodiacetic acid. Examples of aromatic diacyl residues are those derived from phthalic, isophthalic and terephthalic acids, each optionally ring-substituted, for instance by halogen, an alkyl or alkoxy group each having from 1 to 20 carbon atoms, a hydroxy or tertiary amino group.

Examples of heterocyclic dicarboxylic acids are 2,5-thiophene dicarboxylic acid or 2,5-furandicarboxylic acid.

$R_3$ is for example an aliphatic or aromatic dicarbamoyl residue such as a divalent alkyl dicarbamoyl residue for example the divalent residue of butan-1,4-dicarbamoyl or hexan-1,6-dicarbamoyl or such as a divalent aryl dicarbamoyl residue such as the divalent residue of phenyl-1,4-dicarbamoyl. $R_3$ is for example an aliphatic or aromatic dithiocarbamoyl residue such as a divalent alkyl dithiocarbamoyl residue for example the divalent residue of butan-1,4-dithiocarbamoyl or hexan-1,6-dithiocarbamoyl or such as an divalent aryl dithiocarbamoyl residue such as the divalent residue of phenyl-1,4-dithiocarbamoyl.

When $n$ is 3

$R_3$ is, for instance, a triacyl group derived from an aliphatic tricarboxylic acid such as nitrilotriacetic acid, tricarballylic acid, from an aromatic tricarboxylic acid such as benzene tricarboxylic acid or from an inorganic acid such as o-phosphorous, o-phosphoric or o-boric acid, or oxyacids, for example, benzene-1,3,5-trisulphonic acid.

When $n$ is 4

$R_3$ is, for instance, a tetracyl group derived from a tetracarboxylic acid, such as ethylene diamine, tetracarboxylic acid, from the tetracarboxylic acids described in British Pat. Spec. No. 1,080,336, 1,2,4,5-benzene tetracarboxylic acid or from o-silicic acid.

$R_3$ preferably represents an acyl or an N- substituted carbamoyl, an alkylene group, a substituted alkylene or an aralkyl group.

$R_1$ preferably represents an alkyl, alkenyl, or substituted alkyl group such as hydroxyalkyl, alkylcarbonyloxy or aralkyl group.

Examples of compounds of the present invention are:

Examples where $n = 1$

4-Methoxy-1,2,2,6,6-pentamethylpiperidine
4-n-Butoxy-1,2,2,6,6-pentamethylpiperidine
4-n-Dodecyloxy-1,2,2,6,6-pentamethylpiperidine
4-n-Octadecyloxy-1,2,2,6,6-pentamethylpiperidine
4-(2'-Cyanoethoxy)-1,2,2,6,6-pentamethylpiperidine
4-(2'-Hydroxyethoxy)-1,2,2,6,6-pentamethylpiperidine
1-n-Propyl-4-methoxy-2,2,6,6-tetramethylpiperidine
1-n-Propyl-4-n-dodecyloxy-2,2,6,6-tetramethylpiperidine
1-n-Propyl-4-n-octadecyloxy-2,2,6,6-tetramethylpiperidine
1-sec-Butyl-4-n-dodecyloxy-2,2,6,6-tetramethylpiperidine
1-n-Octyl-4-methoxy-2,2,6,6-tetramethylpiperidine
1n-Dodecyl-4-n-dodecyloxy-2,2,6,6-tetramethylpiperidine
1-n-Octadecyl-4-methoxy-2,2,6,6-tetramethylpiperidine
1-n-Octadecyl-4-n-octadecyloxy-2,2,6,6-tetramethylpiperidine
1-Eicosyl-4-methoxy-2,2,6,6-tetramethylpiperidine
1-Allyl-4-methoxy-2,2,6,6-tetramethylpiperidine
1-Allyl-4-allyloxy-2,2,6,6-tetramethylpiperidine
1-(1'-Undec-10'-enyl)-4-n-butoxy-2,2,6,6-tetramethylpiperidine
1-(1'-Undec-10'-enyl)-4-(1'-undec-10'-enyloxy)-2,2,6,6tetramethylpiperidine
1-Oleyl-4-methoxy-2,2,6,6-tetramethylpiperidine
1-Oleyl-4-oleyloxy-2,2,6,6-tetramethylpiperidine
1-Propargyl-4-ethoxy-2,2,6,6-tetramethylpiperidine
1-Propargyl-4-propargyloxy-2,2,6,6-tetramethylpiperidine
1-Benzyl-4-n-dodecyloxy-2,2,6,6-tetramethylpiperidine
1-Benzyl-4-allyloxy-2,2,6,6-tetramethylpiperidine
1-Benzyl-4-propargyloxy-2,2,6,6-tetramethylpiperidine
1-Benzyl-4-benzyloxy-2,2,6,6-tetramethylpiperidine
1-(2'-Hydroxyethyl)-4-methoxy-2,2,6,6-tetramethylpiperidine
1-(2'-Hydroxypropyl)-4-allyloxy-2,2,6,6-tetramethylpiperidine
1-(2'-Hydroxyethyl)-4-propargyloxy-2,2,6,6-tetramethylpiperidine
1-(2'-Hydroxypropyl)-4-benzyloxy-2,2,6,6-tetramethylpiperidine 1-(2'-Hydroxyethyl)-4-(2'-hydroxyethoxy)-2,2,6,6-tetramethylpiperidine
1-(2'-Hydroxypropyl)-4-(2'-hydroxypropoxy)-2,2,6,6-tetramethylpiperidine
1-(2'-Hydroxy-2'-phenylethyl)-4-n-butoxy-2,2,6,6-tetramethylpiperidine
1(2'-Hydroxy-2'-phenylethyl)-4-(2'-hydroxy-2'-phenylethoxy)2,2,6,6-tetramethylpiperidine
1-(2'-Chloroethyl)-4-n-dodecyloxy-2,2,6,6-methylpiperidine
1-(2'-Chloropropyl)4-benzyloxy-2,2,6,6-tetramethylpiperidine
1-(2'-Bromoethyl)-4-(2'-bromoethoxy)2,2,6,6-tetramethylpiperidine
1-(2'-Chloro-2'-phenylethyl)-4-n-octyloxy-2,2,6,6-tetramethylpiperidine
1-(2'-Cyanoethyl)-4-phenoxy-2,2,6,6-tetramethylpiperidine
1-(2'-Cyanoethyl)-4-benzyloxy-2,2,6,6-tetramethylpiperidine
1-(2'-Cyanoethyl)-4-(2'-cyanoethoxy)-2,2,6,6-tetramethylpiperidine
1-(2'-Cyanopropyl)-4-methoxy-2,2,6,6-tetramethylpiperidine
1-(2',3'-epoxypropyl)-4-n-butoxy-2,2,6,6-tetramethylpiperidine
1-(2',3'-epoxypropyl)-4-benzyloxy-2,2,6,6-tetramethylpiperidine
1-(2',3'-epoxypropyl)-4-(2',3'-epoxypropoxy)-2,2,6,6-tetramethylpiperidine
1-(2'-methoxyethyl)-4-ethoxy-2,2,6,6-tetramethylpiperidine
1(2'-methoxyethyl)-4-(2'-methoxyethoxy)-2,2,6,6-tetramethylpiperidine
1-(2'-ethoxypropyl)-4-allyloxy-2,2,6,6-tetramethylpiperidine
1-(2'-ethoxy-2'-phenylethyl)-4-benzyloxy-2,2,6,6-tetramethylpiperidine
1-(2'-acetoxyethyl)-4-n-butoxy-2,2,6,6-tetramethylpiperidine
1-(2'-benzoyloxyethyl)-4-(2'-benzoyloxyethoxy)-2,2,6,6-tetramethylpiperidine
1-(2'-propionoxypropyl)-4-allyloxy-2,2,6,6-tetramethylpiperidine
1-[2'-(methylcarbamoyloxy)ethyl]-4-benzyloxy-2,2,6,6-tetramethylpiperidine
1-[2'-(methylcarbamoyloxy)ethyl]-4-[2'-(methylcarbamoyloxy)ethoxy]-2,2,6,6-tetramethylpiperidine
1-[2'-(Phenylcarbamoyloxy)ethyl]-4-(2'-cyanoethoxy)-2,2,6,6-tetramethylpiperidine
1-[2'-(ethylthiocarbamoyloxy)ethyl]-4-[2'-(ethylthiocarbamoyloxy)ethoxy]-2,2,6,6-tetramethylpiperidine
1-Methylcarbonylmethyl-4-methoxy-2,2,6,6-tetramethylpiperidine
1-[(methylcarbonyl)ethyl]-4-n-octyloxy-2,2,6,6-tetramethylpiperidine
1-Methylcarbonylmethyl-4-methylcarbonylmethoxy-2,2,6,6-tetramethylpiperidine
1-(2'-methoxycarbonylethyl)-4-(2'-methoxycarbonylethoxy)-2,2,6,6-tetramethylpiperidine
1-(2'-methoxycarbonylethyl)-4-ethoxy-2,2,6,6-tetramethylpiperidine
1-[2'-(ethoxycarbonyl)ethyl]-4-(2'-hydroxyethoxy)-2,2,6,6-tetramethylpiperidine
1-[2'-(thioethoxycarbonyl)ethyl]-4-methoxy-2,2,6,6-tetramethylpiperidine
1-Carbamoylmethyl-4-benzyloxy-2,2,6,6-tetramethylpiperidine
1-(2'-carbamoylethyl)-4-dodecoxy-2,2,6,6-tetramethylpiperidine
1-[2'-(Methylcarbamoyl)ethyl]-4-[2'-methylcarbamoylethoxy]-2,2,6,6-tetramethylpiperidine
1-[2'-(Diethylcarbamoyl)ethyl]-4-methoxy-2,2,6,6-tetramethylpiperidine
1-Thiocarbamoylmethyl-4-allyloxy-2,2,6,6-tetramethylpiperidine
1-(Dimethylthiocarbamoyl)methyl-4-benzyloxy-2,2,6,6-tetramethylpiperidine
1-Acetyl-4-benzyloxy-2,2,6,6-tetramethylpiperidine
1-Lauroyl-4-(2'-hydroxyethoxy)-2,2,6,6-tetramethylpiperidine
1-Stearoyl-4-methoxy-2,2,6,6-tetramethylpiperidine
1-Benzoyl-4-n-butoxy-2,2,6,6-tetramethylpiperidine
1-Carbamoyl-4-n-octadecyloxy-2,2,6,6-tetramethylpiperidine
1-Methylcarbamoyl-4-benzyloxy-2,2,6,6-tetramethylpiperidine
1-Phenylcarbamoyl-4-(2'-hydroxyethoxy)-2,2,6,6-tetramethylpiperidine
1-Phenylthiocarbamoyl-4-(cyclohexyloxy)-2,2,6,6-tetramethylpiperidine
1-Dimethylcarbamoyl-4-methoxy-2,2,6,6-tetramethylpiperidine
1-Methylthiocarbamoyl-4-n-octyloxy-2,2,6,6-tetramethylpiperidine
1-Phenylthiocarbamoyl-4-methoxy-2,2,6,6-tetramethylpiperidine
1,2,2,6,6-Pentamethylpiperidinyl-4-formate
1,2,2,6,6-Pentamethylpiperidinyl-4-acetate
1,2,2,6,6-Pentamethylpiperidinyl-4-isobutyrate
1,2,2,6,6-Pentamethylpiperidinyl-4-n-octanoate
1,2,2,6,6-Pentamethylpiperidinyl-4-pivalate
1,2,2,6,6-Pentamethylpiperidinyl-4-stearate
1,2,2,6,6-Pentamethylpiperidinyl-4-cicosanoate
1,2,2,6,6-Pentamethylpiperidinyl-4-(2'-ethylhexanoate)
1,2,2,6,6-Pentamethylpiperidinyl-4-acrylate
1,2,2,6,6-Pentamethylpiperidinyl-4-oleate
1,2,2,6,6-Pentamethylpiperidinyl-4-cyclohexanecarboxylate
1,2,2,6,6-Pentamethylpiperidinyl-4-adamantane-1-carboxylate
1,2,2,6,6-Pentamethylpiperidinyl-4-benzoate
1,2,2,6,6-Pentamethylpiperidinyl-4-p-toluate
1,2,2,6,6-Pentamethylpiperidinyl-4-p-t-butylbenzoate
1,2,2,6,6-Pentamethylpiperidinyl-4-p-methoxybenzoate
1,2,2,6,6-Pentamethylpiperidinyl-4-o-chloro-benzoate
1,2,2,6,6-Pentamethylpiperidinyl-4-p-chloro-benzoate
1,2,2,6,6-Pentamethylpiperidinyl-4-α-naphthoate
1,2,2,6,6-Pentamethylpiperidinyl-4-phenylacetate
1,2,2,6,6-Pentamethylpiperidinyl-4-(1'-naphthylacetate)
1,2,2,6,6-Pentamethylpiperidinyl-4-cinnamate
1,2,2,6,6-Pentamethylpiperidinyl-4-diphenylacetate
1,2,2,6,6-Pentamethylpiperidinyl-4-n-dodecylthioacetate
1,2,2,6,6-Pentamethylpiperidinyl-4-(furan-2'-carboxylate)
1,2,2,6,6-Pentamethylpiperidinyl-dimethyl trimesate
1-n-Propyl-2,2,6,6-tetramethylpiperidinyl-acetate
1-n-Propyl-2,2,6,6-tetramethylpiperidinyl-4-octanoate
1-n-Propyl-2,2,6,6-tetramethylpiperidinyl-4-stearate
1-n-Octyl-2,2,6,6-tetramethylpiperidinyl-4-benzoate
1-n-Dodecyl-2,2,6,6-tetramethylpiperidinyl-4-n-octanoate
1-n-Dodecyl-2,2,6,6-tetramethylpiperidinyl-4-p-chlorobenzoate 1-n-Octadecyl-2,2,6,6-tetramethylpiperidinyl-4-benzoate
1-Allyl-2,2,6,6-tetramethylpiperidinyl-4-n-octanoate
1-Allyl-2,2,6,6-tetramethylpiperidinyl-4-cyclohexanecarboxylate
1-Allyl-2,2,6,6-tetramethylpiperidinyl-4-benzoate
1-α-Methallyl-2,2,6,6-tetramethylpiperidinyl-4-acetate
1-Oleyl-2,2,6,6-tetramethylpiperidinyl-4-cyclohexanecarboxylate
1-Propargyl-2,2,6,6-tetramethylpiperidinyl-4-p-methoxybenzoate
1-Benzyl-2,2,6,6-tetramethylpiperidinyl-4-n-octanoate
1-Benzyl-2,2,6,6-tetramethylpiperidinyl-4-(2'-ethylhexanoate)
1-Benzyl-2,2,6,6-tetramethylpiperidinyl-4-stearate
1-Benzyl-2,2,6,6-tetramethylpiperidinol-4-benzoate
1-(2'-Hydroxyethyl)-2,2,6,6-tetramethylpiperidinyl-4-acetate
1-(2'-Hydroxyethyl)-2,2,6,6-tetramethylpiperidinyl-4-laurate
1(2'-Hydroxyethyl)-2,2,6,6-tetramethylpiperidinyl-4-stearate
1-(2'-Hydroxyethyl)-2,2,6,6-tetramethylpiperidinyl-4-benzoate
1-(2'-Hydroxypropyl)-2,2,6,6-tetramethylpiperidinyl-4-oleate
1-(2'-Hydroxy-2'-phenylethyl)-2,2,6,6-tetramethylpiperidinyl-4-phenylacetate
1-(2'-Chloroethyl)-2,2,6,6-tetramethylpiperidinyl-4-n-octanoate
1-(2'-Bromopropyl)-2,2,6,6-tetramethylpiperidinyl-4-cyclohexane-carboxylate
1-(2'-Chloro-2'-phenylethyl)-2,2,6,6-tetramethylpiperidinyl-4-p-methoxybenzoate
1-(2'-Cyanoethyl)-2,2,6,6-tetramethylpiperidinyl-4-benzoate
1-(2'-Cyanopropyl)-2,2,6,6-tetramethylpiperidinyl-4-p-chlorobenzoate
1-(2',3'-epoxypropyl)-2,2,6,6-tetramethylpiperidinyl-4-acetate
1-(2'-ethoxypropyl)-2,2,6,6-tetramethylpiperidinyl-4-(2'-ethylhexanoate)
1-(2'-ethoxy-2'-phenylethyl)-2,2,6,6-tetramethylpiperidinyl-4-diphenylacetate
1-(2'-acetoxyethyl)-2,2,6,6-tetramethylpiperidinyl-4-laurate
1-[2'-(methylcarbamoyloxy)ethyl]-2,2,6,6-tetramethylpiperidinyl-4-benzoate
1-[2'-(phenylcarbamoyloxy)ethyl]-2,2,6,6-tetramethylpiperidinyl-4-isobutyrate
1-[2'-(ethylthiocarbamoyloxy)ethyl]-2,2,6,6-tetramethylpiperidinyl-4-pivalate
1-Methylcarbonylmethyl-2,2,6,6-tetramethylpiperidinyl-4-phenylacetate
1-[2'-(methylcarbonyl)ethyl]-2,2,6,6-tetramethylpiperidinyl-4-acetate
1-Ethoxycarbonylmethyl-2,2,6,6-tetramethylpiperidinyl-4-p-methoxybenzoate
1-[2'-(Methoxycarbonyl)ethyl]-2,2,6,6-tetramethylpiperidinyl-4-p-toluate
1-Carbamoylmethyl-2,2,6,6-tetramethylpiperidinyl-4-p-methoxybenzoate
1-(2'-Carbamoylethyl)-2,2,6,6-tetramethylpiperidinyl-4-stearate
1-[2'-(methylcarbamoyl)ethyl]-2,2,6,6-tetramethylpiperidinyl-4-octanoate
1-(Dimethylthiocarbamoyl)methyl-2,2,6,6-tetramethylpiperidinyl-4-isobutyrate
1-Acetyl-2,2,6,6-tetramethylpiperidinyl-4-acetate
1-Acetyl-2,2,6,6-tetramethylpiperidinyl-4-(2'-ethylhexanoate)
1-Acetyl-2,2,6,6-tetramethylpiperidinyl-4-stearate
1-Isobutyryl-2,2,6,6-tetramethylpiperidinyl-4-n-octanoate
1-Lauroyl-2,2,6,6-tetramethylpiperidinyl-4-eicosanoate
1-Stearoyl-2,2,6,6-tetramethylpiperidinyl-4-acetate
1-Benzoyl-2,2,6,6-tetramethylpiperidinyl-4-benzoate
1-Carbamoyl-2,2,6,6-tetramethylpiperidinyl-4-(1'-naphthylacetate)
1-Methylcarbamoyl-2,2,6,6-tetramethylpiperidinyl-4-n-octanoate
1-Phenylcarbamoyl-2,2,6,6-tetramethylpiperidinyl-4-phenylacetate
1-Dimethylcarbamoyl-2,2,6,6-tetramethylpiperidinyl-4-laurate
1-Phenylthiocarbamoyl-2,2,6,6-tetramethylpiperidinyl-4-p-t-butylbenzoate
4-carbamoyloxy-1,2,2,6,6-pentamethylpiperidine
4-methylcarbamoyloxy-1,2,2,6,6-pentamethylpiperidine
4-dimethylcarbamoyloxy-1,2,2,6,6-pentamethylpiperidine
4-isopropylcarbamoyloxy-1,2,2,6,6-pentamethylpiperidine
4-t-butylcarbamoyloxy-1,2,2,6,6-pentamethylpiperidine
4-n-hexylcarbamoyloxy-1,2,2,6,6-pentamethylpiperidine
4-[2'-ethylhexylcarbamoyloxy]-1,2,2,6,6-pentamethylpiperidine
4-n-dodecylcarbamoyloxy-1,2,2,6,6-pentamethylpiperidine
4-n-octadecylcarbamoyloxy-1,2,2,6,6-pentamethylpiperidine
4-allylcarbamoyloxy-1,2,2,6,6-pentamethylpiperidine
4-oleylcarbamoyloxy-1,2,2,6,6-pentamethylpiperidine
4-cyclohexylcarbamoyloxy-1,2,2,6,6-pentamethylpiperidine
4-[3'-methylcyclohexylcarbamoyloxy]-1,2,2,6,6-pentamethylpiperidine
4-[4'-t-butylcyclohexylcarbamoyloxy]-1,2,2,6,6-pentamethylpiperidine
4-cyclohexylmethylcarbamoyloxy-1,2,2,6,6-pentamethylpiperidine
4-benzylcarbamoyloxy-1,2,2,6,6-pentamethylpiperidine
4-phenylcarbamoyloxy-1,2,2,6,6-pentamethylpiperidine
4-phenylthiocarbamoyloxy-1,2,2,6,6-pentamethylpiperidine
4-m-tolylcarbamoyloxy-1,2,2,6,6-pentamethylpiperidine
4-p-tolylcarbamoyloxy-1,2,2,6,6-pentamethylpiperidine
4-p-chlorophenylcarbamoyloxy-1,2,2,6,6-pentamethylpiperidine
4-p-t-butylphenylcarbamoyloxy-1,2,2,6,6-pentamethylpiperidine
4-α-naphthylcarbamoyloxy-1,2,2,6,6-pentamethylpiperidine
4-cyclohexylcarbamoyloxy-1-ethyl-2,2,6,6-tetramethylpiperidine
4-methylcarbamoyloxy-1-n-propyl-2,2,6,6-tetramethylpiperidine
4-methylcarbamoyloxy-1-secbutyl-2,2,6,6-tetramethylpiperidine
4-n-octadecylcarbamoyloxy-1-n-butyl-2,2,6,6-tetramethylpiperidine
4-Methylcarbamoyloxy-1-n-octyl-2,2,6,6-tetramethylpiperidine 4-methylcarbamoyloxy-1-n-octadecyl-2,2,6,6-tetramethylpiperidine
4-phenylcarbamoyloxy-1-allyl-2,2,6,6-tetramethylpiperidine
4-p-tolylcarbamoyloxy-1-oleyl-2,2,6,6-tetramethylpiperidine
4-methylcarbamoyloxy-1-propargyl-2,2,6,6-tetramethylpiperidine
4-phenylcarbamoyloxy-1-benzyl-2,2,6,6-tetramethylpiperidine
4-methylcarbamoyloxy-1-(2'-hydroxyethyl)-2,2,6,6-tetramethylpiperidine
4-cyclohexylcarbamoyloxy-1-(2'-chloropropyl)-2,2,6,6-tetramethylpiperidine
4-phenylcarbamoyloxy-1-(2'-hydroxy-2'-phenylethyl)-2,2,6,6-tetramethylpiperidine
4-methylcarbamoyloxy-1-(2',3'-epoxypropyl)-2,2,6,6-tetramethylpiperidine
4-carbamoyloxy-1-(2'-methoxyethyl)-2,2,6,6-tetramethylpiperidine
4-dimethylcarbamoyloxy-1-(2'-acetoxyethyl)-2,2,6,6-tetramethylpiperidine
4-n-hexylcarbamoyloxy-1-[2'-(methylcarbamoyloxy)ethyl]-2,2,6,6-tetramethylpiperidine
4-methylcarbamoyloxy-1-methylcarbonylmethyl-2,2,6,6-tetramethylpiperidine
4-phenylcarbamoyl-1-(2'-methylcarbonylethyl)-2,2,6,6-tetramethylpiperidine
4-benzylcarbamoyloxy-1-carbamoylmethyl-2,2,6,6-tetramethylpiperidine
4-n-dodecylcarbamoyloxy-1-(2'-carbamoylethyl)-2,2,6,6-tetramethylpiperidine
4-methylcarbamoyloxy-1-(2'-thiocarbamoylethyl)-2,2,6,6-tetramethylpiperidine
4-methylcarbamoyloxy-1-acetyl-2,2,6,6-tetramethylpiperidine
4-phenylcarbamoyloxy-1-stearoyl-2,2,6,6-tetramethylpiperidine
4-methylthiocarbamoyloxy-1-lauroyl-2,2,6,6-tetramethylpiperidine
4-[2'-ethylhexylcarbamoyl]-1-benzoyl-2,2,6,6-tetramethylpiperidine
4-carbamoyloxy-1-carbamoyl-2,2,6,6-tetramethylpiperidine
4-methylcarbamoyloxy-1-methylcarbamoyl-2,2,6,6-tetramethylpiperidine
4-phenylcarbamoyloxy-1-phenylcarbamoyl-2,2,6,6-tetramethylpiperidine
4-methylthiocarbamoyloxy-1-methylthiocarbamoyl-2,2,6,6-tetramethylpiperidine
4-phenylthiocarbamoyloxy-1-phenylthiocarbamoyl-2,2,6,6-tetramethylpiperidine
4-dimethylcarbamoyloxy-1-dimethylcarbamoyl-2,2,6,6-tetramethylpiperidine
4-stearyloxy-1,2,2,4,6,6-hexamethylpiperidine
4-phenyl-1,2,2,6,6-pentamethyl-piperidinyl-4-n-octanoate Examples where n = 2

1,2-Bis(1',2',2', 6', 6'-pentamethyl-4'-piperidyloxy)ethane
1,4-Bis(1'-n-propyl-2',2',6',6'-tetramethyl-4'-piperidyloxy)butene
1,6-Bis(1'-n-octadecyl-2',2',6',6'-tetramethyl-4'-piperdidyloxy)hexane
1,4-Bis(1'-allyl-2',2',6',6'-tetramethyl-4'-piperidyloxy)cyclohexane
1,4-Bis(1'-propargyl-2',2',6',6'-tetramethyl-4-piperidyloxy)but-2-ene
α,α-Bis(1-benzyl-2,2,6,6-tetramethyl-4-piperidyloxy)p-xylene
1,3-Bis[1'-(2''-hydroxyethyl)-2',2',6',6'-tetramethyl-4'-piperidyloxy]benzene
1,2-Bis[1'-(2''-cyanoethyl)-2',2',6',6'-tetramethyl-4'-piperidyloxy]ethane
1,4-Bis(1'-acetyl-2',2',6',6'-tetramethyl-4'-piperidyloxy)but-2-yne
4,4-Bis(1''-methylcarbamoyl-2'',2'',6'',6''-tetramethyl-4''-piperidyloxy)diphenylmethane
Bis(1,2,2,6,6-pentamethyl-4-piperidinyl)carbonate
Bis(1,2,2,6,6-pentamethyl-4-piperidinyl)oxalate
Bis(1,2,2,6,6-pentamethyl-4-piperidinyl)malonate
Bis(1,2,2,6,6-pentamethyl-4-piperidinyl)adipate
Bis(1,2,2,6,6-pentamethyl-4-piperidinyl)sebacate
Bis(1,2,2,6,6-pentamethyl-4-piperidinyl)fumarate
Bis(1,2,2,6,6-pentamethyl-4-piperidinyl)isophtalate
Bis(1,2,2,6,6-pentamethyl-4-piperidinyl)cyclohexane 1',4'-dicarboxylate
Bis(1,2,2,6,6-pentamethyl-4-piperidinyl)thiodipropionate
Bis(1,2,2,6,6-pentamethyl-4-piperidinyl)methyltrimesate
Bis(1-n-propyl-2,2,6,6-tetramethyl-4-piperidinyl)adipate
Bis(1-secbutyl-2,2,6,6-tetramethyl-4-piperidinyl)succinate
Bis(1-n-octyl-2,2,6,6-tetramethyl-4-piperidinyl)sebacate
Bis-(1-n-dodecyl-2,2,6,6-tetramethyl-4-piperidinyl)adipate
Bis(1-n-octadecyl-2,2,6,6-tetramethyl-4-piperidinyl)sebacate
Bis(1-allyl-2,2,6,6-tetramethyl-4-piperidinyl)adipate
Bis(1-allyl-2,2,6,6-tetramethyl-4-piperidinyl)thiophene-2',5'-dicarboxylate
Bis(1-oleyl-2,2,6,6-tetramethyl-4-piperidinyl)thiodipropionate
Bis(1-propargyl-2,2,6,6-tetramethyl-4-piperidinyl)sebacate
Bis(1-benzyl-2,2,6,6-tetramethyl-4-piperidinyl)sebacate
Bis[1-(2'-hydroxyethyl)-2,2,6,6-tetramethyl-4-piperidinyl]adipate
Bis[1-(2'-chloropropyl)-2,2,6,6-tetramethyl-4-piperidinyl]succinate Bis[1-(2'-cyanoethyl)-2,2,6,6-tetramethyl-4-piperidinyl]sebacate
Bis[1-(2',3'-epoxypropyl)-2,2,6,6-tetramethyl-4-piperidinyl]azelate
Bis[1-(2'-methoxyethyl)-2,2,6,6-tetramethyl-4-piperidinyl]pimelate
Bis[1-(2'-acetoxyethyl)-2,2,6,6-tetramethyl-4-piperidinyl]glutarate
Bis[1-(2'-methylcarbamoyloxyethyl)-2,2,6,6-tetramethyl-4-piperidinyl]malonate
Bis[1-(methylcarbonylmethyl)-2,2,6,6-tetramethyl-4-piperidinyl]terephthalate
Bis[1-carbamoylmethyl-2,2,6,6-tetramethyl-4-piperidinyl]cyclohexane-1',4'-dicarboxylate
Bis[1-(methylcarbamoylethyl)-2,2,6,6-tetramethyl-4-piperidinyl]thiodipropionate
Bis[1-acetyl-2,2,6,6-tetramethyl-4-piperidinyl]sebacate
Bis[1-stearoyl-2,2,6,6-tetramethyl-4-piperidinyl]succinate
Bis[1-Benzoyl-2,2,6,6-tetramethyl-4-piperidinyl]dodecandioate
Bis[1-methylcarbamoyl-2,2,6,6-tetramethylpiperidinyl]adipate Bis[1-phenylthiocarbamoyl-2,2,6,6-tetramethyl-piperidinyl]isophthalate
ethane-1',2'-bis[4-carbamoyloxy-1,2,2,6,6-pentamethylpiperidine]
hexane-1',6'-bis[4-carbamoyloxy-1,2,2,6,6-pentamethylpiperidine]
2',4',4'-trimethylhexane-1',6'-bis[4-carbamoyloxy-1,2,2,6,6-pentamethylpiperidine]
cyclohexane-1',3'-bis[4-carbamoyloxy-1,2,2,6,6-pentamethylpiperidine]
benzene-1',4'-bis[4-carbamoyloxy-1,2,2,6,6-pentamethylpiperidine]
toluene-2',4'-bis[4-carbamoyloxy-1,2,2,6,6-pentamethylpiperidine]
toluene-2',4'-bis[4-thiocarbamoyloxy-1,2,2,6,6-pentamethylpiperidine]
naphthalene-1',5'-bis[4-carbamoyloxy-1,2,2,6,6-pentamethylpiperidine]
diphenylmethane-4',4''-bis[4-carbamoyloxy-1,2,2,6,6-pentamethylpiperidine]
toluene-2',4'-bis[4-carbamoyloxy-1-n-propyl-2,2,6,6-tetramethylpiperidine]
hexane-1',6'-bis[4-carbamoyloxy-1-n-butyl-2,2,6,6-tetramethylpiperidine]
Hexane-1',6'-bis[4-carbamoyloxy-1-n-octyl-2,2,6,6-2',4',4'-trimethylhexane]-1',6'-bis[4-carbamoyloxy-1-n-octadecyl-2,2,6,6-tetramethylpiperidine]
Cyclohexane-1',4'-bis[4 -carbamoyloxy-1-allyl-2,2,6,6-tetramethylpiperidine]
2',4',4'-trimethylhexane-1',6'-bis[4-carbamoyloxy-1-allyl-2,2,6,6-tetramethylpiperidine]
Benzene-1',4'-bis[4-carbamoyloxy-1-propargyl-2,2,6,6-tetramethylpiperidine]
toluene-2',4'-bis[4-carbamoyloxy-1-benzyl-2,2,6,6-tetramethylpiperidine]
Toluene-2'',4''-bis[4-carbamoyloxy-1-(2'-hydrocyethyl)-2,2,6,6-tetramethylpiperidine]
Diphenylmethane-4',4''-bis[4-carbamoyloxy-1-(2'-cyanoethyl)-2,2,6,6-tetramethylpiperidine]
Toluene-2'',4''-bis[4-carbamoyloxy-1-(2''-acetoxyethyl)-2,2,6,6-tetramethylpiperidine]
Ethane-1',2'-bis[4-carbamoyloxy-1-methylcarbonylmethyl-2,2,6,6-tetramethylpiperidine]
Hexane-1'',6''-bis[4-carbamoyloxy-1-(2'-methylcarbamoylethyl)-2,2,6,6-tetramethylpiperidine]
Naphthalene-1',5'-bis[4-carbamoyloxy-1-acetyl-2,2,6,6-tetramethylpiperidine]
2',4',4'-trimethylhexane-1',6'-[4-carbamoyloxy-1-stearoyl-2,2,6,6-tetramethylpiperidine]
Hexane-1',6'-bis[4-carbamoyloxy-1-methylcarbamoyl-2,2,6,6-tetramethylpiperidine]
Bis[1,2,2,6,6-pentamethyl-4-piperidinyl]ether Examples where $n = 3$ Tris(1,2,2,6,6-pentamethyl-4-piperidinyl)nitrilotriacetate
Tris(1,2,2,6,6-pentamethyl-4-piperidinyl)tricarballylate
Tris(1,2,2,6,6-pentamethyl-4-piperidinyl)trimesate
Tris(1,2,2,6,6-pentamethyl-4-piperidinyl)trimellitate
Tris(1,2,2,6,6-pentamethyl-4-piperidinyl)phosphite
Tris(1,2,2,6,6-pentamethyl-4-piperidinyl)phosphate
Tris(1,2,2,6,6-pentamethyl-4-piperidinyl)borate
Tris(1-n-octadecyl-2,2,6,6-tetramethyl-4-piperidinyl)trimesate
Tris(1-allyl-2,2,6,6-tetramethyl-4-piperidinyl)phosphite
Tris(1-propargyl-2,2,6,6-tetramethyl-4-piperidinyl)borate
Tris(1-benzyl-2,2,6,6-tetramethyl-4-piperidinyl)trimellitate
Tris[1-(2'-hydroxyethyl)-2,2,6,6-tetramethyl-4-piperidinyl]trimesate
Tris[1-(2'-cyanoethyl)-2,2,6,6-tetramethyl-4-piperidinyl]phosphite
Tris[1-acetyl-2,2,6,6-tetramethyl-4piperidinyl]borate
Tris[1-methylcarbamoyl-2,2,6,6-tetramethyl-4-piperidinyl]trimesate Examples where $n = 4$ Tetrakis(1,2,2,6,6-pentamethyl-4-piperidinyl)ethylenediamine tetracarboxylate
Tetrakis(1,2,2,6,6-pentamethyl-4-piperidinyl)pyromellitate
Tetrakis(1,2,2,6,6-pentamethyl-4-piperidinyl)o-silicate
Tetrakis(1-n-octyl-2,2,6,6-tetramethyl-4-piperidinyl)-pyromellitate
Tetrakis(1-allyl-2,2,6,6-tetramethyl-4-piperidinyl)-pyromellitate
Tetrakis(1-propargyl-2,2,6,6-tetramethyl-4-piperidinyl)-o-silicate
Tetrakis(1-benzyl-2,2,6,6-tetraethyl-4-piperidinyl)ethylenediamine tetracarboxylate
Tetrakis[1-(2'-hydroxypropyl)-2,2,6,6-tetramethyl-4-piperidinyl]-o-silicate
Tetrakis[1-stearoyl-2,2,6,6-tetramethyl-4-piperidinyl]-pyromellitate
Tetrakis[1-phenylcarbamoyl-2,2,6,6-tetramethyl-4-piperidinyl]-o-silicate The invention also includes salts of the compounds of Formula I, for instance salts of inorganic acids such as phosphates, carbonates, sulphates, and chlorides and salts of organic acids such as acetates, stearates, maleates, citrates, tartrates, oxalates, benzoates and substituted carbamic acids.

Examples of salts are 4-n-butoxy-1,2,2,6,6-pentamethylpiperidine dihydrogen phosphate
4-n-dodecyloxy-1,2,2,6,6-pentamethylpiperidine hydrochloride
bis(1,2,2,6,6-pentamethyl-4-piperidinyl)sebacate sulphate
1,2,2,6,6-pentamethylpiperidinyl-4-beta-(3',5'-di-t-butyl-4'-hydroxyphenyl)propionate.bicarbonate
4-methylcarbamoyloxy-1,2,2,6,6-pentamethylpiperidine.acetate
1,6-bis(4'-carbamoyloxy-1',2',2',6',6'-pentamethylpiperidine hexane.stearate
4-phenyl carbamoyloxy-1,2,2,6,6-pentamethylpiperidine.benzoate
1,2,2,6,6-pentamethylpiperidinyl-4-n-octanoate 3',5'-di-t-butyl-4'-hydroxybenzoate
1,4-bis(1',2',2',6',6'-pentamethyl-4'-piperidyloxy)butane hydrogen oxalate
4-(2'-cyanoethoxy)-1,2,2,6,6-pentamethylpiperidine hydrogen maleate
4-stearylcarbamoyloxy-1,2,2,6,6-pentamethyl-piperidine.citrate
1-(2'-hydroxyethyl)-2,2,6,6-tetramethylpiperidinyl-4-n-octanoate.tartrate
1,2,2,6,6-pentamethylpiperidinyl--4-benzoate.dibutyl carbamate.

$R_1$ or $R_3$ can be represented by a monovalent, divalent or trivalent group obtained by removing 1 to 3 hydroxyl groups from a sulphonic acid, a sulphinic acid, a disulphonic acid, a phosphorus containing acid, such as o-phosphoric or o-phosphorous acid or a boric acid. The following list shows compounds with acid radicals for $R_3$. However, the same radicals are also examples for $R_1$.

a. when n is 1

1,2,2,6,6-pentamethylpiperidinyl-4-benzene sulphinate
1,2,2,6,6-pentamethylpiperidinyl-4-benzene sulphonate
1,2,2,6,6-pentamethylpiperidinyl-4-methyl sulphate
1,2,2,6,6-pentamethylpiperidinyl-4-dimethylborate
1,2,2,6,6-pentamethylpiperidinyl-4-phenyl phosphonate
1,2,2,6,6-pentamethylpiperidinyl-4-dimethyl phosphite
1,2,2,6,6-pentamethylpiperidinyl-4-diphenyl phosphate b. when n is 2 bis(1,2,2,6,6-pentamethyl-4-piperidinyl)sulphate
bis(1,2,2,6,6-pentamethyl- 4-piperidinyl)phosphonate
bis(1,2,2,6,6-pentamethyl-4-piperidinyl)phenyl phosphate
bis(1,2,2,6,6-pentamethyl-4-piperidinyl)benzene-1,3-disulphinate c. when n is 3 tris(1,2,2,6,6-pentamethyl-4-piperidinyl)-benzene-1,3,5-trisulphonate
tris(1,2,2,6,6-pentamethyl-4-piperidinyl)-benzene-1,3,5-trisulphinate.

A preferred sub-group of compounds of formula I are those compounds having the formula:

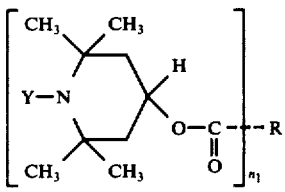

Ia and their salts,
wherein Y is an alkyl group having from 1 to 20, preferably 1 to 4, carbon atoms, alkenyl having from 3 to 20 carbon atoms or an aralkyl residue, preferably having from 7 to 9 carbon atoms, and
$n_1$ is 1 to 2;
when $n_1$ is 1, R is hydrogen or a monovalent aliphatic residue having from 1 to 20, preferably 6 to 20 carbon atoms, a monovalent alicyclic residue having from 5 to 12 carbon atoms, or a monovalent aromatic residue having from 6 to 20 carbon atoms; or

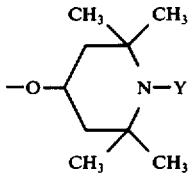

and
when $n_1$ is 2, R is a divalent aliphatic residue having from 1 to 20, preferably 4 to 20 carbon atoms, a divalent alicyclic residue having from 5 to 12 carbon atoms or a divalent aromatic residue having from 6 to 14 carbon atoms. Two sub-groups of the compounds of the formula Ia are those having as Y alkyl from 1 to 4 carbon atoms and alkyl having 5 to 20 carbon atoms.

Examples of substituents Y are methyl, ethyl, n-propyl, isopropyl, n-butyl, sec.butyl, n-hexyl, n-octyl, n-dodecyl, n-octadecyl, eicosyl, allyl, methallyl, oleyl, benzyl, α-methylbenzyl, p-methylbenzyl and p-methyl-α-methylbenzyl, However, it is particularly preferred that Y is methyl.

When $n_1$ is 1, R can be hydrogen, methyl, ethyl, n-propyl, isopropyl, n-butyl, sec.butyl, t-butyl, n-pentyl, 2-ethylpropyl, 2-methylbutyl, n-hexyl, 2-methylpentyl, n-heptyl, 2-ethylpentyl, n-octyl, 2,2,4-trimethylpentyl, n-decyl, n-undecyl, n-tridecyl, n-pentadecyl, n-heptadecyl, eicosyl, vinyl, α- or β-methylvinyl, dec-9-enyl, heptadec-8-enyl, β-methylthioethyl, β-octylthioethyl, β-dodecylthioethyl, cyclopentyl, cyclohexyl, cyclohex-3-enyl, methylcyclohexyl, t-butylcyclohexyl, cyclododecyl, 1- or 2-perhydronaphthyl, adamantyl, cyclopentylmethyl, cyclohexylmethyl, β-cyclohexyl, 1- or 2-(perhydronaphthyl)methyl, β-[1- or 2-perhydronaphthyl]ethyl, benzyl, β-phenylethyl, β-phenylvinyl, 1- or 2-naphthylmethyl, β-[1- or 2-naphthyl]ethyl, phenyl, o-, m- or p-tolyl, o-, m- or p-ethylphenyl, o-, m- or p-isopropylphenyl, o-, m- or p-t-butylphenyl, phenylphenyl, 4-methyl.1-naphthyl, 4-ethyl-1-naphthyl, 4-isopropyl-1-naphthyl or 4-t-butyl-1-naphthyl or the group

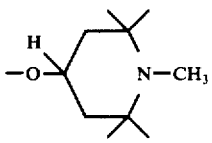

Particularly preferred substituent groups R are those listed above containing from 6 to 20 carbon atoms, as well as the group having the formula:

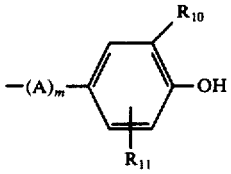

III wherein $R_{10}$ and $R_{11}$ are the same of different and each is an alkyl group having from 1 to 6, preferably 1 to 4 carbon atoms such as methyl, ethyl, n-propyl, isopropyl, sec.butyl, t-butyl, t-pentyl, (1,1-dimethylpropyl), t-hexyl (1,1-dimethylbutyl), but preferably methyl, isopropyl or t-butyl groups;
A is —CH₂—,

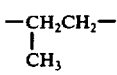

and p is 0 or 1.

When $n_1$ is 2, R can be methylene, 1,2-ethylene, 1,4-n-butylene, 1,8-n-octylene, 2,2,4-trimethyl-1, 4-butylene, 1,10-n-decylene, 1,2-eicosylene, vinylene, propenylene, 1,2-, 1,3- and 1,4-cyclohexylene, cyclohexyl-3-ene, 1,2-, 1,3- and 1,4-phenylene, p-xylylene, 1,4-, and 1,5-naphthylene, diphenylene or diphenylmethylene.

Specific examples of compounds having the formula Ia are shown above.

A further preferred sub-group of compounds of formula I are those having the formula:

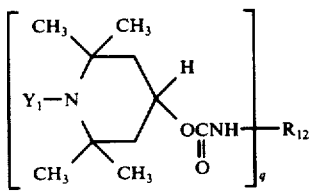
Ib and its salts
wherein $Y_1$ is an alkyl residue having from 1 to 12 carbon atoms, an alkenyl residue having from 3 to 12 carbon atoms or an aralkyl residue having from 7 to 9 carbon atoms and $R_{12}$ is hydrogen or an alkyl or alkylen containing up to 20 carbon atoms, an substituted alkyl having the formula

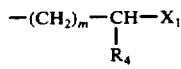

or

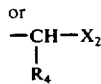

wherein $m$ is 1, 2 and 3,
$R_4$ is hydrogen or methyl,
$X_1$ is halogen or methoxy and
$X_2$ is halogen
or $R_{12}$ is an alkenyl or alkenylen having up to 20 carbon atoms, a cycloalkyl or cycloalkyliden having 5 to 12 carbon atoms, an aryl or arylen having 6 to 12 carbon atoms and $q$ is 1 to 2.

Two sub-groups of compounds of the formula Ib are those having as $Y_1$ alkyl from 1 to 4 and alkyl having 5 to 12 carbon atoms.

When $q$ is 1, $R_{12}$ can be for example hydrogen, methyl, ethyl, n-propyl, isopropyl, n-butyl, secbutyl, t-butyl, n-pentyl, 2-ethylpropyl, 2-methylbutyl, n-hexyl, 2-methylpentyl, n-heptyl, 2-ethylpentyl, n-octyl, 2-ethylhexyl, 2,2,4-trimethylpentyl, n-decyl, n-dodecyl, n-tetradecyl, n-octadecyl, eicosyl, mesityl, allyl, oleyl, cyclopentyl, cyclohexyl, methylcyclohexyl, t-butylcyclohexyl, t-octylcyclohexyl, cyclododecyl, 1- and 2-perhydronaphthyl, adamantyl, cyclopentylmethyl, cyclohexylmethyl, β-cyclohexylethyl, benzyl, β-Phenylethyl, 1- and 2-naphthylmethyl, β[1- and 2-naphthyl]ethyl, phenyl, o-, m- and p-tolyl, 2,4- and 2,6-xylyl, p-chlorophenyl, 3-chloro-p-tolyl, o-ethylphenyl, p-t-butylphenyl, 2,3- and 2,5-di-chlorophenyl, α- and β-naphthyl, phenylphenyl. Preferred monovalent groups $R_{12}$ are hydrocarbyl groups such as methyl, ethyl, propyl, isopropyl, n-butyl, 2-ethylhexyl, dodecyl, octadecyl, allyl, oleyl, cyclohexyl, benzyl, phenyl, o-, m- and p-tolyl, 2,4- and 2,6-xylyl and naphthyl.

When $q$ is 2, $R_{12}$ can be for example methylene, 1,2-ethylene, 1,4-n-butylene, 1,6-n-hexylene, 1,8-n-octylene, 2,4,4-trimethyl-1,6-hexylene, 1,10-n-decylene, 1,2-eicosylene, 1,2-eicosenylene, 1,3- and 1,4-cyclohexylene, 1,3- and 1,4-phenylene, 2,4-tolylene, 1,5-naphthylene, 4,4'-diphenylene, 4,4'-diphenylmethylene, 3,3'-dimethyl-4,4'-diphenylene, 3,3'-di-methyl-4,4'-diphenylmethylene.

Preferred divalent groups $R_{12}$ are 1,2-ethylene, 1,6-hexylene, 2,4,4-trimethyl-1,6-hexylene, 1,3- and 1,4-phenylene, 2,4-tolylene, 1,5-naphthylene, 4,4'-diphenylmethylene.

In the above formula Ib, examples of the group $Y_1$ are methyl, ethyl, n-propyl, isopropyl, n-butyl, secbutyl, n-hexyl, n-octyl, n-dodecyl, allyl, α-methallyl, 10-undecenyl, benzyl, α-methylbenzyl, p-methylbenzyl, p-methyl-α-methylbenzyl, α-naphthylmethyl. Particularly preferred are straight or branched alkyl having 1 to 4 carbon atoms and for reasons of ease of preparation the most preferred meaning for $Y_1$ is methyl.

Specific examples of the carbamoyloxy derivatives of N-substituted-2,2,6,6-tetrasubstituted piperidin-4-ols of formula Ic are given above.

The following groups A to O are subgroups of compounds of the formula I.

A. Compounds of formula I wherein when $n$ is 1, $R_3$ is a monovalent residue and is an alkyl residue having from 1 to 20 carbon atoms, a cycloalkyl residue having from 5 to 12 carbon atoms, an alkenyl or alkynyl residue having from 3 to 20 carbon atoms, an aralkyl residue having from 7 to 12 carbon atoms, or a residue having the formula:

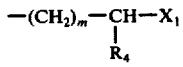

or

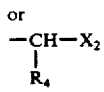

wherein $m$ is 1, 2 or 3, $R_4$ is a hydrogen, methyl or phenyl residue, $X_2$ is halogen, cyano,

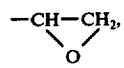

—$COR_5$, —$CO.OR_5$, —$CO.SR_5$ or —$CONR_5R_6$ and $X_1$ is hydroxyl, halogen, cyano,

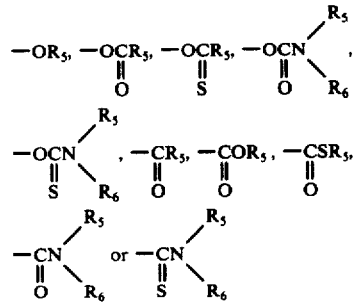

wherein $R_5$ is an alkyl residue having from 1 to 20 carbon atoms, an alkenyl residue having from 2 to 20 carbon atoms, a cycloalkyl residue having from 5 to 12 carbon atoms, an aryl residue having from 6 to 11 carbon atoms or an alalkyl residue having 7 to 14 carbon atoms or when $R_5$ is joined to a nitrogen atom, also hydrogen and $R_6$ is hydrogen or an alkyl residue having from 1 to 4 carbon atoms, or $R_5$ and $R_6$ together with the nitrogen atom to which they are bound form a 5- or 6-membered ring which contains no other heteroatoms or contains one or more other heteroatoms or $R_3$ is an aryl residue or a residue having the formula:

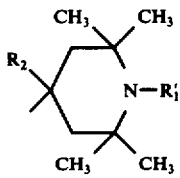

wherein $R_1'$ is hydrogen or $R_1'$ has the same significance as $R_1$ of formula I; when $n$ is 2 $R_3$ is a divalent residue and is an alkylene residue having from 1 to 20 carbon atoms, an alkenylene residue having from 2 to 20 carbon atoms, an alkynylene residue having from 2 to 20 carbon atoms, a cycloalkyliden residue having from 3 to 12 carbon atoms, an arylene residue having 6 to 14 carbon atoms, an aralkylene residue having from 8 to 14 carbon atoms; when $n$ is 3, $R_3$ is a trivalent residue and is an alkanetriyl, an arenetriyl or an arenetriyl-trialkylene residue, and when $n$ is 4, $R_3$ is a tetravalent residue and is an alkanetetrayl residue.

B) Compounds of the formula I wherein when $n$ is 1 $R_3$ is an acyl group

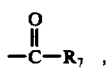

wherein $R_7$ is hydrogen, an unsubstituted aliphatic or substituted aliphatic residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 14 carbon atoms, an aromatic residue having from 6 to 20 carbon atoms or an heterocyclic residue, or $R_3$ represents a monovalent group obtained by removing a hydroxyl group from a sulphinic acid, a sulphonic acid, a phosphorus containing acid or a boric acid, when $n$ is 2, $R_3$ is an divalent residue of an aliphatic, aromatic or heterocyclic diacyl, the group —CO— or —CO.CO—, a sulphinyl or sulphonyl residue or a divalent residue obtained by removing two hydroxyl groups from a disulphonic acid, a phosphorus containing acid or a boric acid;

when $n$ is 3, $R_3$ is a trivalent residue of an aliphatic or aromatic triacyl residue or a triacyl residue derived from o-phosphoric, o-phosphorous or o-boric acid; and when $n$ is 4, $R_3$ is a tetravalent residue of a tetraacyl residue derived from an aliphatic or aromatic tetracarboxylic acid or from o-silicic acid.

C. Compounds of the formula I wherein $n$ is 1 or 2 and when $n$ is 1

$R_3$ is a carbamoyl residue having the formula:

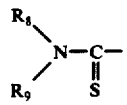

wherein $R_8$ is hydrogen or an alkyl residue having from 1 to 4 carbon atoms, and $R_9$ is hydrogen, an alkyl residue having from 1 to 20 carbon atoms, an alkenyl residue having from 3 to 20 carbon atoms, a cycloalkyl residue having from 5 to 12 carbon atoms or an unsubstituted aryl or substituted aryl residue having from 6 to 12 carbon atoms;

and when $n$ is 2 $R_3$ is a divalent aliphatic or aromatic dicarbamoyl residue.

D. Compounds of the formula I wherein $n$ is 1 or 2 and when $n$ is 1

$R_3$ is a thiocarbamoyl residue having the formula:

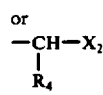

wherein $R_8$ is hydrogen or an alkyl residue having from 1 to 4 carbon atoms, and $R_9$ is hydrogen, an alkyl residue having from 1 to 20 carbon atoms, an alkenyl residue having from 3 to 20 carbon atoms, a cycloalkyl residue having from 5 to 12 carbon atoms or an unsubstituted aryl or substituted aryl residue having from 6 to 12 carbon atoms;

and when $n$ is 2, $R_3$ is a divalent aliphatic or aromatic dithiocarbamoyl.

E. Compounds of the formula I wherein when $n$ is 1 $R_3$ is a monovalent residue and is an alkyl residue having from 1 to 20 carbon atoms, a cycloalkyl residue having from 5 to 12 carbon atoms, an alkenyl or alkynyl residue having from 3 to 20 carbon atoms, an aralkyl residue having from 7 to 9 carbon atoms, or a residue having the formula:

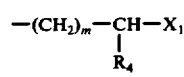

or

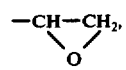

wherein $m$ is 1, 2 or 3, $R_4$ is a hydrogen, methyl or phenyl residue, $X_2$ is halogen, cyano,

—CH—CH$_2$,
\ /
O

—COR$_5$, —CO.OR$_5$, —CO.SR$_5$ or —CONR$_5$R$_6$ and X$_1$ is hydroxyl, halogen, cyano, —OR$_5$, —O—CO.R$_5$, —OCSR$_5$, —O.CO.NR$_5$R$_6$, —CO.R$_5$, —CO.OR$_5$, —CO.SR$_5$, —CO.NR$_5$R$_6$ or —CS.NR$_5$R$_6$, wherein $R_5$ is an alkyl residue having from 1 to 20 carbon atoms, an alkenyl residue having from 2 to 20 carbon atoms, a cycloalkyl residue having from 5 to 12 carbon atoms, an aryl residue having from 6 to 11 carbon atoms, or an aralkyl residue having 7 to 11 carbon atoms, or when $R_5$ is joined to a nitrogen atom, also hydrogen and $R_6$ is hydrogen or an alkyl residue having from 1 to 4 carbon atoms, or $R_5$ and $R_6$ together with the nitrogen atom to which they are bound form a 5- or 6-membered ring which contains no other heteroatoms or contains one or more other heteroatoms or $R_3$ is an aryl residue or a residue having the formula:

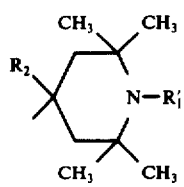

wherein R₁' is hydrogen or R₁' has the same significance as R₁ of claim 2;
when n is 2, R₃ is a divalent residue and is an alkylene residue having from 1 to 20 carbon atoms, an alkenylene residue having from 3 to 20 carbon atoms, an alkynylene residue having from 3 to 20 carbon atoms, an arylene residue having 6 to 14 carbon atoms, an aralkylene residue having from 8 to 14 carbon atoms;
when n is 3, R₃ is a trivalent residue of an alkanotriyl, an arenetriyl, or arenetriyltrialkylene group; and
when n is 4, R₃ is a tetravalent residue of an alkanetetrayl group.

F. Compounds of the formula I wherein when n is 1 R₃ is an acyl group

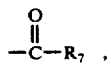

wherein R₇ is an aliphatic or substituted aliphatic residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 14 carbon atoms, an aromatic residue having from 6 to 12 carbon atoms or an heterocyclic residue, with the proviso that only one of R₁ and R₃ can represent an unsaturated acyl group or R₃ represents a monovalent group obtained by removing a hydroxyl group from a sulphinic acid, a sulphonic acid, a phosphorus containing acid or a boric acid,
when n is 2, R₃ is a divalent residue of an aliphatic, aromatic or heterocyclic diacyl residue, a carbonyl, sulphinyl or sulphonyl residue or a divalent residue obtained by removing two hydroxyl groups from a disulphonic acid, a phosphorus containing acid or a boric acid;
when n is 3, R₃ is a trivalent residue of an aliphatic or aromatic triacyl residue or a triacyl residue derived from o-phosphoric, o-phosphorous or o-boric acid and
when n is 4, R₃ is a tetravalent residue of a tetraacyl residue derived from an aliphatic or aromatic tetracarboxylic acid or from o-silicic acid.

G. Compound of the formula I wherein n is 1 or 2 and when n is 1, R₃ is a carbamoyl residue having the formula:

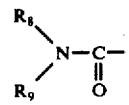

wherein R₈ is hydrogen or an alkyl residue having from 1 to 4 carbon atoms, and R₉ is hydrogen, an alkyl residue having from 1 to 20 carbon atoms, an alkenyl residue having from 3 to 20 carbon atoms, a cycloalkyl residue having from 5 to 12 carbon atoms or an aryl or substituted aryl residue having from 6 to 12 carbon atoms; and when n is 2, R₃ is a divalent residue of an aliphatic or aromatic dicarbamoyl residue.

H. Compounds of the formula I wherein n is 1 or 2 and when n is 1, R₃ is a thiocarbamoyl residue having the formula:

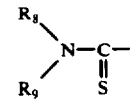

wherein R₈ is hydrogen or an alkyl residue having from 1 to 4 carbon atoms, and R₉ is hydrogen, an alkyl residue having from 1 to 20 carbon atoms, an alkenyl residue having from 3 to 20 carbon atoms, a cycloalkyl residue having from 5 to 12 carbon atoms or an aryl or substituted aryl residue having from 6 to 12 carbon atoms;
and when n is 2, R₃ is a divalent residue of an aliphatic or aromatic dithiocarbamoyl residue.

I. Compounds of formula I and their bicarbonate wherein n is 1, 2 or 3
R₁ is alkyl having from 1 to 18 carbon atoms, benzyl or alkenyl having 3 carbon atoms or a group of the formula:

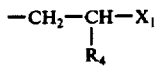

or

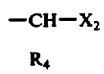

wherein R₄ is hydrogen, methyl or phenyl and X₁ is a group of the formula

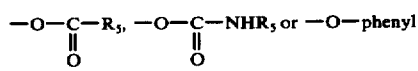

and
X₂ is a group of the formula

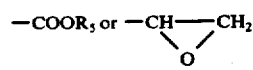

wherein R₃ is alkyl having 1 or 2 carbon atoms or phenyl or R₁ is a group of the formula

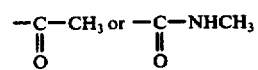

and
R₂ is hydrogen and
R₃ when n is 1 is alkyl having 3 to 18 carbon atoms, alkenyl having 3 carbon atoms, propargyl, benzyl, —CH₂CH₂CN or a group of the formula

—CH₂X₂ wherein X₂ is

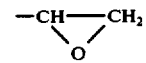

or —COOC₂H₅ of of the formula

wherein R₇ is alkyl having 1 to 19 carbon atoms, CH₃(CH₂)₁₁—S-CH₂—, cycloalkyl having 6 to 10 carbon atoms, alkenyl having 2 to 17 carbon atoms, unsubstituted aralkyl having 7 to 13 carbon atoms, C₆H₅—CH=CH—, aralkyl substituted by hydroxy or butyl, unsubstituted aryl having 6 to 10 carbon atoms, aryl substituted by alkyl having 1 to 4 carbon atoms, $CH_3O-$, Cl, OH, or

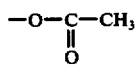

or of the formula

wherein $R_9$ is alkyl having 1 to 8 carbon atoms, alkenyl having 3 carbon atoms, cyclohexyl, unsubstituted aryl having 6 to 10 carbon atoms, aryl substituted by methyl or Cl or $R_3$ when $n$ is 2 is the group $-CO-R-CO-$
wherein R is alkylen having 4 to 8 carbon atoms, $-CH_2CH_2-S-CH_2CH_2-$, vinylen, cyclohexylen, a divalent thiophen residue, unsubstituted phenylen or phenylen substituted by

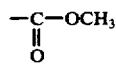

or a group of the formula $-CONHR'NHCO-$
wherein $R'$ is hexylen, unsubstituted arylene having 6 to 10 carbon atoms, arylene substituted by methyl or $R'$ is the group

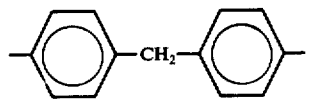

or a group of the formula $-COCO-$ or butylen or $R_3$ when $n$ is 3, is

J. Compounds of the formula I wherein $n$ is 1, 2 or 4 and when $n$ is 1, $R_3$ is an acyl group

wherein $R_7$ is hydrogen, an substituted aliphatic residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 14 carbon atoms, or an heterocyclic residue, or $R_3$ represents a monovalent group obtained by removing a hydroxyl group from a sulphinic acid, a sulphonic acid, a phosphorus containing acid or a boric acid, or when $n$ is 2, $R_3$ is an divalent residue of heterocyclic diacyl residue or a sulphinyl or sulphonyl residue or a divalent residue obtained by removing two hydroxyl groups from a disulphonic acid, a phosphorus containing acid or a boric acid; or when $n$ is 4, $R_3$ is a tetraacyl residue derived from an aliphatic tetracarboxylic acid.

K. Compounds of the formula I wherein $n$ is 1, 2 and 4 and when $n$ is 1, $R_3$ is an acyl group

wherein $R_7$ is hydrogen, a cycloaliphatic residue having from 5 to 12 carbon atoms or a heterocyclic residue or $R_3$ represents a monovalent group obtained by removing a hydroxyl group from a sulphinic acid, a sulphonic acid, a phosphorus containing acid or a boric acid or when $n$ is 2, $R_3$ is a divalent residue of a heterocyclic diacyl or a sulphinyl or sulphonyl residue or a divalent residue obtained by removing two hydroxyl groups from a disulphonic acid, a phosphorus containing acid or when $n$ is 4, $R_3$ is a tetraacyl residue derived from an aliphatic tetracarboxylic acid.

L. Compounds of the formula I wherein $n$ is 1, 2 or 4 and when $n$ is 1, $R_3$ is an acyl group

wherein $R_7$ is hydrogen, a substituted aliphatic residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 14 carbon atoms, or an heterocyclic residue, or $R_3$ represents a monovalent group obtained by removing a hydroxyl group from a sulphinic acid, a sulphonic acid, a phosphorus containing acid or a boric acid, or when $n$ is 2, $R_3$ is a divalent residue of heterocyclic diacyl residue or a sulphinyl or sulphonyl residue or a divalent residue obtained by removing two hydroxyl groups from a disulphonic acid, a phosphorus containing acid or a boric acid; or when $n$ is 4, $R_3$ is a tetraacyl residue derived from an aliphatic tetracarboxylic acid.

M. Compounds of the formula I wherein $n$ is 1, 2 and 4 and when $n$ is 1, $R_3$ is an acyl group

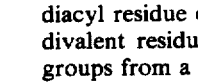

wherein $R_7$ is hydrogen, a cycloaliphatic residue having from 5 to 12 carbon atoms or a heterocyclic residue or $R_3$ represents a monovalent group obtained by removing a hydroxyl group from a sulphinic acid, a sulphonic acid, a phosphorus containing acid or a boric acid or when $n$ is 2, $R_3$ is a divalent residue of a heterocyclic diacyl or a sulphinyl or sulphonyl residue or a divalent residue obtained by removing two hydroxyl groups from a disulphonic acid, a phosphorus containing acid or when $n$ is 4, $R_3$ is a tetraacyl residue derived from an aliphatic tetracarboxylic acid.

N. Compounds of the formula I wherein when $n$ is 1, $R_3$ is an acyl group

wherein R[7] is an unsubstituted aliphatic residue having from 1 to 20 carbon atoms or an aromatic residue having from 6 to to 20 carbon atoms and when n is 2, R$_3$ is an divalent aliphatic or aromatic diacyl residue or the groups —CO— or —COCO— and when n is 3, R$_3$ is a trivalent residue and is an aliphatic or aromatic triacyl residue or a triacyl residue derived from o-phosphoric, o-phosphorous or o-boric acid and when n is 4, R$_3$ is a tetravalent residue of a tetraacyl residue derived from an aromatic tetracarboxylic acid or from o-silicic acid.

O Compounds of the formula I wherein when n is 1, R$_3$ is an acyl group

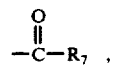

wherein R$_7$ is an unsubstituted aliphatic residue having from 1 to 20 carbon atoms or an aromtic residue having from 6 to 12 carbon atoms and when n is 2, R$_3$ is an divalent aliphatic or aromatic diacyl residue or the carbonyl group and when n is 3, R$_3$ is a trivalent residue and is an aliphatic or aromatic triacyl residue or a triacyl residue derived from o-phosphoric, o-phosphorous or o-boric acid and when n is 4, R$_3$ is a tetravalent residue of a tetraacyl residue derived from an aromatic tetracarboxylic acid or from o-silicic acid.

The following groups P and Q are sub-groups of the compounds of formula Ia.

P. Compounds of the formula Ia wherein
n is 1 and R is hydrogen or a monovalent alicyclic residue having from 5 to 12 carbon atoms.

Q. Compounds of the formula Ia wherein
when n is 1, R is a monovalent aliphatic residue having from 1 to 20 carbon atoms or a monovalent aromatic residue having from 6 to 20 carbon atoms and
when n is 2, R is a divalent aliphatic residue having from 1 to 20 carbon atoms or a divalent aromatic residue having from 6 to 20 carbon atoms.

The following compounds of the formula I are also a group of compounds of the present invention.

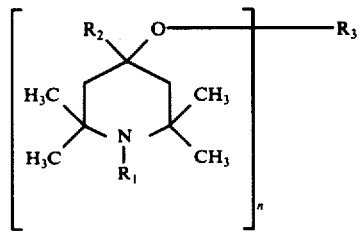

I wherein n is 1, 2, 3 or 4; R$_1$ is a monovalent residue and is an alkyl residue having from 1 to 20 carbon atoms, a cycloalkyl residue having from 5 to 12 carbon atoms, an alkenyl or alkynyl residue having from 3 to 20 carbon atoms, an aralkyl residue having from 7 to 9 carbon atoms, or a residue having the formula:

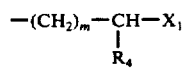

or

—CH—X$_2$
 |
 R$_4$ wherein m is 1, 2 or 3, R$_4$ is a hydrogen, methyl or phenyl residue, X$_2$ is halogen, cyano,

—COR$_5$, —CO.OR$_5$ —CO.SR$_5$, —CONR$_5$R$_6$ or —CS.NR$_5$R$_6$ and X$_1$ is hydroxyl, halogen, cyano,

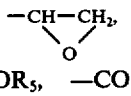

—OR$_5$, —O—CO.R$_5$, OCSR$_5$, —O.CO.NR$_5$R$_6$, —CO.R$_5$, —CO.OR$_5$, —CO.SR$_5$, —CO.NR$_5$R$_6$, —CS.NR$_5$R$_6$, or —SR$_5$, wherein R$_5$ is an alkyl residue having from 1 to 20 carbon atoms, an alkenyl residue having from 2 to 20 carbon atoms, a cycloalkyl residue having from 5 to 12 carbon atoms, an aryl residue having from 6 to 11 carbon atoms, or when R$_5$ is joined to a nitrogen atom, also hydrogen, and R$_6$ is hydrogen or an alkyl residue having from 1 to 4 carbon atoms, or R$_5$ and R$_6$ together with the nitrogen atom to which they are bound form a 5- or 6-membered ring which contains no other heteroatom or contains one or more other heteroatoms or R$_1$ is an acyl group, an unsubstituted or N-substitued carbamoyl or thiocarbamoyl group; R$_2$ is an alkyl residue having from 1 to 4 carbon atoms, an alkenyl or alkynyl residue having 3 to 20, carbon atoms, a cycloalkyl residue having from 5 to 12 carbon atoms, an aryl residue having from 6 to 11 carbon atoms or an aralkyl residue having from 7 to 9 carbon atoms or also hydrogen; and when n is 1, R$_3$ is a monovalent radical having the same significance as R$_1$, with the proviso that only one of R$_1$ and R$_3$ can represent an unsaturated acyl group or R$_3$ represents a monovalent group obtained by removing a hydroxyl group from a sulphinic acid, a sulphonic acid, a phosphorus containing acid or a boric acid, or R$_3$ is an aryl residue or a residue having the formula:

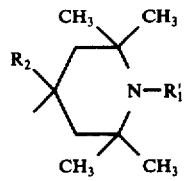

wherein R$_1$ ' is hydrogen or R$_1$ ' has the same significance as R$_1$.

When n is 2, R$_3$ is a divalent residue and is an alkyllene residue having from 1 to 20 carbon atoms, an alkenylene residue having from 3 to 20 carbon atoms, an alkynylene residue having from 3 to 20 carbon atoms, an arylene residue having 6 to 14 carbon atoms, an aralkylene residue having from 8 to 14 carbon atoms or an aliphatic, aromatic or heterocyclic diacyl residue, an aliphatic or aromatic dicarbamoyl or dithiocarbamoyl, a carbonyl, sulphinyl or sulphonyl residue or a divalent residue obtained by removing two hydroxyl groups from a disulphonic acid, a phosphorus containing acid or a boric acid; when n is 3, R$_3$ is a trivalent residue or an aliphatic or aromatic triacyl residue or a triacyl residue derived from o-phosphoric, o-phosphorous or o-boric acid or an alkanetriyl, an arenetriyl, or arenetriyltrialkylene group; and when n is 4, $R_3$ is a tetravalent residue and is a tetravalent aliphatic residue or tetraacyl residue derived from an aliphatic or aromatic tetracarboxylic acid or from o-silicic acid or an alkanetetrayl group; as well as partial ethers, esters and carbamoyloxy and thiocarbamoyloxy compounds related to the fully reacted compounds of formula I.

The following compounds of the formula II are also a group of compounds of the present invention.

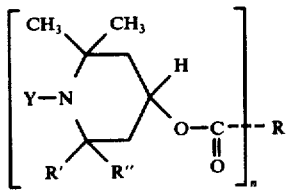

II and their salts, wherein R′ and R″ are the same or different and each is a straight or branched alkyl group, having from 1 to 4 carbon atoms, or R′ and R″ together with the carbon atom to which they are attached form a cycloalkyl residue having from 5 to 12 carbon atoms; Y is an alkyl group having from 1 to 20 carbon atoms, preferably 1 to 4, carbon atoms, alkenyl having from 2 to 20 carbon atoms or an aralkyl residue having from 7 to 9 carbon atoms and $n_1$ is 1 or 2; when n is 1, R is hydrogen or a monovalent aliphatic residue having from 1 to 20, preferably 6 to 20 carbon atoms, a monovalent alicyclic residue having from 5 to 12 carbon atoms, or a monovalent aromatic residue having from 6 to 20 carbon atoms; and when n is 2, R is a divalent aliphatic residue having from 1 to 20, preferably 1 to 20, carbon atoms, and is unsubstituted or substituted or interrupted by one or more, preferably one, sulphur atom, a divalent alicyclic residue having from 5 to 12 carbon atoms or a divalent aromatic residue having from 6 to 20 carbon atoms.

Subgroups of the compounds of formula II are
a. Compounds wherein Y is methyl or
b. Compounds wherein n is 1 and R is a monovalent aliphatic, alicyclic or aromatic residue having from 6 to 20 carbon atoms and this group has the formula:

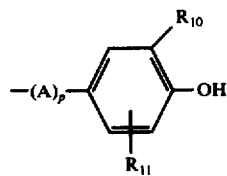

III wherein $R_{10}$ and $R_{11}$ are the same or different and each is an alkyl group having from 1 to 6 carbon atoms, A is

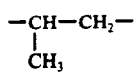

or —CH$_2$CH$_2$— and p is 0 or 1, or c. Compounds wherein $R_{10}$ and $R_{11}$ are methyl, isopropyl or t-butyl groups or
d. Compounds wherein n is 2 and R is a methylene, 1,2-ethylene, 1,4-butylene, 1,8-n-octylene, 2,2,4-trimethyl-1,4-butylene, 1,10-n-decylene, 1,2-eicosylene, vinylene, propenylene, 1,2-, 1,3- or 1,4-cyclohexylene, cyclohexyl-3-ene, 1,2-, 1,3-, or 1,4-phenylene, p-xylylene, 1,4-, or 1,5-naphthylene, diphenylene or diphenylmethylene residue or the group -CH$_2$CH$_2$S CH$_2$CH$_2$— or R is absent.

e. Compounds in the form of its salt of an inorganic or organic acid.

f. Compounds wherein the salt is a phosphate, carbonate, sulphate, chloride, acetate, stearate, maleate, nitrate, tartrate, oxalate, benzoate or substituted carbamate.

g. Compounds wherein R′ and R″ are methyl.

The following compounds of the formula IV are also compounds of the present invention:

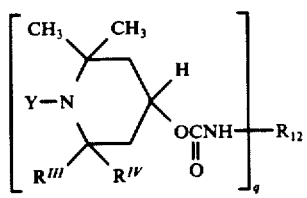

IV and its salts wherein $R^{III}$ and $R^{IV}$ are the same or different and each is a straight- or branched alkyl residue having from 1 to 12 carbon atoms or $R^{III}$ and $R^{IV}$ together with the carbon atom to which they are each attached form a cycloalkyl group having from 5 to 12 carbon atoms, Y is a straight- or branched alkyl residue having from 1 to 12 carbon atoms, an alkenyl residue having from 3 to 12 carbon atoms, or an aralkyl residue having from 7 to 12 carbon atoms and $R_{12}$ is hydrogen or a saturated or unsaturated hydrocarbyl residue containing up to 20 carbon atoms optionally substituted, Y halogen or alkoxy having from 1 to 4 carbon atoms and q is 1 or 2.

Sub-groups of the compounds of formula IV are:
a. Compounds wherein q is 1 and $R_{12}$ is an aliphatic residue having from 1 to 20 carbon atoms, an alicyclic residue having from 5 to 12 carbon atoms or an aromatic residue having from 6 to 12 carbon atoms.

b. Compounds wherein $R_{12}$ is a methyl, ethyl, propyl, isopropyl, n-butyl, 2-ethylhexyl, dodecyl, octadecyl, allyl, oleyl, cyclohexyl, benzyl, phenyl, o-, m- or p-tolyl, 2,4- or 2,6-xylyl or a naphthyl residue.

c. Compounds wherein q is 2 and $R_{12}$ is an aliphatic residue having from 1 to 20 carbon atoms, an alicyclic residue having from 5 to 15 carbon atoms or an aromatic residue having from 6 to 15 carbon atoms.

d. Compounds wherein $R_{12}$ is a 1,2-ethylene 1,6-hexylene, 2,4,4-trimethyl-1,6-hexylene, 1,3- or 1,4-phenylene, 2,4-tolylene, 1,5-naphthylene or 4,4′-diphenylmethylene residue.

e. Compounds wherein $Y_1$ is methyl.

f. Compounds in the form of its salt of an inorganic or organic acid.

g. Compounds wherein the salt is a phosphate, carbonate, sulphate, chloride, acetate, carbonate, sulphate, chloride, acetate, stearate, maleate, citrate, tertrate, oxalate, benzoate or substituted carbamate.

h. Compounds wherein $R^{III}$ and $R^{IV}$ are methyl.

According to the present invention, there is also provided a first process in which a compound of formula I is produced, comprising reacting, in the presence of an acid-binding agent, a piperidinol having the formula:

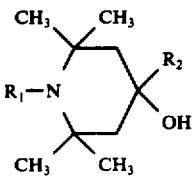
V wherein $R_1$ and $R_2$ have their previous significance, with an acid halide having the formula:

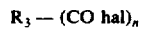
VI wherein $R_3$ and n have their previous significance and hal represents a halogen atom, preferably a chlorine atom.

Suitable acid binding agents are organic bases such as triethylamine; alternatively, an excess amount of the amine V can serve as the acid binding agent.

The reaction is conveniently carried out by heating the reactants together in a solvent such as cyclohexane, benzene or toluene which is inert under the reaction conditions. when the reaction is complete, the desired product is then separated by conventional techniques.

The present invention also provides a second process in which a compound of formula I is produced, comprising reacting, in the presence of a transesterification cataylst, a piperidinol compound of formula V, as hereinbefore defined, with an ester having the formula:

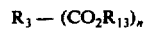
VII wherein $R_3$ and $n$ have their previous significance and $R_{13}$ is an alkyl residue having from 1 to 4 carbon atoms, preferably 1 or 2 carbon atoms.

Examples of suitable transesterification catalysts are alkali metal amides such as lithium amide.

A third process according to this invention in which a compound of formula I is produced comprises reacting, in the presence of an esterification catalyst, a piperidinol compound of formula V, as hereinbefore defined, with an acid having the formula:

VIII wherein $R_3$ and n have their previous significance.

Suitable examples of esterification catalysts are neutral catalysts such as tetraalkyl titanates such as tetrabutyl titanate.

The second and third processes of the invention are conveniently effected by mixing the reactants together in the presence or absence of an inert solvent (for instance, benzene, toluene, xylene etc.) and agitating the reaction mixture until reaction is complete, as determined, for instance, by collecting the alcohol or water produced in the reaction, and stopping the reaction when the theoretical amount of alcohol or water, respectively, has been removed.

A fourth process in which a compound of formula I is produced comprises reacting a compound having the formula:

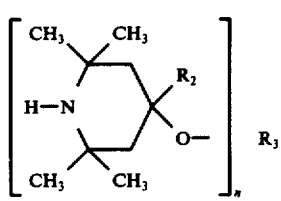
IX wherein $R_2$, $R_3$ and n have their previous significance, with a compound X capable of reaction with the compound IX and of introducing into it the group $R_1$ as hereinbefore defined.

For instance, compound X may be an alkylating, alkenylating or aralkylating agent such as the halides of these groups. Compound X may also be the aldehyde or ketone corresponding to the substituent $R_1$, so that, when reacted with a compound of formula IX under Leuckart, Wallach or Eschweilar-Charles reaction conditions, compounds of formula I in which $R_1$ is methyl may be produced by reacting a compound of formula IX with formic acid and formaldehyde.

The starting-materials of formulae V, VI, VII, VIII, IX and X used in the processes of this invention can all be produced by methods well-known per se. The compounds of formula V are described in our copending British Pat. Application No. (Case 32/72) and those of formula IX are described generally in German Pat. Spec. No. 1,929,928.

Compounds of the general formula I in which $b = 2$, 3 or 4 and $R_3$ represents a di-, tri- or tetra-valent radical derived from an alkyl, alkenyl, aryl or aralkyl radical may be prepared by reacting a compound of the formula:

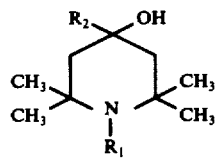
XIII $R_1$ and $R_2$ has its previous significance, with a compound of the formula $R_3(X_4)_n$ wherein $X_4$ is a halogen atom and n is 2, 3 or 4. This reaction is preferably carried out by making the sodium salt of the piperidine compound and reacting this with the compound $R_3(X_4)_n$.

The substitutents $R_1$ may be introduced before or after $R_3$ or in the case where $R_1$ and $R_3$ are identical may be introduced together by reacting a compound of the formula:

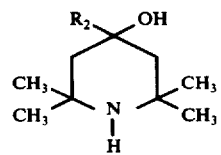
XI with an alkylating, alkenylating, alkynylating, aralkylating, acylating agent or carbamoyloxyating agent, with an alkylating, alkenylating, alkynylating, aralkylating or acylating agent.

Compounds of formula I in which $R_1$ represents a residue of the formula:

$$-(CH_2)_m-\underset{R_4}{CH}-X_1$$

in which $R_4$ is as defined above, m is 1 and $X_1$ represents $$-CN, -OR_5, -\underset{O}{OCR_5}, -\underset{S}{OCR_5}, -\underset{O}{OCNR_5R_6},$$

$$-\underset{O}{CNR_5R_6}, -\underset{O}{CR_5}, -\underset{O}{C}-OR_5, -\underset{O}{CSR_5},$$

$$-\underset{S}{CNR_5R_6} \text{ or } -\underset{S}{OCN}\diagdown_{R_6}^{R_5}$$

$R_5$ and $R_6$ being as defined above, may be produced by reacting a compound of the formula:

XII

[structure: piperidine ring with $R_2$, $OR_3$ at 4-position, $CH_3$, $CH_3$ at 2- and 6-positions, NH]

wherein $R_3$ and $R_2$ are as defined above, with a compound having the formula $$CH_2=\underset{R_4}{C}-X_1.$$

Compounds of formula I wherein m is 1 and $X_1$ is -OH may be prepared by reacting a compound of formula XII with ethylene oxide, propylene oxide or styrene oxide.

Compounds of formula I wherein $R_1$ is $$-CH_2-\underset{R_4}{CH}-X_1 \text{ wherein } X_1 \text{ is } -OR_5, -O-\underset{O}{\overset{O}{C}}-R_5,$$

$$-O-\overset{O}{\underset{\|}{C}}-N\diagdown_{R_6}^{R_5}$$

or halogen may be prepared from the corresponding compounds wherein $X_1$ is —OH by standard methods, such as alkylation, esterification, carbamoyloxylation or halogenation.

Compounds of formula I in which $R_1$ represents a residue of formula:

$$-(CH_2)_m-\underset{R_4}{CH}-X_1$$

wherein m, $R_4$ and $X_1$ are as hereinbefore defined may be prepared by reacting a compound of formula XII with the appropriate halogen compound having the formula:

$$X_3(CH_2)_m-\underset{R_4}{CH}-X_1$$

wherein $X_3$ is a halogen atom.

Compounds of formula I in which $R_1$ is the group of formula:

$$-\underset{R_4}{CH}-X_2$$

wherein $X_2$ and $R_4$ are as defined above may be prepared by reacting a compound of the formula XII wherein $R_2$ is as defined above with a compound of the formula $$X_4\underset{R_4}{CHX_2}$$

wherein $X_4$ is a halogen atom.

Compounds of the general formula I in which $R_1$ represents an acyl group may be prepared by reacting a compound of the formula:

XII

[structure: piperidine ring with $R_2$, $OR_3$ at 4-position, $CH_3$, $CH_3$ at 2- and 6-positions, NH]

wherein $R_2$ and $R_3$ are as defined with an acyl halide of the formula $$R_{14}\underset{O}{\overset{\|}{C}}X_5,$$

wherein $X_5$ is a halogen, and $R_{14}$ is the remainder of the acyl group.

Compounds of the general formula I in which $R_1$ represents a carbamoyl or thiocarbamoyl group may be prepared by reacting a compound of the formula:

XII

[structure: piperidine ring with $R_2$, $OR_3$ at 4-position, $CH_3$, $CH_3$ at 2- and 6-positions, NH]

$R_2$ and $R_3$ being as defined above with an isocyanate or thioisocyanate of the formula $R_{15}NCX^1$ in which $X^1$ is $>O$ or $>S$, and $R_{15}$ is the remainder of the isocyanate or thioisocyanate group.

Where $R_2$ in the general formula I is other than hydrogen it is preferred to introduce the appropriate group before or after the group $R_1$ is introduced, but before $R_3$ is introduced. The group $R_2$ may be introduced by reacting a ketone of the formula:

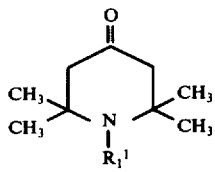

wherein $R_1'$ is hydrogen or $R_1$, with a Grignard reagent $R_2MgX$ followed by hydrolysis to produce a compound of the formula:

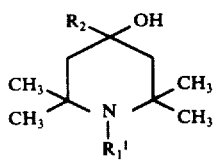

All the reactions described above which result in the elimination of hydrogen halide between two reactants may be carried out in the presence of an acid acceptor.

Compounds of formula II as defined hereinbefore are produced by reacting, in the presence of an acid-binding agent, a piperidinol compound having the formula:

XIV

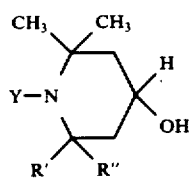

wherein Y, R' and R" are as defined hereinbefore with an acid halide having the formula:

R—(CO hal.)$_n$ wherein R and $n$ are as defined hereinbefore and hal. represents a halogen atom. The acid binding agent can be an organic or an excess amount of the amine reactant XIV and the reactants are for example heated together in a solvent inert under the reaction conditions.

The process can be performed in the presence of a transesterification catalyst, such as an alkali metal, a piperidinol compound having the formula XIV, with an ester having the formula:

R—(CO$_2$R$_{16}$)$_n$ wherein R and $n$ are as defined above and $R_{16}$ is an alkyl group having from 1 to 4 carbon atoms, or with an acid having the formula:

R—(CO$_2$H)$_n$ wherein R and $n$ are as defined above.

The catalyst of producing compounds of the formula II can be a neutral catalyst such as tetraalkyl titanate.

In the process for producing compounds of the formula II the reactants can also be fused, the mass is agitated until reaction is complete and the reaction is stopped when the reaction is complete. The completion of the reaction is determined for example by collecting, respectively, the alcohol or water produced in the reaction, and stopping the reaction when the theoretical amount of water or alcohol has been removed.

Compounds of formula II are also produced by reacting an ester having the formula:

XV

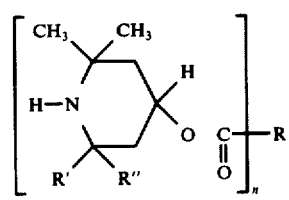

wherein R, R', R" and $n$ are as defined above with a compound capable of reacting with the ester XV such as an alkylating or aralkylating agent or an aldehyde or ketone corresponding to the substituent Y and of introducing into it the group Y as defined above.

Compounds having the formula IV as defined hereinbefore are produced by reacting a compound having the formula:

XVII

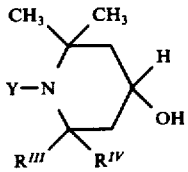

wherein Y, $R^{III}$ and $R^{IV}$ are as defined hereinbefore with an isocyanate having the formula:

$R_{12}(NCO)_q$ wherein $R_{12}$ and $q$ are as defined hereinbefore. The reaction can be effected in a solvent inert under the reaction conditions and in the presence of a strong base.

The present invention still further provides a composition comprising an organic material and a stabilising amount of a compound having the formula I, II or IV as hereinbefore defined.

Compounds of formula I, II or IV, have been found to impart to polyolefines an exceptionally high degree of stability towards deterioration normally induced by the effects of ultra-violet radiation or exposure to heat. Moreover, this improved stability is achieved without affecting the colour properties of the treated polyolefine. The stabilisers of the invention provide effective light and/or heat stabilisation, especially for low- and high-density polyethylene and polypropylene and polystyrene as well as polymers of butene-1, pentene-1, 3-methyl-butene-1, hexene-1, 4-methylpentene-1, 4-methylhexene-1 and 4,4-dimethyl-pentene-1, and also co- and ter-polymers of olefines, particularly of ethylene or propylene.

Other organic materials susceptible to degradiation by the effects of light and the properties of which are improved by the incorporation therein of a compound of formula I, II or IV, include natural and synthetic polymeric materials, for instance natural and synthetic rubbers, the latter including, for example, homo-, co- and ter-polymers of acrylonitrile, butadiene and styrene.

Specific synthetic polymers include polyvinyl chloride, polyvinylidene chloride and vinyl chloride copolymers, polyvinyl acetate as well as condensation polymers derived from ether, ester (derived from carboxylic sulphonic or carbonic acids), amide or urethane groupings. These polymers can, for instance, form the basis of surface coating media such as paints and lacquers having an oil or resin, for instance an alkyd or polyamide resin base.

The amount of the compound of formula I, II or IV, which is incorporated into the organic material in order to achieve maximal protection against degradation by light varies according to the properties of the organic material treated and according to the severity of the light radiation and to the length of exposure. However, for most purposes it is sufficient to use an amount of the compound of formula I, II or IV, within the range of from 0.01% to 5% by weight, more preferably within the range of from 0.1% to 2% by weight based on the weight of untreated organic material.

The compounds may be incorporated into the polymeric material by any of the known techniques for compounding additives with a polymer. For example, in the compound and the polymer may be compounded in an internal mixer. Alternatively, the compound may be added as a solution or slurry in a suitable solvent or dispersant, for instance an inert organic solvent such as methanol, ethanol or acetone to powdered polymer and the whole mixed intimately in a mixer, and the solvent subsequently removed. As a further alternative the compound may be added to the polymer during the preparation of the latter, for instance at the latex stage of polymer production, to provide pre-stablise polymer material.

Optionally, the composition of the invention may contain one or more further additives, especially those used in polymer formulations, such as antioxidants of the phenol or amine type, U.V. absorbers and light protectants, phosphite stabilisers, peroxide decomposers, polyamide stabilisers, basic co-stabilisers, polyvinyl chloride stabilisers, nucleation agents, plasticizers, lubricants, emulsifiers, anti-static agents, flame-protectants, pigments, carbon black, asbestos, glass fibres, kaolin and talc.

The present invention therefore includes binary, tertiary and multi-component compositions containing the stabiliser of formula I, II or IV, together with one or more functional additives for polymers.

Examples of suitable antioxidants are those of the hindered phenol type such as those selected from the following groups:

1. Phenolic compounds having the general formula

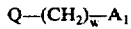

wherein
Q is

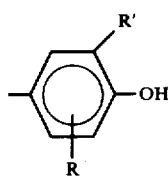

A₁ is —CR(COOR")₂

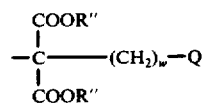

R is hydrogen or lower alkyl
R' is lower alkyl
R" is alkyl group having from 6 – 24 carbon atoms
w is an integer from 0 to 4.

Illustrative examples of the compounds shown above are:
di-n-octadecyl-α-(3,5-di-t-butyl-4-hydroxy-benzyl)malonate
di-n-octadecyl-α-(3-t-butyl-4-hydroxy-5-methylbenzyl-malonte which is disclosed in the Netherlands Pat. No. 6,711,199, Feb. 19, 1968
di-n-octadecylα,α'bis-(3-t-butyl-4-hydroxy-5-methylbenzyl)malonate which is disclosed in the Netherlands Pat. No. 6,803,498, Sept. 18, 1968.

2. Phenolic compounds having the general formula

Illustrative examples of the compounds shown above are:
2,6-di-t-butyl-p-cresol
2-methyl-4,6-di-t-butylphenol and the like
2,6-di-Octadecyl-p-cresol 3. Phenolic compounds having the formula

Illustrative examples of the compounds shown are:
2,2'-methylene-bis(6-t-butyl-4-methylphenol)
2,2'-methylene-bis(6-t-butyl-4-ethylphenol)
4,4'-butylidene-bis(2,6-di-t-butylphenol)
4,4'-(2-butylidene)-bis(2-t-butyl-5-methylphenol)
2,2'-methylene-bis[6-(2-t-methylcyclohexyl)-4-methylphenol
2,2'-methylene-bis(3-t-butyl-5-ethylphenol)
4,4'-methylene-bis(3,5-di-t-butylphenol)
4,4'-methylene-bis(3-t-butyl-5-methylphenol)
2,2'-methylene-bis(3-t-butyl-5-methylphenol)
and the like.

4. Phenolic compounds having the formula:

Illustrative examples of such compounds are:
2,5-di-t-butylhydroquinone
2,6-di-t-butylhydroquinone
2,5-di-t-butyl-4-hydroxyanisole 5. Phenolic compounds having the formula:

Illustrative examples of such compounds are:
4,4'-thiobis-(2-t-butyl-5-methylphenol)
4,4'-thiobis-(2-t-butyl-6-methylphenol)
2,2'-thiobis-(6-t-butyl-4-methylphenol)
4,4'-thiobis-(2-methyl-5-t-butylphenol)

6. Phenolic compounds having the formula

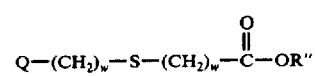

Illustrative examples of such compounds are:
octadecyl-(3,5-dimethyl-4-hydroxybenzylthio)-acetate
dodecyl-(3,5-di-t-butyl-4-hydroxybenzylthio)-propionate 7. Phenolic compounds having the formula

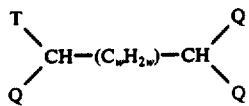

wherein T is hydrogen
R or Q as defined above.

Illustrative examples of such compounds are:
1,1,3-tris(3,5-dimethyl-4-hydroxyphenyl)-propane
1,1,3-tris(5-t-butyl-4-hydroxy-2-methylphenyl)-butane
1,1,5,5-tetrakis-(3'-t-butyl-4'-hydroxy-6'-methylphenyl)-n-pentane 8. Phenolic compounds having the formula:

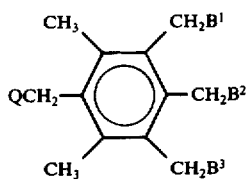

wherein $B^1$, $B^2$ and $B^3$ are hydrogen, methyl or Q, provided that when $B^1$ and $B^3$ are Q then $B^2$ is hydrogen or methyl and when $B^2$ is Q then $B^1$ and $B^3$ are hydrogen or methyl.

Illustrative examples of such compounds are:
1,4-di(3,5-di-t-butyl-4-hydroxybenzyl)-2,3,5,6-tetramethylbenzene
1,3,5-tri(3,5-di-t-butyl-4-hydroxybenzyl)-2,4,6-trimethylbenzene 8. Phenolic compounds having the formula

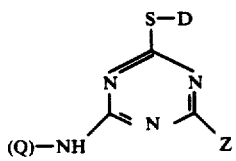

wherein Z is NHQ, —S—D— or —O—Q
D is alkyl group having from 6 - 12 carbon atoms or —($C_wH_{2w}$)—S—R''

Illustrative examples of such compounds are:
2,4-bis-(n-octylthio)-6-(3,5-di-t-butyl-4-hydroxyaniline)-1,3,5-triazine
6-(4-hydroxy-3-methyl-5-t-butylanilino)-2,4-bis-(n-octylthio)-1,3,5-triazine
6-(4-hydroxy-3,5-dimethylanilino)-2,4-bis-(n-octylthio)-1,3,5-triazine
6-(4-hydroxy-3,5-di-t-butylanilino)-2,4-bis-(n-octylthio)-1,3,5-triazine
6-(4-hydroxy-3,5-di-t-butylanilino)-4-(4-hydroxy-3,5-di-t-butylphenoxy)-2-(n-octylthio)1,3,5-triazine
2,4-bis(4-hydroxy-3,5-di-t-butylanilino)-6-(n-octylthio)-1,3,5-triazine The above phenolic triazine stabilizers are more fully described in U.S. Pat. No. 3,255,191.

10. Phenolic compounds having the formula:

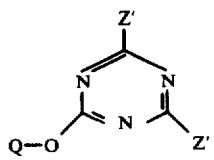

wherein Z' is —O—Q, —S—D or —S—($C_wH_{2w}$)—SD.

Illustrative examples of such compounds are:
2,3-bis-(3,5-di-t-butyl-4-hydroxyphenoxy)-6-(n-octylthio)-1,3,5-triazine
2,4,6-tris(4-hydroxy-3,5-di-t-butylphenoxy)-1,3,5-triazine
6-(4-hydroxy-3,5-di-t-butylphenoxy)-2,4-bis-(n-octylthioethylthio)-1,3,5-triazine
6-(4-hydroxy-3-methylphenoxy)-2,4-bis-(n-octylthio)-1,3,5-triazine
6-(4-hydroxy-3-t-butylphenoxy)-2,4-bis-(n-octylthioethylthio)-1,3,5-triazine
6-(4-hydroxy-3-methyl-5-t-butylphenoxy)-2,4-bis-(n-octylthio)-1,3,5-triazine
2,4-bis-(4-hydroxy-3-methyl-5-t-butylphenoxy)-6-(n-octylthio)-1,3,5-triazine
2,4,6-tris-(4-hydroxy-3-methyl-5-t-butylphenoxy)-1,3,5-triazine
6-(4-hydroxy-3,5-di-t-butylphenoxy)-2,4-bis-(n-octylthiopropylthio)-1,3,5-triazine
6-(4-hydroxy-3,5-di-t-butylphenoxy)-2,4-bis-(n-dodecylthioethylthio)-1,3,5-triazine
2,4-bis-(4-hydroxy-3,5-di-t-butylphenoxy)-6-butylthio-1,3,5-triazine
2,4-bis-(4-hydroxy-3,5-di-t-butylphenoxy)-6-(n-octadecylthio)-1,3,5-triazine
2,4-bis-(4-hydroxy-3,5-di-t-butylphenoxy)-6-(n-dodecylthio)-1,3,5-triazine
2,4-bis-(4-hydroxy-3,5-di-t-butylphenoxy)-6-(n-octylthiopropylthio)-1,3,5-triazine
2,4-bis-(4-hydroxy-3,5-di-t-butylphenoxyl)-6-(n-octylthioethylthio)-1,3,5-triazine
2,4-bis-(4-hydroxy-3,5-di-t-butylphenoxy)-6-(n-octylthioethylthio)-1,3,5-triazine
2,4-bis-(4-hydroxy-3,5-di-t-butylphenoxy)-6-(n-dodecylthioethylthio)-1,3,5-triazine.

The above phenolic triazine stabilizers are more fully described in U.S. Pat. No. 3,255,191.

11. Phenolic compounds having the formula

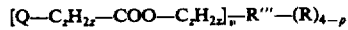

[Q—$C_xH_{2x}$—COO—$C_yH_{2y}$]$_p$—R'''—(R)$_{4-p}$ wherein p is an integer from 2 to 4 and R''' is tetravalent radical selected from aliphatic hydrocarbons having fromm 1 to 30 carbon atoms, aliphatic mono- and dithioethers having from 1 to 30 carbon atoms, aliphatic mono- and diethers having from 1 to 30 carbon atoms and z is an integer from 0 to 6.

Illustrative examples of such compounds are

Sub-class I n-Octadecyl-3-(3,5-di-t-butyl-4-hydroxyphenyl)-propionate
n-Octadecyl-2-(3,5-di-t-butyl-4-hydroxyphenyl)-acetate
n-Octadecyl-3,5-di-t-butyl-4-hydroxyphenylbenzoate
n-Hexyl-3,5-di-t-butyl-4-hydroxyphenylbenzoate
n-Dodecyl-3,5-di-t-butyl-4-hydroxyphenylbenzoate
Neo-dodecyl-3-(3,5-di-t-butyl-4-hydroxyphenyl)-proprionate
Dodecyl-β-(3,5-di-t-butyl-4-hydroxyphenyl)-propionate
Ethyl-α-(4-hydroxy-3,5-di-t-butlphenyl)-isobutyrate
Octadecyl-α-(4-hydroxy-3,5-di-t-butylphenyl)-isobutyrate
Octadecyl-α-(4-hydroxy-3,5-di-t-butylphenyl)-propionate

SUB-CLASS II 2-(n-octylthio)ethyl 3,5-di-t-butyl-4-hydroxybenzoate
2-(n-octylthio)ethyl 3,5-di-t-butyl-4-hydroxyphenylacetate
2-(n-octadecylthio)ethyl 3,5-di-t-butyl-4-hydroxyphenylacetate
2-(n-octadecylthio)ethyl 3,5-di-t-butyl-4-hydroxybenzoate
2-(2-hydroxyethylthio)ethyl 3,5-di-t-butyl-4-hydroxybenzoate
2,2'-Thiodiethanol bis(3,5-di-t-butyl-4-hydroxyphenyl)acetate
Diethyl glycol bis-[3,5-di-t-butyl-4-hydroxyphenyl)propionate]
2-(n-octadecylthio)ethyl 3-(3,5-di-t-butyl-4-hydroxyphenyl)propionate
2,2'-Thiodiethanol-bis-3-(3,5-di-t-butyl-4-hydroxyphenyl)propionate
Stearamido N,N-bis-[ethylene 3-(3,5-di-t-butyl-4-hydroxyphenyl)propionate]
n-Butylimino N,N-bis-[ethylene 3-(3,5-di-t-butyl-4-hydroxyphenyl)propionate]
2-(2-stearoyloxyethylthio)ethyl 3,5-di-t-butyl-4-hydroxybenzoate
2-(2-hydroxyethylthio)ethyl 7-(3-methyl-5-t-butyl-4-hydroxyphenyl)heptanoate
2-(2-stearoyloxyethylthio)ethyl 7-(3-methyl-5-t-butyl-4-hydroxyphenyl)heptanoate

SUB-CLASS III 1,2-propylene glycol bis-[3-(3,5-di-t-butyl-4-hydroxyphenyl)propionate]
Ethylene glycol bis-[3-(3,5-di-t-butyl-4-hydroxyphenyl) propionate]
Neopentylglycol bis-[3-(3,5-di-t-butyl-4-hydroxyphenyl) propionate]
Ethylene glycol bis-(3,5-di-t-butyl-4-hydroxyphenylacetate)
Glycerine-1-n-octadecanoate-2,3-bis-(3,5-di-t-butyl-4-hydroxyphenylacetate
Pentaethylthritol-tetrakis-[3-(3,5-di-t-butyl-4-hydroxyphenyl)propionate]
1,1,1-trimethylol ethane-tris-3-(3,5-di-t-butyl-4-hydroxyphenyl)propionate
Sorbitol hexa-[3-(3,5-di-t-butyl-4-hydroxyphenyl) propionate]
1,2,3-butanetriol tris-[3-(3,5-di-t-butyl-4-hydroxyphenyl)propionate]
2-hydroxyethyl 7-(3-methyl-5-t-butyl-4-hydroxyphenyl) heptanoate
2-stearoyloxyethyl 7-(3-methyl-5-t-butyl-4-hydroxyphenyl)heptanoate
1,6-n-hexanediol-bis[(3',5'-di-t-butyl-4-hydroxyphenyl) propionate]

The above phenolic ester stabilizers of sub-classes I, II and III are more fully described in U.S. Pat. No. 3,330,859, Ser. No. 354,464, filed Mar. 24, 1964 and Ser. No. 359,460, filed Apr. 13, 1964, respectively.

12. Phenolic compounds having the formula $$Q-(CH_2)_x \overset{O}{\underset{OR''}{\overset{\|}{P}}}-OR''$$

where $x$ is an integer of 1 or 2.
Illustrative examples of such compounds are

Di-n-octadecyl 3,5-di-t-butyl-4-hydroxybenzyl-phosphonate
Di-n-octadecyl 3-t-butyl-4-hydroxy-5-methylbenzylphosphonate
Di-n-octadecyl 1-(3,5-di-t-butyl-4-hydroxyphenyl)ethanephosphonate
Di-n-tetradecyl 3,5-di-t-butyl-4-hydroxybenzylphosphonate
Di-n-hexydecyl 3,5-di-t-butyl-4-hydroxybenzylphosphonate
Di-n-docosyl-3,5-di-t-butyl-4-hydroxybenzylphosphonate
Di-n-octadecyl 3,5-di-t-butyl-4-hydroxybenzylphosphonate.

The above di-(higher)alkyl phenolic phosphonates are more fully described in U.S. Pat. No. 3,281,505.

13. Phenolic compounds having the formula $$QW(H_2C)-N \begin{array}{c} O \\ \diagdown \\ \diagup \end{array} \overset{(CH_2)WQ}{\underset{\|}{\overset{|}{N}}} \begin{array}{c} O \\ \diagup \\ \diagdown \end{array} N-(CH_2)WQ$$

wherein W and Q are defined above.
Illustrative examples of such compounds are:
tris-(3,5-di-t-butyl-4-hydroxybenzyl)isocyanurate
tris-(3-t-butyl-4-hydroxy-5-methylbenzyl)isocyanurate.

The above hydroxyphenylalkenyl isocyanurates are more fully described in U.S. Pat. No. 3,531,483.

The above phenolic hydrocarbon stabilizers are known and many are commercially available.

While any of the above mentioned antioxidants can be useful in combination with the ultraviolet light stabilizers of this invention, the preferred antioxidants consist of the hindered phenols in groups 1, 8, 9, 10, 11, 12 and 13 as mentioned above. The most preferred hindered phenols are those of groups 1, 9, 11, 12 and 13.

Further examples of antioxidants are those of the aminoaryl series for instance aniline and naphthylamine derivatives as well as their heterocyclic derivatives such as:
phenyl-1-naphthylamine
phenyl-2-naphthylamine
N,N'-diphenyl-p-phenyldiamine
N,N'-di-sec.butyl-p-phenylenediamine
6-Ethoxy-2,2,4-trimethyl-1,2-dihydroquinoline
6-Dodecyl-2,2,4-trimethyl-1,2-dihydroquinoline
Mono- and di-octyliminodibenzyl and
polymerised 2,2,4-trimethyl-1,2-dihydroquinoline.

Ultraviolet absorbers and light protectants include
a. 2-(2'-hydroxyphenyl)benzotriazoles, for instance 5'-methyl; 3',5'-di-t-butyl; 5'-t-butyl; 5-chloro-3',5'-di-t-butyl; 5-chloro-3'-t-butyl-5'-methyl; 3'-sec. butyl-5'-tert.butyl; 3'-[α-methylbenzyl]-5'-methyl-; 3'-[α-methylbenzyl]-5'-methyl-5-chloro-; 4'-octoxy-; 3',5'-di-t-amyl; 3'-methyl-5'-carbamethoxyethyl; 5-chloro-3',5'-di-t-amyl derivatives.

b. 2,4bis(2'-hydroxyphenyl)-6-alkyl-S-triazines, for instance the 6-ethyl or 6-undecyl derivatives.

c. 2-hydroxybenzophenones, for instance the 4-hydroxy, 4-methoxy, 4-octoxy-, 4-decyloxy-, 4-dodecyloxy-, 4,2', 4'-trihydroxy or 2'-hydroxy-4,4'-dimethoxy derivatives.

d. 1,3-Bis(2'-hydroxybenzoyl)-benzenes for instance, 1,3-bis-(2'-hydroxy-4'-hexyloxybenzoyl)benzene 1,3-bis-(2'-hydroxy-4'-octoxybenzoyl)benzene
1,3-bis-(2'-hydroxy-4'-dodecyloxybenzoyl)benzene e. Aryl esters from optionally substituted benzoic acids such as phenylsalicylate, octylphenylsalicylate, dibenzoyl resorcinol, bis-(4-tert.butylbenzoyl) resorcinol, benzoylresorcinol and 3,5-di-tert.butyl-4-hydroxybenzoic acid-2,4-di-tert.butyl phenyl ester and -octadecyl ester and -2-methyl-4,6-di-tert.butyl phenyl ester.

f. Acrylates, for instance
α-Cyano-β,β-diphenylacrylic acid ethyl- or iso-octyl ester, α-carbomethoxy-cinnamic acid, methyl- or butyl ester and N-(β-carbomethoxyvinyl)-2-methyl indoline.

g. Nickel compounds such as nickel complexes of 2,2'-thiobis-(4-tert.octylphenol), for instance the 1:1 and 1:2 complexes, optionally having other ligands such as n-butylamine, triethanolamine or N-cyclohexyl-diethanolamine; nickel complexes of bis-(4-tert.octylphenyl) sulphone such as the 2:1 complex, optionally having other ligands such as 2-ethylcaproic acid; nickel dibutyl dithiocarbamates; nickel salts of 4-hydroxy-3,5-di-tert. butylbenzyl-phosphonic acid mono-alkyl esters such as the methyl-, ethyl- or butyl esters; the nickel complex of 2-hydroxy-4-methyl-phenyl-undecylketonoxime; and nickel-3,5-di-tert.butyl-4-hydroxy benzoate, and h. Oxalic acid diamides, for instance
4,4'-dioctyloxyoxanilide
2,2'-dioctyloxy-5,5'-di-tert.butyl-oxanilide
2,2'-di-dodecyloxy-5,5'-di-tert.butyl oxanilide
2-ethoxy-5-tertiarybutyl-2'-ethyl-oxanilide
2-ethoxy-2'-ethyl-oxanilide
mixtures of o- and p-methoxy and ethoxy-di-substituted oxanilides and the compound of formula:

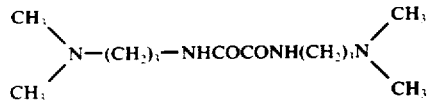

Phosphite stabilisers include triphenyl phosphite, diphenylalkyl phosphites, phenyl dialkyl phosphites, trinonylphenyl phosphite, trilauryl phosphite, trioctadecyl phosphite, 3,9-di-isodecyloxy-2,4,8,10-tetraoxa-3,9-diphosphaspiro-(5,5)-undecane and tri-(4-hydroxy-3,5-di-tert.butylphenyl)phosphite.

Peroxide-decomposing compounds for polyolefins include esters of β-thiodipropionic acids, for instance the lauryl-, stearyl-, myristyl- or tridecyl esters, salts of mercaptobenzimidazoles such as the zinc salt and diphenylthiourea.

Suitable polyamide stabilisers include copper salts in combination with iodides and/or further phosphorus compounds and salts of bivalent manganese.

Basic co-stabilisers are, for example, polyvinylpyrrolidone, melamine, benzoguanamine, triallyl cyanurate, dicyandiamide, urea derivatives, hydrazine derivatives, amines, polyamides, polyurethanes, alkali and alkaline earth salts of higher saturated or unsaturated fatty acids such as calcium stearate.

Polyvinyl chloride stabilisers include organotin compounds, organo lead compounds and Ba/Cd salts of fatty acids.

Examples of nucleation agents are 4-tert.butyl benzoic acid, adipic acid and diphenylacetic acid.

As with the compound of formula I, II or IV any further additive is advantageously employed in a proportion within the range of from 0.01% to 5% by weight, based on the weight of untreated polymeric material.

In binary combinations with one or more antioxidants listed above or in tertiary combinations with such antioxidants and U.V. absorbers listed above, the compounds of formula I, II or IV provide very effective stabiliser packages in polyolefine formulations.

Some Examples will now be given. Parts and percentages are by weight unless otherwise stated.

EXAMPLE 1

A mixture of 10.26 parts of 1,2,2,6,6-pentamethyl-piperidin-4-ol, 6.06 parts of sebacic acid and 1.0 parts of tetra-n-butyl titanate in 100 parts of xylene was heated under reflux conditions for 60 hours. Removal of the xylene by distillation under reduced pressure gave an oily solid which was heated under reflux conditions with 0.5 parts of sodium carbonate and 0.5 parts of carbon in 25 parts of water for 1 hour.

Removal of the water by distillation under reduced pressure gave a black residue which was repeatedly extracted with ether. The combined ether extracts were dried and the ether removed by distillation under reduced pressure to give a yellow oil which was distilled under reduced pressure to give 5.0 parts of bis(1,2,2,6,6-pentamethyl-4-piperidinyl) sebacate as a colorless oil having a boiling point of 220°-2° C at 0.2 mm of Hg and the following elemental analysis by weight:

|  | Found | Required | (for $C_{30}H_{56}N_2O_4$) |
|---|---|---|---|
| Carbon | 70.60 % | 70.82 % | |
| Hydrogen | 11.00 % | 11.10 % | |
| Nitrogen | 4.81 % | 5.51 % | |

Table I gives a list of esters prepared using the procedure of Example 1.

TABLE I
| Example No. | R₁ | R₂ | R₃ | m.p. or b.p. °C at m.m. | Molecular Formula | REQUIRED (%) C | H | N | FOUND (%) C | H | N |
|---|---|---|---|---|---|---|---|---|---|---|---|
| 2 | CH₃ | H | 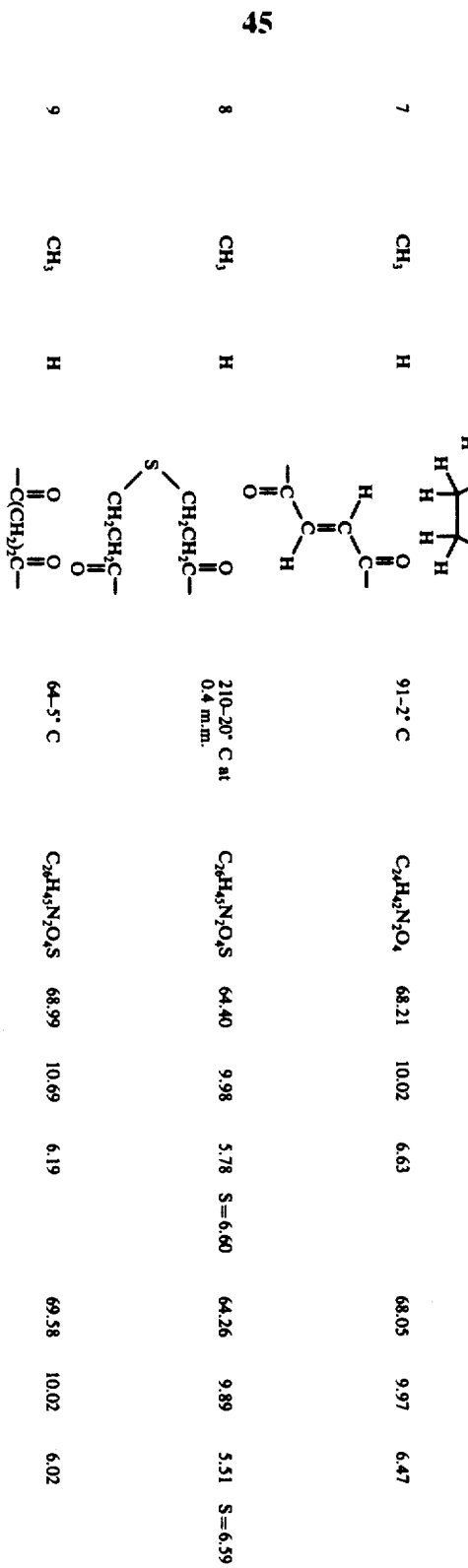 | 88° C | C₂₁H₃₃NO₂ | 76.09 | 10.03 | 4.23 | 76.36 | 9.90 | 3.99 |
| 3 | CH₂=CH.CH₂— | H | | 130° C at 0.05 m.m. Hg. | C₁₉H₃₃NO₂ | 74.22 | 10.82 | 4.56 | 74.86 | 10.65 | 4.26 |
| 4 | CH₃ | H | | 200° C at 0.1 m.m. Hg. | C₂₈H₅₃NO₂ | 77.18 | 12.26 | 3.21 | 78.10 | 12.30 | 3.06 |
| 5 | CH₃ | H | | 81–3° C at 0.05 m.m. Hg. | C₁₄H₂₇NO₂ | 69.67 | 11.27 | 5.80 | 70.16 | 11.37 | 5.90 |
| 6 | CH₃ | H | | 228–30° C at 0.1 m.m. Hg. | C₂₈H₅₀N₂O₄ | 70.25 | 10.53 | 5.85 | 70.26 | 10.44 | 5.38 |
| 7 | CH₃ | H | | 91–2° C | C₂₄H₄₂N₂O₄ | 68.21 | 10.02 | 6.63 | 68.05 | 9.97 | 6.47 |
| 8 | CH₃ | H | | 210–20° C at 0.4 m.m. | C₂₆H₄₅N₂O₄S | 64.40 | 9.98 | 5.78 S=6.60 | 64.26 | 9.89 | 5.51 S=6.59 |
| 9 | CH₃ | H | | 64–5° C | C₂₆H₄₅N₂O₄S | 68.99 | 10.69 | 6.19 | 69.58 | 10.02 | 6.02 |

TABLE I-continued

| Example No. | R₁ | R₂ | R₃ | m.p. or b.p. °C at m.m. | Molecular Formula | REQUIRED (%) C | H | N | FOUND (%) C | H | N |
|---|---|---|---|---|---|---|---|---|---|---|---|
| 10 | CH₃ | H | C₆H₅—CH=CHC(=O)— | 57° C. | C₁₉H₂₇NO₂ | 75.71 | 9.03 | 4.65 | 75.50 | 8.97 | 4.71 |
| 11 | CH₃ | H | C₆H₅—CH₂—C(=O)— | 120° C. at 0.2 m.m. Hg. | C₁₈H₂₇NO₂ | 74.70 | 9.40 | 4.84 | 74.99 | 9.70 | 4.85 |
| 12 | CH₃ | H | 4-CH₃—C₆H₄—C(=O)— | 148° C. at 0.4 m.m. Hg. | C₁₈H₂₇NO₂ | 74.70 | 9.40 | 4.84 | 74.98 | 9.42 | 4.70 |
| 13 | CH₃ | H | 4-CH₃O—C₆H₄—C(=O)— | 51° C. | C₁₈H₂₇NO₃ | 70.79 | 8.91 | 4.59 | 70.49 | 8.71 | 4.50 |
| 14 | CH₃ | H | 4-Cl—C₆H₄—C(=O)— | 147° C. at 0.1 m.m. Hg. | C₁₇H₂₄NO₂Cl | 66.00 | 7.81 | 4.52 Cl=11.44 | 65.98 | 7.65 | 4.53 Cl=11.5 |
| 15 | CH₃ | H | 2-Cl—C₆H₄—C(=O)— | 152.4° C. at 0.2 m.m. Hg. | C₁₇H₂₄NO₂Cl | 66.00 | 7.81 | 4.52 Cl=11.44 | 65.89 | 7.65 | 4.53 Cl=11.56 |
| 16 | CH₃ | H | CH₃(CH₂)₃CHC(=O)— with CH₂CH₃ side chain | 100° C. at 0.2 m.m. Hg. | C₁₈H₃₅NO₂ | 72.68 | 11.68 | 4.71 | 72.53 | 11.96 | 4.50 |
| 17 | CH₃ | H | CH₂=CH—C(=O)— | 65° C. at 0.4 m.m. Hg. | C₁₃H₂₃NO₂ | 69.29 | 10.29 | 6.22 | 69.64 | 10.30 | 6.15 |

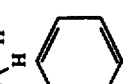

TABLE I-continued

| Example No. | R₁ | R₂ | R₃ | m.p. or b.p. °C at m.m. | Molecular Formula | ANALYSIS REQUIRED (%) | | | | FOUND (%) | | |
|---|---|---|---|---|---|---|---|---|---|---|---|---|
| | | | | | | C | H | N | | C | H | N |
| 28 | CH₃ | H | 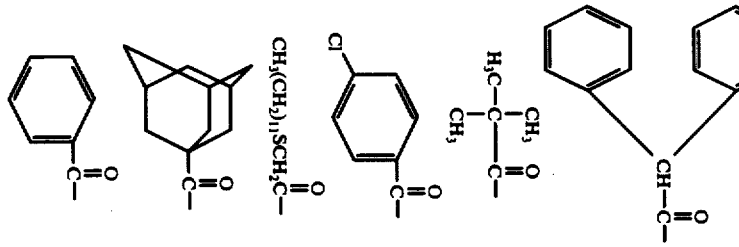 | 69–70° C | C₂₇H₃₁NO₂ | 78.87 | 8.55 | 3.83 | | 79.38 | 8.80 | 3.69 |
| 29 | CH₃ | H | (diphenyl-CH-C(=O)-) | | C₁₇H₂₉NO₂ | 70.54 | 11.45 | 5.48 | | 69.99 | 11.24 | 5.25 |
| 30 | CH₃(CH₂)₁₁— | H | (4-Cl-C₆H₄-C(=O)-) | 56° C | C₂₈H₄₆NO₂Cl | 72.60 | 9.90 | 3.02 Cl=7.66 | | 71.98 | 10.19 | 3.01 Cl=7.35 |
| 31 | CH₃ | H | (CH₃(CH₂)₁₁SCH₂-C(=O)-) | 90° C at 0.1 m.m. Hg | C₂₄H₄₇NO₂S | 69.70 | 11.45 | 3.39 | | 69.69 | 11.48 | 3.31 |
| 32 | CH₃ | H | (adamantyl-C(=O)-) | 200° C at 0.2 m.m. Hg | C₂₁H₃₅NO₂ | 75.63 | 10.58 | 4.20 | | 75.94 | 10.30 | 3.93 |
| 33 | CH₃(CH₂)₁₇— | H | (C₆H₅-C(=O)-) | 119° C | C₃₄H₅₉NO₂ | Purified by chromatography | | | | MOLECULAR WEIGHT = 513 FOUND (FROM MASS SPECTROMETRY = 513) | | |

EXAMPLE 34

A solution of 17.10 parts of 1,2,2,6,6-pentamethyl-piperidin-4-ol in 50 parts of dry benzene was stirred at 15°-20° C whilst adding 6.0 parts of sebacoyl chloride dropwise over 15 minutes. The mixture was stirred for a further 12 hours at room temperature after which the 1,2,2,6,6-pentamethylpiperidin-4-ol hydrochloride formed during the reaction was filtered off. The benzene was removed by distillation under reduced pressure to give a yellow oil, which was distilled under reduced pressure to give bis-(1,2,2,6,6-pentamethyl-4-piperidinyl)sebacate as a colorless oil having a boiling point of 218°-20° C at 0.4 mm of Hg and the following elemental analysis by weight:

|  | Found | Required (for $C_{30}H_{56}N_2O_4$) |
|---|---|---|
| Carbon | 70.99 % | 70.82 % |
| Hydrogen | 10.97 % | 11.10 % |
| Nitrogen | 5.26 % | 5.51 % |

Table 2 gives a list of esters prepared using the procedure of Example 34.

was fractionally distilled under reduced pressure to yield 6.40 parts of 1,2,2,6,6-pentamethylpiperidinyl-4-benzoate having a boiling pouint of 126° C at 0.1 mm of Hg. and the following elemental analysis by weight:

|  | Found | Required (for $C_{17}H_{25}NO_2$) |
|---|---|---|
| Carbon | 74.35% | 74.14% |
| Hydrogen | 9.23% | 9.15% |
| Nitrogen | 5.13% | 5.09% |

EXAMPLE 42

A mixture of 17.10 parts of 1,2,2,6,6-pentamethyl-piperidin-4-ol, 14.60 parts of methyl-$\beta$-(3,5-di-t-butyl-4-hydroxyphenyl) propionate and 1.0 part of lithium amide was heated together to 130° C. Water pump vacuum was then applied to the reaction mixture whilst maintaining the temperature at 125°-135° C for 3 hours. The temperature of the reaction mixture was then raised to 160° C and high vacuum (0.5-1 mm Hg) was applied for 1 hour. The reaction mixture was cooled, dissolved in chloroform and filtered. Removal of the chloroform

TABLE 2

| example | $R_1$ | $R_2$ | $R_3$ | m.p. or b.p. ° C. at m.m. | Molecular Formula | Required (%) C | Required (%) H | Required (%) N | Found (%) C | Found (%) H | Found (%) N |
|---|---|---|---|---|---|---|---|---|---|---|---|
| 35 | $CH_3$ | H | (thiophene-2,5-dicarbonyl) | Purified by chromatography | $C_{26}H_{42}N_2O_4S$ |  |  | 5.86 |  |  | 5.64 |
| 36 | $CH_3$ | H | −C(O)−C(O)− | 118° C. | $C_{22}H_{40}N_2O_4$ | 66.63 | 10.17 | 7.06 | 66.94 | 10.22 | 6.95 |
| 37 | $CH_3$ | H | (isophthaloyl) | 123° C. | $C_{28}H_{44}N_2O_4$ | 70.15 | 9.38 | 5.93 | 70.75 | 9.68 | 5.69 |
| 38 | $CH_3$ | H | (1-naphthoyl) | 75-6° C. | $C_{21}H_{27}NO_2$ | 77.50 | 8.36 | 4.30 | 77.78 | 8.45 | 4.06 |
| 39 | $CH_3$ | H | $CH_3-C(O)-$ | 138° C. at 12 m.m.Hg. | $C_{12}H_{23}NO_2$ | 67.57 | 10.87 | 6.57 | 67.90 | 10.72 | 6.53 |
| 40 | $CH_3$ | H | (3,5-di-t-butyl-4-hydroxybenzoyl) | 142° C. | $C_{25}H_{41}NO_3$ | 74.40 | 10.24 | 3.47 | 74.80 | 9.99 | 3.43 |

EXAMPLE 41

A mixture of 17.10 parts of 1,2,2,6,6-pentamethyl-piperidin-4-ol, 13.60 parts of methyl benzoate and 2.0 parts of lithium amide was heated at 160° C for six hours with removal of the methyl alcohol formed by distillation. Water pump vacuum was applied and heated continued for a further two hours; on cooling the residue was dissolved in chloroform and filtered to remove the lithium amide. The chloroform was removed by distillation under reduced pressure to give a yellow oil which by distillation under reduced pressure gave a brown oil which, when triturated with ether, gave a white solid which was collected by filtration, washed well with ether and dried to give 16.0 parts of 1,2,2,6,-pentamethylpiperidinyl-4-$\beta$-(3',5' di-t-butyl-4'-hydroxyphenyl) propionate as its bicarbonate salt having a melting point of 210°-11° C., and the following elemental analysis by weight:

|  | Found | Required (for $C_{28}H_{47}NO_6$) |
|---|---|---|
| Carbon | 68.90% | 68.10% |
| Hydrogen | 9.56% | 9.60% |
| Nitrogen | 2.91% | 2.84% |

EXAMPLE 43

15.0 parts of the product from Example 2 were dissolve in water and neutralised with sodium hydroxide solution. The aqueous solution was extracted with ether, the combined ether extracts were dried over anhydrous magnesium sulphate. The ether was removed by distillation under reduced pressure to give a white solid which was recrystallised from ethanol to give 9.30 parts of 1,2,2,6,6-pentamethylpiperidinyl-4-β-(3',5'-di-t-butyl-4'-hydroxyphenyl) propionate having a melting point of 124°-5° C and the following elemental analysis by weight:

|  | Found | Calculated (for $C_{27}H_{45}NO_3$) |
|---|---|---|
| Carbon | 75.00 | 75.30 |
| Hydrogen | 10.50 | 10.20 |
| Nitrogen | 3.50 | 3.30. |

EXAMPLE 44

A mixture of 10.26 parts of 1,2,2,6,6-pentamethylpiperidin-4-ol, 5.04 parts of trimethyl trimesate and 0.20 parts of lithium amide in 100 parts of xylene was heated at 137° C for 7 hours. The methyl alcohol formed during the reaction being removed by distillation. The cooled reaction mixture was filtered to remove the lithium amide and the xylene solvent removed by distillation under reduced pressure. Purification of the residue by preparative thin layer chromatography yielded dimethyl(1,2,2,6,6-pentamethylpiperidinyl-4) trimesate having the following molecular weight:

| Found (from mass spectrometry) | 391 |
|---|---|
| Required (for $C_{21}H_{29}NO_6$) | 391 | and methylbis(1,2,2,6,6-pentamethylpiperdinyl-4) trimesate having the following molecular weight:

| Found (from mass spectrometry) | 530 |
|---|---|
| Required (for $C_{30}H_{46}N_2O_6$) | 530. |

EXAMPLE 45

A mixture of 16.4 parts of 1,2,2,6,6-pentamethylpiperidin-4-ol, 6.27 parts of methyl isocyanate and 0.5 parts of 1,4-diazabicyclo[2,2,2]octane was refluxed in 150 parts of dry benzene for 24 hours. Removal of the benzene solvent by distillation under reduced pressure yielded an oily solid which was poured on to 200 parts of water and allowed to stand for 24 hours. The solid formed was collected by filtration, dried and crystallised from n-hexane to give 14.2 parts of 4-methylcarbamoyloxy-1,2,2,6,6-pentamethylpiperidine having a melting point of 96°-7° C. and the following elemental analysis by weight:

Table 3 gives a list of carbamoyloxy esters prepared using the procedure of Example 45.

|  | Found | Required (for $C_{12}H_{24}N_2O_2$) |
|---|---|---|
| carbon | 63.28% | 63.12% |
| hydrogen | 10.70% | 10.59% |
| nitrogen | 12.09% | 12.27% |

TABLE 3

| Ex. | $R_1$ | $R_2$ | $R_3$ | m.p. or b.p. ° C. at m.m. | Molecular Formula | Required (%) C | H | N | Found (%) C | H | N |
|---|---|---|---|---|---|---|---|---|---|---|---|
| 46 | $CH_3$ | H | $CH_3(CH_2)_5NHC(=O)-$ | 63° C. | $C_{17}H_{34}N_2O_2$ | 68.41 | 11.48 | 9.39 | 68.17 | 11.32 | 9.16 |
| 47 | $CH_3$ | H | $CH_3(CH_2)_7NHC(=O)-$ | 56-7° C. | $C_{29}H_{58}N_2O_2$ | 74.62 | 12.52 | 6.00 | 74.58 | 12.34 | 5.96 |
| 48 | $CH_3$ | H | $CH_2=CH\cdot CH_2NHC(=O)-$ | 62° C. | $C_{14}H_{26}N_2O_2$ | 66.11 | 10.30 | 11.01 | 66.40 | 10.27 | 10.92 |
| 49 | $CH_3$ | H | cyclohexyl-NHC(=O)- | 184-6° C. at 2 m.m. Hg. | $C_{17}H_{32}N_2O_2$ | 68.88 | 10.88 | 9.45 | 68.98 | 10.84 | 9.43 |
| 50 | $CH_3$ | H | phenyl-NHC(=O)- | 109-10° C. | $C_{17}H_{26}N_2O_2$ | 70.31 | 9.02 | 9.65 | 70.61 | 8.80 | 9.53 |
| 51 | $CH_3$ | H | (4-methylphenyl)-NHC(=O)- | 106-7° C. | $C_{18}H_{28}N_2O_2$ | 71.02 | 9.27 | 9.20 | 71.42 | 9.41 | 9.02 |
| 52 | $CH_3$ | H | (4-chlorophenyl)-NHC(=O)- | 121° C. | $C_{17}H_{25}N_2O_2Cl$ | 62.86 | 7.70 | 8.68 | 62.92 | 7.75 | 8.87 |

TABLE 3-continued

| Ex. | $R_1$ | $R_2$ | $R_3$ | m.p. or b.p. °C. at m.m. | Molecular Formula | Required (%) C | Required (%) H | Required (%) N | Found (%) C | Found (%) H | Found (%) N |
|---|---|---|---|---|---|---|---|---|---|---|---|
| 53 | $CH_3$ | H | 1-naphthyl-NH—CO— | 129° C. | $C_{21}H_{28}N_2O_2$ | 74.08 | 8.29 | 8.23 | 74.37 | 8.07 | 8.41 |
| 54 | $CH_3$ | H | —CNH(CH$_2$)$_6$NHC— (diamide) | 101–4° C. | $C_{28}H_{54}N_4O_4$ | 65.84 | 10.66 | 10.97 | 65.86 | 10.40 | 10.64 |
| 55 | $CH_3$ | H | —CHN—(4-methylphenylene)—NHC— | 163–5° C | $C_{29}H_{48}N_4O_4$ | 67.41 | 9.36 | 10.84 | 67.21 | 9.52 | 10.83 |
| 56 | $CH_3$ | H | —OCHN—phenylene—CH$_2$—phenylene—NHCO— | 183° C | $C_{35}H_{52}N_4O_4$ | 70.91 | 8.84 | 9.45 | 70.64 | 8.79 | 9.24 |
| 57 | $CH_3$ | H | 1,5-naphthylene bis (—NH—CO— / —OCNH—) | 178° C | $C_{32}H_{48}N_4O_4$ | 69.53 | 8.75 | 10.14 | 70.39 | 8.71 | 9.86 |
| 58 | $CH_2=CH.CH_2—$ | H | cyclohexyl-NHC(O)— | 165° C at 0.05 m.m. Hg | $C_{19}H_{34}N_4O_4$ | 70.76 | 10.63 | 8.69 | 70.64 | 10.80 | 9.04 |
| 59 | $CH_2=CH.CH_2—$ | H | —CHN(CH$_2$)$_6$NHC— | | | | | | | | |
| 60 | $CH_3CH_2CH_2—$ | H | phenyl-NHC(O)— | | | | | | | | |
| 61 | phenyl-CH$_2$— | H | 4-chlorophenyl-NHC(O)— | | | | | | | | |

EXAMPLE 62

A mixture of 28.3 parts of 2,2,6,6-tetramethyl-4-piperidinyl-n-octanoate and 8.55 parts of benzyl bromide was stirred and heated at 105° C for 72 hours. Ether was added to the cooled reaction mixture and the 2,2,6,6-tetramethyl-4-piperidinyl-n-octanoate hydrobromide formed during the reaction was filtered off. The ether solvent was removed by distillation under reduced pressure and the residue distilled under reduced pressure to give 16.40 parts of 1-benzyl-2,2,6,6-tetramethyl-4-piperidinyl-n-octanoate having a boiling point of 180° C at 0.1 mm of Hg and the following elemental analysis by weight:

|  | Found | Required (for $C_{24}H_{39}NO_2$) |
|---|---|---|
| Carbon | 77.46% | 77.16% |
| Hydrogen | 10.50% | 10.52% |
| Nitrogen | 3.86% | 3.75% |

Table 4 gives a list of esters prepared using the procedure of Example 62.

TABLE 4

| Ex. No. | $R_1$ | $R_2$ | $R_3$ | m.p. or b.p. °C at m.m. | Molecular Formula | REQUIRED (%) C | H | N | FOUND (%) C | H | N |
|---|---|---|---|---|---|---|---|---|---|---|---|
| 63 | phenyl-CH$_2$— | H | —C(=O)(CH$_2$)$_8$C(=O)— | 98-9° C | $C_{42}H_{64}N_2O_4$ | 76.32 | 9.76 | 4.24 | 76.04 | 9.49 | 4.04 |
| 64 | CH$_3$CH$_2$O-C(=O)-CH$_2$— | H | 4-CH$_3$O-C$_6$H$_4$-C(=O)— | 191-2° C at 0.1 m.m. Hg | $C_{21}H_{31}NO_5$ | 66.82 | 8.28 | 3.71 | 66.81 | 8.52 | 3.84 |
| 65 | CH$_2$=CH CH$_2$— | H | CH$_3$(CH$_2$)$_6$C(=O)— | 142-4° C at 0.2 m.m. Hg | $C_{20}H_{37}NO_2$ | 74.25 | 11.53 | 4.33 | 74.06 | 11.36 | 4.32 |
| 66 | CH≡C.CH$_2$— | H | 4-CH$_3$O-C$_6$H$_4$-C(=O)— | 68-9° C | $C_{20}H_{27}NO_3$ | 72.92 | 8.26 | 4.25 | 72.82 | 8.28 | 4.55 |
| 67 | CH$_2$=CHCH$_2$— | H | C$_6$H$_5$-C(=O)— | 150° C at 0.05 m.m. Hg | $C_{19}H_{27}NO_2$ | 75.71 | 9.03 | 4.65 | 75.58 | 9.25 | 4.45 |
| 68 | CH$_2$=CHCH$_2$— | H | —C(=O)(CH$_2$)$_8$C(=O)— | 250° C at 0.5 m.m. Hg | $C_{34}H_{60}N_2O_4$ | 72.81 | 10.78 | 4.99 | 73.07 | 10.60 | 4.77 |
| 69 | CH$_2$—CH.CH$_2$ (epoxide) | H | cyclohexyl-C(=O)— | 139-42° C at 0.2 m.m. Hg | $C_{19}H_{33}NO_3$ | 70.55 | 10.28 | 4.33 | 70.37 | 10.38 | 4.39 |

EXAMPLE 70

A mixture of 17.10 parts of 1,2,2,6,6-pentamethyl-piperidin-4-ol and 3.50 parts of metallic sodium in 125 parts of toluene was heated under reflux conditions for 24 hours. The toluene solution was decanted off from the excess sodium and then refluxed for a further 24 hours with 36.60 parts of n-octadecyl bromide. The cooled solution was filtered to remove the sodium bromide which was formed during the reaction and the toluene solvent was removed by distillation under reduced pressure. Fractional distillation of the residue gave 4-octadecyloxy-1,2,2,6,6-pentamethylpiperidine having a boiling point of 184° C at 0.25 m.m of Hg. and the following elemental analysis by weight:

| | Found | Required (for $C_{28}H_{57}NO$) |
|---|---|---|
| Carbon | 78.66% | 79.36% |
| Hydrogen | 13.77% | 13.56% |
| Nitrogen | 2.99% | 3.31% |

Table 5 gives a list of ethers prepared using the procedure of Example 70.

TABLE 5

| Ex. No. | $R_1$ | $R_2$ | $R_3$ | m.p. or b.p. °C at m.m. Hg | Molecular Formula | REQUIRED (%) C | H | N | FOUND (%) C | H | N |
|---|---|---|---|---|---|---|---|---|---|---|---|
| 71 | CH$_3$ | H | CH$_2$=CH.CH$_2$— | | | | | | | | |
| 72 | CH$_3$ | H | C$_6$H$_5$-CH$_2$— | | | | | | | | |
| 73 | CH$_3$ | H | CH$_3$(CH$_2$)$_{11}$— | | | | | | | | |
| 74 | CH$_3$ | H | —(CH$_2$)$_4$— | m.p. 62-63 | $C_{24}H_{48}N_2O_2$ | 72.74 | 12.09 | 7.07 | 73.00 | 11.94 | 6.85 |
| 75 | CH$_3$ | H | (H=CCH$_2$— | b.p. 0.3 mm 73-74 | $C_{13}H_{23}NO$ | 74.59 | 11.07 | 6.69 | 74.48 | 10.95 | 6.41 |
| 76 | CH$_3$ | H | CH$_3$(CH$_2$)$_3$— | b.p. 19 mm 123-124 | $C_{14}H_{29}NO$ | 73.95 | 12.85 | 6.16 | 74.05 | 12.93 | 6.10 |

EXAMPLE 77

3.23 Parts of 1-allyl-2,2,6,6-tetramethyl-4-piperidinyl-t-n-octanoate in 50 parts of ethyl alcohol was hydrogenated at room temperature and 1 atmosphere pressure using 0.1 parts of 5% palladium on charcoal as the catalyst. The reaction mixture was filtered to remove the catalyst and the ethyl alcohol removed by distillation under reduced pressure to give 2.90 parts of 1-n-propyl-2,2,6,6-tetramethyl-4-piperidinyl-n-octanoate having a boiling point of 128° C at 0.05 mm of Hg and the following elemental analysis by weight:

|  | Found | Required (for $C_{20}H_{39}NO_2$) |
|---|---|---|
| Carbon | 73.50% | 73.79% |
| Hydrogen | 12.26% | 12.08% |
| Nitrogen | 4.31% | 4.30% |

Table 6 gives a list of compounds prepared using the procedure of Example 77

TABLE 6

| Ex. No. | $R_1$ | $R_2$ | $R_3$ | m.p. or b.p. ° C m.m. | Molecular Formula | ANALYSIS REQUIRED (%) C H N | FOUND (%) C H N |
|---|---|---|---|---|---|---|---|
| 78 | $CH_3CH_2CH_2-$ | H | $CH_3CH_2CH_2-$ | | | | |
| 79 | $CH_3$ | H | $CH_3CH_2CH_2-$ | | | | |

EXAMPLE 80 a. A mixture of 2.83 parts of 2,2,6,6-pentamethyl-4-piperidinyl-n-octanoate and 1.50 parts by volume of liquid ethylene oxide was charged into a 50 ml autoclave previously cooled to $-50°$ C. A pressure of 100 atmosphere of nitrogen was applied and the autoclave heated at 200° C, with stirring, for three hours. Fractional distillation of the cooled reaction mixture yielded 2.30 parts of 1-(2'-hydroxyethyl)-2,2,6,6-tetramethyl-4-piperidinyl-n-octanoate having a boiling point of 186°-7° C at 0.25 mm of Hg and the following elemental analysis by weight:

|  | Found | Required (for $C_{19}H_{37}NO_3$) |
|---|---|---|
| Carbon | 69.93% | 69.68% |
| Hydrogen | 11.09% | 11.39% |
| Nitrogen | 4.37% | 4.28% | b. A mixture of 11.32 parts of 2,2,6,6-tetramethyl-4-piperidinyl-n-octanoate and 2.50 parts of 2-bromoethanol was stirred at 100° C for 65 hours. Petroleum ether (bp 40°-60° C) was added to the cooled reaction mixture and the 2,2,6,6-tetramethylpiperidinyl-4-n-octanoate hydrobromide formed during the reaction was filtered off. The petroleum ether solvent was removed by distillation under reduced pressure and the residue distilled to yield ]-(2'-hydroxethyl)2,2,6,6,-tetramethyl-4-piperidinyl-n-octanoate having a boiling point of 176° C at 0.2 mm of Hg. This sample was identical to that prepared under Example 80a.

EXAMPLE 81

A mixture of 11.45 parts of 4-phenylcarbamoyloxy-2,2,6,6-tetramethylpiperidine and 60 parts of styrene ocide in 60 parts of n-hexanol was heated under reflux conditions for 18 hours. The n-hexanol solvent and unreacted styrene oxide were removed by distillation under reduced pressure to yield a pale yellow crystalline solid. Purification by trituration with hot petroleum ether (b.p. 60°-80° C) yielded 4-phenylcarbamoyloxy-1-[2'-hydroxy-2'-phenylethyl]-2,2,6,6-tetramethylpiperidine having a melting point of 186°-7° C with the following elemental analysis by weight:

|  | Found | Required (for $C_{24}H_{32}N_2O_3$) |
|---|---|---|
| Carbon | 72.51% | 72.70% |
| Hydrogen | 7.92% | 8.13% |
| Nitrogen | 6.91% | 7.06% |

EXAMPLE 82

A mixture of 5.61 parts of 2,2,6,6-tetramethyl-4-piperidin-n-octanoate and 5.0 parts of propylene oxide were charged to an autoclave. A pressure of 100 atmospheres nitrogen was applied. The mixture was heated at 200° C for 3 hours. Fractionation under reduced pressure gave a main fraction b.p. 160°-183° C at 0.1 mm. which after passing down an alumina type H column eluting with chloroform yielded a pale yellow semi-solid 1-(2'-hydroxypropyl)-2,2,6,6-tetramethyl-4-piperidin-n-octanoate having the following elemental analysis by weight:

|  | Found | Required (for $C_{20}H_{39}NO_3$) |
|---|---|---|
| Carbon | 70.20% | 70.34& |
| Hydrogen | 11.45% | 11.51% |
| Nitrogen | 3.89% | 4.10% |

EXAMPLE 83

A mixture of 3.27 parts of the product from Example 80 a., 0.60 parts of acetic acid and 0.1 parts of tetra-n-butyl titanate in 40 parts of xylene was heated under reflux conditions for 24 hours. The xylene solvent was removed by distillation under reduced pressure and the residue fractionally distilled to give 1-(2'-acetoxyethyl)-2,2,6,6-tetramethyl)-4-piperidinyl-n-octanoate having a boiling point of 190°-2° C at 1 m.m. Hg and the following elemental analysis by weight:

|  | Found | Required (for $C_{21}H_{39}NO_4$) |
|---|---|---|
| Carbon | 68.17% | 68.25% |
| Hydrogen | 10.65% | 10.64% |
| Nitrogen | 3.36% | 3.79% |

EXAMPLE 84

A mixture of 3.27 parts of the product from Example 78 a., 0.63 parts of methyl isocyanate and 0.1 parts of 1,4-diazabicyclo[2,2,2] octane in 30 parts of dry benzene was heated under reflux conditions for 24 hours. The benzene solvent was removed by distillation under reduced pressure and the residue crystallised from aqueous ethyl alcohol to give 1-(2'-methylcarbamoyloxyethyl)-2,2,6,6-tetramethyl]-4-piperidinyl-n-octanoate having a melting point of 61°-3° C and the following elemental analysis by weight:

|  | Found | Required (for $C_{21}H_{40}N_2O_4$) |
|---|---|---|
| Carbon | 65.72 % | 65.59 % |
| Hydrogen | 10.37 % | 10.48 % |
| Nitrogen | 7.11 % | 7.28 % |

EXAMPLE 85

A mixture of 3.0 parts of the product from Example 81, 0.90 parts of phenyl isocyanate and 0.1 parts of 1,4-diazabicyclo[2,2,2]octane in 25 parts of dry benzene was heated under reflux conditions for 24 hours. The benzene solvent was removed by distillation under reduced pressure and the residue crystallised from petroleum ether (b.p. 60°-80° C) to give 4-phenylcarbamoyloxy-1-[2'-(phenylcarbamoyloxy)-2'-phenylethyl]2,2,6,6-tetramethylpiperidine having a melting point of 173° C and the following elemental analysis by weight:

|  | Found | Required (for $C_{31}H_{37}N_3O_4$) |
|---|---|---|
| Carbon | 72.65 % | 72.21 % |
| Hydrogen | 7.22 % | 7.23 % |
| Nitrogen | 7.97 % | 8.15 %. |

EXAMPLE 86

A mixture of 3.14 parts of 2,2,6,6-tetramethylpiperidin-4-ol and 3.50 parts of acetic anhydride was heated on a steam bath for one hour. After this time 20 parts of water were added and heating continued for a further one hour. The solution was carefully neutralised with a saturated solution of sodium bi-carbonate and then ether extracted. The combined ether extracts were washed twice with 5% sodium bi-carbonate solution and twice with brine, the ether solution was then dried over anhydrous magnesium sulfate and the ether removed by distillation under reduced pressure to yield 1-acetyl-2,2,6,6-tetramethylpiperidinyl-4-acetate having a melting point of 33°-4° C and the following elemental analysis by weight:

|  | Found | Required (for $C_{13}H_{23}NO_3$) |
|---|---|---|
| Carbon | 64.51 % | 64.73 % |
| Hydrogen | 9.69 % | 9.54 % |
| Nitrogen | 5.67 % | 5.81 % |

EXAMPLE 87

A mixture of 15.70 parts of 2,2,6,6-tetramethylpiperidin-4-ol, 22.80 parts of methyl isocyanate and 0.5 parts of 1,4-dazabicyclo[2,2,2]octane in 100 parts of dry benzene was heated under reflux conditions for 24 hours. The benzene solvent was removed by distillation under reduced pressure and 150 parts of water added to the residue which was stood overnight at room temperature. The solid formed was collected by filtration and dried to yield 19.60 parts of a white crystalline solid having a melting point of 167°-8° C. This solid was shown to contain 80% of 4-methylcarbamoyl-1-methylcarbamoyl-2,2,6,6-tetramethylpiperidine from microanalysis and nuclear magnetic resonance spectra.

EXAMPLE 88 a. 2.65 parts of acrylonitrile was added dropwise with stirring to a solution of 8.55 parts of 1,2,2,6,6-pentamethylpiperidin-4-ol and 0.30 parts of 40% potassium hydroxide solution in 80 parts of benzene. Stirring was continued at room temperature for 16 hours after which time the solution was washed with water, dried and the benzene solvent removed by distillation under reduced pressure. Fractional distillation of the residue, under reduced pressure gave 1.70 parts of 4-(2'-cyanoethoxy)-1,2,2,6,6-pentamethylpiperidine having a boiling point of 105°-6° C at 0.1 mm of Hg and the following elemental analysis by weight:

|  | Found | Required (for $C_{13}H_{24}N_2O$) |
|---|---|---|
| Carbon | 69.27 % | 69.60 % |
| Hydrogen | 10.69 % | 10.78 % |
| Nitrogen | 12.40 % | 12.49 % | b. To 51 parts of 1,2,2,6,6-pentamethylpiperidin-4-ol a solution of metallic sodium in two parts of tert.butanol was added. 52.5 parts of acrylonitrile was dropped in with rapid stirring. After standing for two days at room temperature the mixture was heated to 80° C for two hours and distilled under reduced pressure yielding 4-(2'-cyanoethoxy) 1,2,2,6,6-pentamethylpiperidine with a boiling point of 172°-4° C at 17 mm Hg. This sample was identical to that prepared under Example 88a.

EXAMPLE 89

A misture of 13.0 parts of 4-dodecyloxy-2,2,6,6-tetramethylpiperidine and 3.42 parts of benzyl bromide was heated at 100° C for 48 hours. Petroleum ether (b.p. 40°-60° C) was added to the cooled reaction mixture and the 4-dodecyloxy-2,2,6,6tetramethylpiperidine hydrobromide formed during the reaction was filtered off. The petroleum ether solvent was removed by distillation under reduced pressure and the residue fractionally distilled to give 4-dodecyloxy-1-benzyl-2,2,6,6-tetramethylpiperidine having a boiling point of 200° C at 0.5 m.m. of Hg. and the following elemental analysis by weight:

|  | Found | Required (for $C_{28}H_{49}NO$) |
|---|---|---|
| Carbon | 80.67 % | 80.90 % |
| Hydrogen | 11.82 % | 11.88 % |
| Nitrogen | 3.34 % | 3.37 % |

EXAMPLE 90

A mixture of 4-benzyloxy-2,2,6,6-tetramethylpiperidine and 1.67 parts of ethyl α-bromoacetate in 30 parts of ethyl alcohol was heated under reflux conditions for 115 hours. The ethyl alcohol solvent was removed by distillation under reduced pressure and the residue fractionally distilled to give 4-benzyloxy-1-ethoxycarbonylmethyl]-2,2,6,6-tetramethylpiperidine having a boiling point of 145°-6° C at 0.2 m.m. of Hg. and the following elemental analysis by weight:

|  | Found | Required (for $C_{20}H_{31}NO_3$) |
|---|---|---|
| Carbon | 71.62 % | 72.04 % |
| Hydrogen | 8.90 % | 9.37 % |
| Nitrogen | 3.94 % | 4.20 % |

EXAMPLE 91

A mixture of 25.7 parts of 1,2,2,6,6-pentamethyl-piperidin-4-ol and 3.09 parts of boric acid in 100 parts of toluene was heated under reflux conditions with azeotropic removal of water for 24 hours. The toluene solvent was removed by distillation under reduced pressure to give tris-(1,2,2,6,6-4-piperidinyl)borate having a melting point of 83°-9° C and the following elemental analysis by weight:

|  | Found | Required (for $C_{30}H_{60}N_3O_3B$) |
|---|---|---|
| Carbon | 68.85 % | 69.05 % |
| Hydrogen | 11.68 % | 11.59 % |
| Nitrogen | 7.76 % | 8.06 % |

EXAMPLE 92

30 parts of 1,2,2,6,6-pentamethylpiperidin-4-ol were dissolved in 250 parts of benzene and 4 parts of sodium added. The solution was heated overnight at reflux temperature and then cooled. 38 parts of 2-phenoxyethanol tosylate were added dropwise and the solution heated at reflux for 5 hours. On cooling the precipitate was filtered off and the filtrate evaporated on vacuo. Treatment of the residue with dilute hydrochloric acid and then basification with dilute sodium hydroxide to a pH 10 was followed by extraction with ether. Evaporation afforded a pale yellow oil which was chromatographed on alumina to give 4-(2'-phenoxyethoxy)-1,2,2,6,6-pentamethylpiperidine as a colourless oil which gave the following elemental analysis by weight:

|  | Found | Required (for $C_{18}H_{29}NO_2$) |
|---|---|---|
| Carbon | 72.49 % | 74.18 % |
| Hydrogen | 9.89 % | 10.03 % |
| Nitrogen | 4.91 % | 4.81 % |

EXAMPLE 93

A mixture of 9.87 parts of 4-allyloxy-2,2,6,6-tetramethylpiperidine and 3.03 parts of allyl bromide was heated at 90° C for 96 hours. Ether was added to the cooled reaction mixture and the 4-allyloxy-2,2,6,6-tetramethylpiperidine hydrobromide formed during the reaction was filtered off. The ether solvent was removed by distillation under reduced pressure and the residue purified by chromatography to give 4-allyloxy-1-allyl-2,2,6,6-tetramethylpiperidine.

EXAMPLES 94 – 116

TESTING IN POLYPROPYLENE FILM 38 parts of polypropylene were homogenised with 0.076 parts of n-octadecyl-$\beta$(4'-hydroxy-3',5'-t-butylphenyl) propionate in a kneading machine over a period of 3 minutes at 200° C. 0.19 parts of the product of Example 13 was then added and homogenisation continued for another 7 minutes.

This composition was compression moulded into films of 0.1 mm thickness at 260° C for 6 minutes amd the films so obtained were then quenched in cold water.

A section measuring 44 × 100 mm was separated from the 0.1 mm annealed polypropylene foil and exposed to light irradiation in a fademeter device consisting of a circular bank of 28 alternate sunlight and blacklight lamps. The sunlight lamps were 2 feet long, 20-watt fluorescent lamps characterised by a peak emission of 3,100 Angstrom units; the backlight lamps were 2 feet long, 20 -watt ultraviolet lamps characterised by a peak emission of 3,500 Angstrom units. The sample was rotated concentrically about the bank of lamps so that the radiation therefrom was uniformly distributed over the section under test.

The exposed sample was examined periodically and portions of it tested for the percent/elongation at break, the time at which the sample reached 50% of the initial elongation at break was noted.

Similar tests were carried out on polypropylene samples containing, respectively, no stabiliser and known stabilisers, and also stabilisers falling within the scope of German Pat. No. 1,929,928. The results obtained are set out in the following table:

TABLE

| Example | Additive | Factor: Time to 50% of initial elongation at break (additive) / Time to 50% of initial elongation at break (control) |
|---|---|---|
| — | none | 1.0 |
| — | 2-(2'-hydroxy-3',5'-di-t-butylphenyl)-5-chlorobenzotriazole | 3.2 |
| — | 4-phenylcarbamoyloxy-2,2,6,6-tetramethylpiperidine | 1.8 |
| — | 1,6-bis[4'-carbamoyloxy-2',2',6',6'-tetramethylpiperidine]hexane | 2.4 |
| — | 2,2,6,6-tetramethylpiperidinyl-4-benzoate | 2.6 |
| — | bis(2,2,6,6-tetramethyl-4-piperidinyl)sebacate | 4.7 |
| 94 | 1,2,2,6,6-pentamethylpiperidinyl-4-phenylacetate | 5.2 |
| 95 | bis(1,2,2,6,6-pentamethyl-4-piperidinyl)terephthalate | 5.3 |
| 96 | 1,2,2,6,6-pentamethypiperidinyl-4-(p-methoxybenzoate) | 5.3 |
| 97 | 1,2,2,6,6-pentamethylpiperidinyl-4-(1'-naphthoate) | 5.4 |
| 98 | 1,2,2,6,6-pentamethylpiperidinyl-4-octanoate | 6.2 |
| 99 | 1,2,2,6,6-pentamethylpiperidinyl-4-isobutyrate | 6.2 |
| 100 | bis(1,2,2,6,6-pentamethyl-4-piperidinyl)sebacate | 8.0 |
| 101 | 2,4-bis(4'-carbamoyloxy-1',2',2',6',6'-pentamethylpiperidine)toluene | 5.2 |
| 102 | 4-p-tolylcarbamoyloxy-1,2,2,6,6-pentamethylpiperidine | 5.2 |
| 103 | 4-allylcarbamoyloxy-1,2,2,6,6-pentamethylpiperidine | 5.5 |

TABLE -continued

| Example | Additive | Factor: Time to 50% of initial elongation at break (additive) / Time to 50% of initial elongation at break (control) |
|---|---|---|
| 104 | 4-phenylcarbamoyloxy-1,2,2,6,6-pentamethylpiperidine | 5.6 |
| 105 | 4-methylcarbamoyloxy-1,2,2,6,6-pentamethylpiperidine | 5.8 |
| 106 | 1,6-bis[4'-carbamoyloxy-1',2',2',6',6'-pentamethylpiperidine]hexane | 9.2 |
| 107 | bis(1-benzyl-2,2,6,6-tetramethyl-4-piperidinyl)sebacate | 5.0 |
| 108 | 1-ethoxycarbonylmethyl-2,2,6,6-tetramethylpiperidinyl-4-(p-methoxybenzoate) | 5.1 |
| 109 | 1-benzyl-2,2,6,6-tetramethylpiperidinyl-4-(2-ethylhexanoate) | 5.2 |
| 110 | 1-(n-dodecyl)-2,2,6,6-tetramethylpiperidinyl-4-octanoate | 5.2 |
| 111 | 1(2'-hydroxyethyl)-2,2,6,6-tetramethylpiperidinyl-4-octanoate | 5.8 |
| 112 | 1-(n-propyl)-2,2,6,6-tetramethylpiperidinyl-4-octanoate | 6.0 |
| 113 | 4-(n-dodecyloxy)-1,2,2,6,6-pentamethylpiperidine | 5.5 |
| 114 | 4-(2'-cyanoethoxy)-1,2,2,6,6-pentamethylpiperidine | >6.0 |
| 115 | 1,4-bis(1',2',2',6',6'-pentamethyl-4-piperidinyloxy)-butane | >6.0 |
| 116 | Tris(1,2,2,6,6,pentamethyl-4-piperidinyl)borate | 5.0 |

EXAMPLES 117 TO 119

The procedure described in Examples 94–116 was repeated except that 0.25% by weight of the light stabiliser under test was used, and, instead of polypropylene, a low-density polyethylene was employed at substrate.

The pressing was conducted at 180° C and the pressings were compression-moulded into 1 mm. thick plaques at 150° C.

The plaques were stored at 20° C and were periodically examined visually for the first sign of exudation.

The results obtained are summarised in the following Table which also includes data relating to comparative experiments (known light stabilisers added).

TABLE

| Example | Light stabiliser added | Time to exudation (days) |
|---|---|---|
| — | 2,2,6,6-tetramethylpiperidinyl-4-stearate | 15 |
| — | bis(2,2,6,6-tetramethyl-4-piperidinyl)sebacate | 20 |
| — | 4-stearylcarbamoyloxy-2,2,6,6-tetramethylpiperidine | 13 |
| 117 | 1,2,2,6,6-pentamethylpiperidinyl-4-stearate | >50 |
| 118 | bis(1,2,2,6,6-pentamethyl-4-piperidinyl)sebacate | >50 |
| 119 | 4-stearylcarbamoyloxy-1,2,2,6,6-pentamethylpiperidine | >50 |

EXAMPLES 120 to 122

The procedure described in Examples 117 to 119 was repeated except that the compression moulding was carried out at 200° C and the substrate used was high-density polyethylene.

The results obtained are set out in the following Table, which also contains data relating to comparative experiments (using a known light stabiliser).

TABLE

| Example | Light Stabiliser | Time to exudation (days) |
|---|---|---|
| — | 2,2,6,6-tetramethylpiperidinyl-4-stearate | 40 |
| 120 | 1,2,2,6,6-pentamethylpiperidinyl-4-stearate | >75 |
| 121 | 4-stearylcarbamoyloxy-1,2,2,6,6-tetramethylpiperidine | >75 |
| 122 | 1-(n-dodecyl)-2,2,6,6-tetramethyl-piperidinyl-4-ocanoate | >75 |

Examples 123 to 128

100 Parts of crystal polystyrene pellets were dry blended with 0.25 part of 1,2,2,6,6-pentmethylpiperidinyl-4-stearate, and the dry blend was homogenised by extension. The stabilised pellets so obtained were injection moulded for form plaques 2 mm. thick. These plaques were exposed for 3000 hours in a Xenotest 150 exposure unit, and any yellowing of the plaques was measured by determining the yellowness factor by means of the following equation:

$$\text{yellowness factor} = \frac{\Delta T_{(420)} - \Delta T_{(680)}}{T_{(560)}} \times 100$$

wherein the $\Delta T$ values represent the transmission loss of the sample at wavelengths of 420 mm. and 680 mm. respectively, after exposure in the Xenotest unit, and $T_{(560)}$ represents the transmission value of an unexposed sample at a wavelength of 560 mm.

The results obtained, as well as the results relating to a control experiment and other compositions of this invention are recorded in the following Table.

TABLE

| Example | Light stabiliser | Yellowing factor after 3000 hours |
|---|---|---|
| — | none | 35.0 |
| 123 | 1,2,2,6,6-pentamethylpiperidinyl-4-stearate | 10.0 |
| 124 | 1-benzyl-2,2,6,6-tetramethylpiperidinyl-4-(2'-ethylhexanoate) | 9.8 |
| 125 | 1,2,2,6,6-pentamethylpiperidinyl-4-(n-octanoate) | 9.5 |
| 126 | 4-(2'-cyanoethoxy)-1,2,2,6,6-pentamethylpiperidine | 8.0 |
| 127 | 4-stearylcarbamoyloxy-1,2,2,6,6-pentamethylpiperidine | 7.5 |
| 128 | bis-(1,2,2,6,6-pentamethyl-4-piperidinyl)sebacate | 6.6 |

EXAMPLES 129 to 132

25 parts by weight of a polyester-based film-forming polyurethane were dissolved in 75 parts by weight of a 1:1 mixture (by volume) of dimetylformamide and acetone, and 1 % by weight of 4(2'-cyanoethoxy)-1,2,2,6,6-pentamethylpiperidine was added.

The clear and homogeneous solution was drawn out on a glass plate to a film of 400–500 μ thickness, which was then dried as follows:

at 50° C for 4 minutes at 140° C for 6 minutes

The final thickness of the film was 80–100 μ.

The dried film samples were removed from the glass plate, mounted on white cardboard and exposed in a Xenotest 450 exposure unit, one half of the exposed sample being covered to facilitate subsequent visual estimation of yellowing due to exposure. The sample was controlled and rated visually at intervals of 100 hours.

The data obtained are set out in the following Table which also includes data relating to a control experiment (no added light stabiliser) and to other experiments using stabilisers of this invention.

TABLE

| Example | Light Stabiliser | Time to onset of yellowing (hours) |
|---|---|---|
| — | none | >100 |
| 129 | 4-(2'-cyanoethoxy)-1,2,2,6,6-pentamethylpiperidine | 200 |
| 130 | 1,2,2,6,6-pentamethyl-piperidinyl-4-octanoate | 300 |
| 131 | bis-(1,2,2,6,6-pentamethyl-4-piperidinyl)sebacate | 300 |
| 132 | 4-phenylcarbamoyloxy-1-n-propyl-2,2,6,6-tetramethyl-piperidine | 400 |

EXAMPLES 133–135

1000 Parts by weight of unstabilised polypropylene powder were thoroughly dry-blended with 1 part by weight of n-octadecyl-β-(4'-hydroxy-3',5'-di-t-butylphenyl) propionate and 2 parts by weight of 1,2,2,6,6 propionate and 2 parts by weight of 1,2,2,6,6pentamethyl-4-piperidinyl-(3',5'-di-t-butyl-4'-hydroxy) benzoate. The dry-blend was extruded at cylinder temperatures of from 180° to 220° C, and the resulting strand was granulated. The stabilised formulation so obtained was melt-spun and stretched under the following conditions:

| | |
|---|---|
| Extruder temperatures | 230/265/275° C. |
| Melt Temperature at the dye | 270° C. |
| Spinning speed | 400 m./minute |
| Stretching Ratio | 1 : 5 |
| Titer of Multifilament | 130/137 denier |
| Tensile Strength | 6 g./denier |

The multifilament obtained was mounted on a sample holder of a Xenotest 150 apparatus (Quarzlampen GmbH) using white cardboard as backing. In intervals of 200 hours of exposure time, 5 fibre samples are measured for their retained tensile strength. The data obtained are plotted against exposure time and the exposure time (T) to give 50% loss of original tensile strength is derived from the graph. This value is taken as the failure time.

EXAMPLES 136 to 144

The procedure described in Examples 94 to 116 was repeated except that the annealed polypropylene specimens were exposed to light irradiation in a Xenotest 450 exposure unit rather than in the fademeter device.

The results obtained are summarised in the following Table which also includes data relating to a control experiment (no added light stabiliser) and a comparative experiment (a known light stabiliser added).

TABLE

| Ex. | Light Stabiliser | Time to Failure (hours) |
|---|---|---|
| — | none (control) | 800 |
| — | 2-(2'-hydroxy-3',5'-di-t-butylphenyl)-5-chlorobenzotriazole | 1630 |
| 136 | bis(1,2,2,6,6-pentamethyl-4-piperidinyl)sebacate | >9000 |
| 137 | 1,2,2,6,6-pentamethylpiperidinyl-4-β-(3',5'-di-t-butyl-4'-hydroxyphenyl) propionate | 10,000 |
| 138 | 1,2,2,6,6-pentamethylpiperidinyl-4-(3',5'-di-t-butyl-4'-hydroxy benzoate) | >8600 |
| 139 | 1,2,2,6,6-pentamethylpiperidinyl-4-octanoate | 6500 |
| 140 | 4-phenylcarbamoyloxy-1,2,2,6,6-pentamethyl piperidine | >7000 |
| 141 | 4-methylcarbamoyloxy-1,2,2,6,6-pentamethylpiperidine | 6000 |
| 142 | 1,2,2,6,6-pentamethylpiperidinyl-4-cyclohexane-carboxylate | >6000 |
| 143 | 1,2,2,6,6-pentamethylpiperidinyl-4-stearate | >6000 |
| 144 | 1,2,2,6,6-pentamethylpiperidinyl-4-benzoate | >5000 |

EXAMPLES 145–150

100 Parts by weight of polyamide-6 pellets containing 1.8 parts by weight of TiO$_2$ were dry-blanded with 0.5 part of 4-benzyloxy-1,2,2,6,6-pentamethyl piperidine. The resulting mixture was melt-spun directly into monofilaments of 20 denier. The monofilaments were mounted on white cardboard without tension and were exposed to light radiation in a Xenotest 450 exposure unit.

After 500, 1,000, 1,500 and 2000 hours of exposure time respectively, 5 fibre samples of each formulation and time interval were tested for tensile strength. The arithmetic mean percentage values of residual tensile strength were plotted as a function of exposure time. The failure points — time to 50% loss of original tensile strength — were obtained from these graphs.

TABLE

| Ex. | Light Stabiliser | Time to 50% loss of original tensile strength (hours) |
|---|---|---|
| — | none (control) | 475 |

TABLE

| Example No. | Light Stabiliser | Time (T) to 50% retained tensile strength | Factor T stabiliser / T control |
|---|---|---|---|
| none | none | 430 | 1.0 |
| | 2-(2'-hydroxy-3',5'-di-t-butylphenyl)-5-chlorobenzotriazole | 530 | 1.2 |
| 133 | 1,2,2,6,6-Pentamethyl-4-piperidinyl-(3',5'-di-t-butyl-4'-hydroxy benzoate) | 1,400 | 3.3 |
| 134 | 1,2,2,6,6-Pentamethyl-4-piperidinyl-β-(3',5'-di-t-butyl-4'-hydroxyphenyl) propionate | 1,600 | 3.7 |
| 135 | Bis(1,2,2,6,6-pentamethyl-4-piperidinyl) sebacate | 2,600 | 6.0 |

TABLE-continued

| Ex. | Light Stabiliser | Time to 50% loss of original tensile strength (hours) |
|---|---|---|
| 145 | 4-benzyloxy-1,2,2,6,6-pentamethylpiperidine | 1420 |
| 146 | bis(1,2,2,6,6-pentamethyl-4-piperidinyl)sebacate | 1600 |
| 147 | 1,2,2,6,6-pentamethylpiperidinyl-4-octanoate | 1450 |
| 148 | 1-phenylcarbamoyloxy-1,2,2,6,6-pentamethylpiperidine | 1450 |
| 149 | 1,6-bis(4'-carbamoyloxy-1',2'-2',6',6'-pentamethylpiperidine)hexane | 1500 |
| 150 | 1,4-bis(1',2',2',2',6',6'-pentamethyl-4'-piperidinyloxy)butane | 1600 |

What we claim is:

1. A composition comprising an organic material and 0.01% to 5% by weight of a stabilizer having the formula

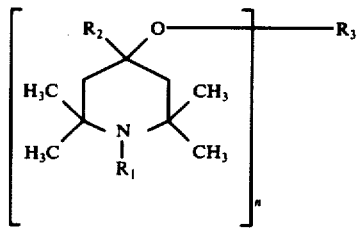

and their salts
wherein $n$ is 1, 2, 3 or 4;
$R_1$ is a monovalent residue and is an alkyl residue from 1 to 20 carbon atoms, an alkenyl or alkynyl residue having from 3 to 20 carbon atoms, an aralkyl residue having from 7 to 12 crbon atoms, or a residue having the formula:

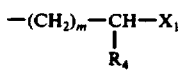

or

wherein $m$ is 1, 2 or 3,
$R_4$ is a hydrogen, methyl or phenyl residue, $X_2$ is halogen, cyano,

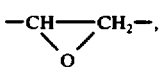

—$COR_5$, —$CO.OR_5$, —$CO.SR_5$—,
or —$CONR_5R_6$ and
$X_1$ is hydroxyl, halogen, cyano,

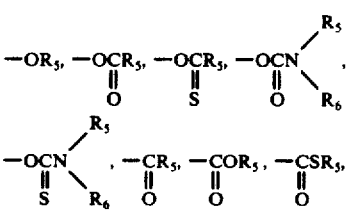

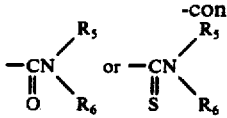

where $R_5$ is an alkyl residue having from 1 to 20 carbon atoms, an alkenyl residue having from 2 to 20 carbon atoms, a cycloalkyl residue having from 5 to 12 carbon atoms, an aryl residue having from 6 to 11 carbon atoms or an aralkyl residue having 7 to 14 carbon atoms or when $R_5$ is joined to a nitrogen atom, also hydrogen and $R_6$ is hydrogen or an alkyl residue having from 1 to 4 carbon atoms, or $R_5$ and $R_6$ together with the nitrogen atom to which they are bound form a 5- or 6-membered ring which contains no other hetroatoms or contains one or more other heteroatoms, or $R_1$ is an acyl group

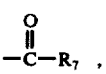

where $R_7$ is hydrogen, an unsubstituted aliphatic or substituted aliphatic residue having from 1 to 20 carbon atoms, an alkenyl or alkynyl residue having from 2 to 20 carbon atoms, a cycloaliphatic residue having from 5 to 12 carbon atoms, an araliphatic residue having from 7 to 14 carbon atoms, an aromatic residue having from 6 to 20 carbon atoms or an heterocyclic residue, or
$R_1$ is a carbamoyl or thiocarbamoyl residue having the formula:

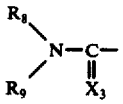

wherein $X_3$ is —O— or —S—,
$R_8$ is hydrogen or an alkyl residue having from 1 to 4 carbon atoms, and
$R_9$ is hydrogen, an alkyl residue having from 1 to 20 carbon atoms, an alkenyl residue having from 3 to 20 carbon atoms, a cycloalkyl residue having from 5 to 12 carbon atoms or an unsubstituted aryl or substituted aryl residue having from 6 to 12 carbon atoms;
$R_2$ is an alkyl residue having from 1 to 4 carbon atoms, an alkenyl or alkynyl residue having 3 to 20 carbon atoms, a cycloalkyl residue having from 5 to 12 carbon atoms, an aryl residue having from 6 to 11 carbon atoms or an aralkyl residue having from 7 to 9 carbon atoms or hydrogen; and
when $n$ is 1, $R_3$ is a monovalent residue and is an alkyl residue having from 1 to 20 carbon atoms, a cycloalkyl residue having from 5 to 12 carbon atoms, an alkenyl or alkynyl residue hving from 3 to 20 carbon atoms, an aralkyl residue having from 7 to 12 carbon atoms, or a residue having the formula:

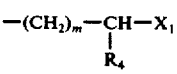

or

wherein $m$ is 1, 2 or 3,
$R_4$ is a hydrogen, methyl or phenyl residue, $X_2$ is halogen, cyano,

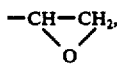

—$COR_5$, —$CO.OR_5$, —$CO.SR_5$, or $CONR_5R_6$
and
$X_1$ is hydroxyl, halogen, cyano,

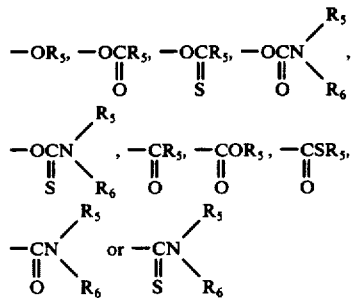

wherein $R_5$ is an alkyl residue having from 1 to 20 carbon atoms, an alkenyl residue having from 2 to 20 carbon atoms, a cycloalkyl residue having from 5 to 12 carbon atoms, an aryl residue having from 6 to 11 carbon atoms or an aralkyl residue having 7 to 14 carbon atoms, or when $R_5$ is joined to a nitrogen atom, also hydrogen and
$R_6$ is hydrogen or an alkyl residue having from 1 to 4 carbon atoms, or
$R_5$ and $R_6$ together with the nitrogen atom to which they are bound form a 5- or 6-membered ring which contains no other heteroatoms or contains one or more other heteroatoms, or
$R_3$ is an acyl group,

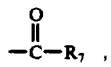

wherein $R_7$ is hydrogen, an unsubstituted aliphatic or substitued aliphatic residue having from 1 to 20 carbon atoms, an alkenyl or alkynyl residue hving from 2 to 20 carbon atoms, a cycloaliphatic residue having from 5 to 12 carbon atoms, an araliphatic residue having from 7 to 14 carbon atoms, an aromatic residue having from 6 to 20 carbon atoms or an heterocyclic residue, or
$R_3$ is a carbamoyl or thiocarbamoyl residue having the formula:

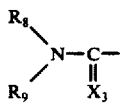

wherein $X_3$ is —O— or —S—,
$R_8$ is hydrogen or an alkyl residue having from 1 to 4 carbon atoms, and
$R_9$ is hydrogen, an alkyl residue having from 1 to 20 carbon atoms, an alkenyl residue having from 3 to 20 carbon atoms, a cycloalkyl residue having from 5 to 12 carbon atoms or an unsubstituted aryl or substituted aryl residue having from 6 to 12 carbon atoms; or
$R_3$ represents a monovalent group obtained by removing a hydroxyl group from a sulphinic acid, a sulphonic acid, a phosphorus containing acid or a boric acid, or $R_3$ is an aryl residue or a residue having the formula:

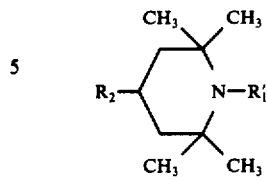

wherein $R_1'$ is hydrogen or $R_1'$ has the same significance as $R_1$:
when $n$ is 2, $R_3$ is a divalent residue and is an aklkylene residue having from 1 to 20 carbon atoms, an alkenylene residue having from 2 to 20 carbon atoms, an alkynylene residue having from 2 to 20 carbon atoms, a cycloalkyliden residue having from 5 to 12 carbon atoms, an arylene residue having 6 to 14 carbon atoms, an aralylene residue having from 8 to 14 carbon atoms or an aliphatic, aromatic or heterocyclic diacyl residue, the group —Co— or —CO.CO—, an aliphatic or aromatic dicabamoyl or dithiocarbamoyl, sulphinyl or sulponyl residue or a divalent residue obtained by removing two hydroxyl groups from a disulphonic acid, a phosphorus containing acid or a boric acid;
when $n$ is 3, $R_3$ is a trivalent residue and is an alkanetriyl, an arenetriyl or an arenetriyl-trialkylene residue, an aliphatic or aromatic triacyl residue or a triacyl residue derived from o-phosphoric, o-phosphorous or o-boric and
when $n$ is 4, $R_3$ is a tetravalent residue and is an alkanetetrayl residue or a tetraacyl residue derived from an aliphatic or aromatic tetracarboxylic acid or from o-silicic acid as well as, when $n$ is 2, 3 or 4, partial ethers, esters and carbamoyloxy and thiocarbamoyloxy compounds related to the fully reacted compounds of formula I; provided that when a compound of formula I is an ester, the alkyl group of $R_1$ has only 5 to 20 carbon atoms.

2. A composition as claimed in claim 1 wherein the organic material is a natural or synthetic polymeric material.

3. A composition as claimed in claim 2 wherein the synthetic polymeric material is a polyolefin selected from low-or high-density polyethylene, polypropylene or polystyrene, a polymer of butene-1, pentene-1, 3-methylbutene-1, hexene-1, 4-methylpentene-1, 4-methylhexene-1, 4,4-di-methyl-pentene-1 or co- or terpolymers of ethylene or propylene; polyvinyl chloride, polyvinylidene chloride, vinyl chloride copolymers, polyvinyl acetate; a condensation polymer derived from ether, ester (derived from carboxylic sulphonic or cabonic acids), amide or urethane groups; or a mono- co- or terpolymer of acrylonitrile, butadiene and styrene.

4. A composition as claimed in claim 3 wherein the amount of the stabilizer is within the range of from 0.1% to 2% by weight based on the weight of untreated organic material.

5. A composition as claimed in claim 4 containing additionally one or more of further additives selected from an antioxidant of the phenol or amine type, U.V. absorber and light protectant, phosphite stabilizer, peroxide decomposer, polyamide stabilizer, basic co-stabilizer, polyvinyl chloride stabilizer, lubricant, emulsifier, anti-static agent, flame-protectant, pigment, carbon black, asbestos, glass fibers, kaolin and talc.

6. A composition as claimed in claim 1 wherein the stabilizer has the formula

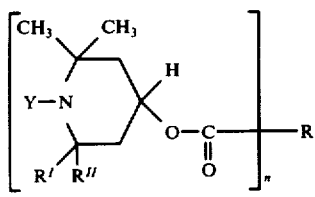

II and their salts, wherein R$^I$ and R$^{II}$ are the same or different and each is straight or branched alkyl group, having from 1 to 4 carbon atoms, or R$^I$ and R$^{II}$, together with the carbon atom to which they are attached form a cycloalkyo residue having from 5 to 12 carbon atoms; Y is an alkyl group, having from 1 to 20 carbon atoms, alkenyl having from 2 to 20 carbon atoms or an aralkyl residue having from 7 to 9 carbon atoms, and n is 1 or 2; when n is 1, R is hydrogen or a monovalent aliphatic residue having from 5 to 20 carbon atoms, a monovalent alicyclic residue having frm 5 to 12 carbon atoms, or a monovalent aromatic residue having from 6 to 20 carbon atoms; and when n is 2, R is a divalent aliphatic residue having from 1 to 20 carbon atoms, and is unsubstituted or interrupted by one or more sulphur atoms, a divalent alicyclic residue having from 5 to 12 carbon atoms, or a divalent aromatic residue having from 6 to 20 carbon atoms.

7. A composition as claimed in claim 6 wherein the organic material is a polyolefine.

8. A composition as claimed in claim 6 wherein the polyolefine is a low- or high-density polyethylene or polypropylene or polystyrene.

9. A composition as claimed in claim 6 wherein the polymeric material is polyvinyl chloride, a vinyl chloride co-polymer, polyvinyl acetate; a condensation polymer derived from ether, ester (derived from carboxylic, sulphonic or carbonic acids), amide or urethane groupings; a mono-, or co- or terpolymer of acrylonitrile, butadiene and styrene; a polymer of butene-1, pentene-1, 3-methyl-butene-1, hexene-1, 4,4-dimethylpentene1, or co- or terpolymers of ethylene or propylene.

10. A composition as claimed in claim 1 wherein the stabilizer has the formula

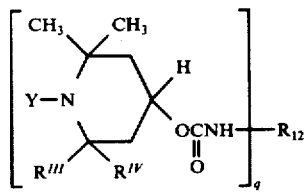

IV and its salts wherein R$^{III}$ and R$^{IV}$ are the same or different and each is a straight or branched alkyl residue having from 1 to 12 carbon atoms or R$^{III}$ and R$^{IV}$ together with the carbon atom to which they are each attached form a cycloalkyl group having from 5 to 12 carbon atoms, Y is a straight- or branched alkyl residue having from 1 to 12 carbon atoms, an alkenyl residue having from 3 to 12 carbon atoms or an aralkyl residue having from 7 to 12 carbon atoms and R$_{12}$ is hydrogen or a saturated or unsaturated hydrocarbyl residue containing up to 20 carbon atoms optionally substituted, Y is halogen or alkoxy having from 1 to 4 carbon atoms and q is 1 or 2.

11. A composition as claimed in claim 10 wherein the organic material is a polyolefine.

12. A composition as claimed in claim 11 wherein the polyolfine is a low- or high-density polyethylene or polypropylene or polystyrene.

13. A composition as claimed in claim 10 wherein the polymeric material is polyvinyl chloride, a vinyl chloride co-polymer, polyvinyl acetate; a condensation polymer derived from ether, ester (derived from carboxylic, sulphonic or carbonic acids) amide or urethane groupings; a polymer of butene-1, pentene-1, 3-methyl-butene-1, hexene-1, 4-methylpentene-1, 4-methyl-hexene-1, 4,4-dimethylpentene-1; co- or ter-polymers of ethylene or propylene or a homo-, co- or ter-polymer of acrylonitrile, butadiene and styrene.

14. A composition as claimed in claim 1 wherein the stabilizer has the formula

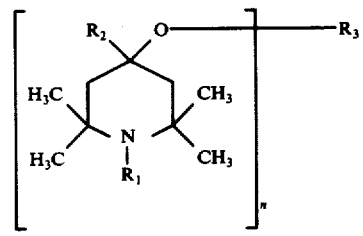

I wherein n is 1, 2, 3 or 4;

R$_1$ is a monovalent residue and is an alkyl residue having from 1 to 20 carbon atoms, an alkenyl or alkynyl residue having from 3 to 20 carbon atoms, an aralkyl residue having from 7 to 9 carbon atoms, or a residue having the formula:

$$-(CH_2)_m-CH-X_1$$
$$\phantom{-(CH_2)_m-CH}|$$
$$\phantom{-(CH_2)_m-CH}R_4$$

or $$-CH-X_2$$
$$\phantom{-CH}|$$
$$\phantom{-CH}R_4$$

wherein m is 1, 2 or 3,
R$_4$ is a hydrogen, methyl or phenyl residue,
X$_2$ is halogen, cyano,

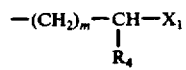

—COR$_5$, —CO.OR$_5$, —CO.SR$_5$, —CONR$_5$R$_6$, or —CS.NR$_5$R$_6$ and X$_1$ is hydroxyl, halogen, cyano,

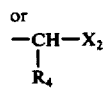

—OR$_5$, —O—CO.R$_5$, OCSR$_5$, —O.CO.NR$_5$R$_6$, —CO.R$_5$, —CO.OR$_5$, —CO.SR$_5$, —CO.NR$_5$R$_6$, —CS.NR$_5$R$_6$ or —SR$_5$, wherein R$_5$ is an alkyl residue having from 1 to 20 carbon atoms, an alkenyl residue having from 2 to 20 carbon atoms, a cycloalkyl residue having from 5 to 12 carbon atoms, an aryl residue having from 6 to 11 carbon atoms or when R$_5$ is joined to a nitrogen atom, also hydrogen and R$_6$ is hydrogen or an alkyl residue having from 1 to 4 carbon atoms, or R$_5$ and $R_6$ together with the nitrogen atom to which they are bound form a 5- or 6-membered ring which contains no other heteroatoms or contains one or more other heteroatoms or $R_1$ is an acyl group, an unsubstituted or N-substituted carbamoyl or thiocarbamoyl group; $R_2$ is an alkyl residue having from 1 to 4 carbon atoms, an alkenyl or alkynyl residue having 3 to 20 carbon atoms, a cycloalkyl residue having from 5 to 12 carbon atoms, an aryl residue having from 6 to 11 carbon atoms or an aralkyl residue having from 7 to 9 carbon atoms or also hydrogen:

and when $n$ is 1, $R_3$ is a monovalent radical having the same significance as $R_1$, with the proviso that only one of $R_1$ and $R_3$ can represent an unsaturated acyl group or $R_3$ represents a monovalent group obtained by removing a hydroxyl group from a sulphinic acid, a sulphonic acid, a phosphorus containing acid or a boric acid, or $R_3$ is an aryl residue or a residue having the formula

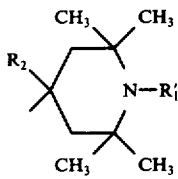

wherein $R_1'$ is hydrogen or $R_1'$ has the same significance as $R_1$;

when $n$ is 2, $R_3$ is a divalent residue and is an alkylene residue having from 1 to 20 carbon atoms, an alkenylene residue having from 3 to 20 carbon atoms, an alkynylene residue having from 3 to 20 carbon atoms, an arylene residue having 6 to 14 carbon atoms an aralkylene residue having from 8 to 14 carbon atoms or an aliphatic aromatic or heterocyclic diacyl residue, an aliphatic or aromatic dicarbamoyl or dithiocarbamoyl, a carbonyl, sulphinyl or sulphonyl residue or a divalent residue obtained by removing two hydroxyl groups from a disulphonic acid, a phosphorus containing acid or a boric acid;

when $n$ is 3, $R_3$ is a trivalent residue or an aliphatic or aromatic triacyl residue or a triacyl residue derived from o-phosphoric, o-phosphorous or o-boric acid or an alkanetriyl, an arenetriyl, or arenetriyltrialkylene group;

and when $n$ is 4, $R_3$ is a tetravalent residue and is a tetravalent aliphatic residue or tetraaccyl residue derived from an aliphatic or aromatic tetracarboxylic acid or from o-silicic acid or an alkanetetrayl group;

as well as partial ethers, esters and carbamoyloxy and thiocarbamoyloxy compounds related to the fully reacted compounds of formula I; provided that when a compound of formula I is an ester, the alkyl group or $R_1$ has only 5 to 20 carbon atoms.

15. A composition of claim 3 where the stabilizer is 1,6-bis(4'-carbamoyloxy-1', 2', 2', 6', 6'-pentamethylpiperidine)-hexane.

16. A composition of claim 3 where the stabilizer is 4-stearyl-carbamoyloxy-1,2,2,6,6-pentamethylpiperidine.

* * * * *